United States Patent [19]

Kaper et al.

[11] Patent Number: 5,470,729
[45] Date of Patent: Nov. 28, 1995

[54] **METHOD OF ISOLATING RESTRICTION FRAGMENT DELETIONS IN *VIBRIO CHOLERAE*, AND PRODUCTS THEREOF**

[75] Inventors: James B. Kaper, Columbia; Bernadette Baudry-Maurelli, Silver Spring, both of Md.; Alessio Fasano, Salerno, Italy

[73] Assignee: University of Maryland At Baltimore, Baltimore, Md.

OTHER PUBLICATIONS

Finkelstein, R. et al., "Studies On Toxinogenesis In *Vibrio cholerae* . . . ", *J. Of Infectious Diseases*, vol. 129, No. 2, by Univ. of Chicago, Feb. 1974, pp. 117–123.

Guerrant, R. et al., "Cyclic Adenosine Monophosphate and Alteration Of Chinese Hamster Ovary Cell Morphology . . . ", *Infection & Immunity*, vol. 10, No. 2, Aug. 1974, pp. 320–327.

Gill, D., "Involvement of Nicotinamide Adenine Dinucleotide in the Action of Cholera Toxin In Vitro", *Proc. Nat. Acad. Sci. USA*, vol. 72, No. 6, Jun. 1975, pp. 2064–2068.

Southern, E., "Detection of Specific Sequences Amoung DNA Fragments Separated by Gel Electrophoresis", *J. Mol.* 98, (1975), pp. 503–517.

Noriki, H., "Evaluation of Toxoid Field Trial In The Philippines", *Symposium on Cholera Sapporo*, 1976, pp. 302–310.

Levine, M., "Immunity to Cholera as Evaluated In Volunteers", *Cholera and Related Diarrheas*, 43rd Symp., Stockholm, 1978, pp. 195–203.

Beringer, J. et al., "Transfer Of The Drug–Resistance Transposon Tn5 to Rhizobium", *Nature*, vol. 276, Dec. 7, 1978, pp. 633–634.

Johnson, S. et al., "*Vibrio cholerae* Hybrid Sex Factor That Contains Ampicillin Transposon Tn1", *J. Of Bacteriology*, Jan. 1979, pp. 531,536.

Honda, T. et al., "Selection And Characteristics Of A *Vibrio cholerae* Mutant . . . ", *Proc. Natl. Acad. Sci. USA*, vol. 76, No. 4, Apr. 1979, pp. 2052–2056.

Dallas, W. et al., "Cistrons Encoding *Escheria coli* Heat–Labile Toxin", J. Of Bacteriology, vol. 139, No. 3, Sep. 1979, pp. 850–858.

Chilton, M. et al., "Tailoring The Agrobacterium Ti Plasmid As a Vector For Plant Genetic Engineeering", *Stadler Symp.*, vol. 13, Univ. of Missouri, 1981, pp. 39–52.

Matzke, A. et al., "Site–Specific Insertion Of Genes Into T–DNA Of The Agrobacterium Tumor–Inducing Plasmid . . . ", *J. of Molecular and Applied Genetics*, vol. 1, No. 1, 1981, pp. 39–49.

Kaper, J. et al., "Molecular Characterization of Environmental and Nontoxigenic Strains of *Vibrio cholerae*", *Infection and Immunity*, vol. 32, No. 2, May 1981, pp. 661,667.

Sigel, S. et al., "Ability Of An Avirulent Mutant of *Vibrio cholerae* . . . ", *Infection and Immunity*, vol. 32, No. 2, May 1981, pp. 474–479.

Holmgren, J., "Actions Of Cholera Toxin And The Prevention And Treatment Of Cholera", *Nature*, vol. 292, Jul. 30, 1981, pp. 413–417.

Sublett, R. et al., "Transposon–Facilitated Recombination in Classical Biotypes Of *Vibrio cholerae*", *Infection and Immunity*, vol. 32, No. 3, Jun. 1981, pp. 1132–1138.

Thomson, J. et al., "Mutagenesis By Insertion Of Drug Resistance Transposon Tn7 Into A Vibrio Species", *J. Of Bacteriology*, vol. 148, No. 1, Oct. 1981, pp. 374–378.

Baudry, B. et al., "Cloning Of A Gene (zot) Encoding A New Toxin Produced By *Vibrio cholerae*", *Infection & Immunity*, vol. 60, No. 2, Feb. 1992, pp. 428–434.

Levine, M. et al., "Volunteer Studies In Development Of Vaccines Against Cholera . . . ", *Acute Enteric Infections In Children*, Elsevier/North–Holland Biomedical Press, 1981, pp. 443–459.

Gennaro, M. et al., "The Expression Of Biologically Active Toxin In *Escherichia coli*", *Nucleic Acids Research*, vol. 10, No. 16, 1982, pp. 4283–4290.

Mekalanos, J. et al., "Isolation Of Enterotoxin Structural Gene Delection Mutations In *Vibrio cholerae*", vol. 79, Jan. 1982, pp. 151–155.

Levine, M. et al., "Immunity Of Cholera In Man: Relative Role Of Antibacterial Versus Antitoxic Immunity", *Transactions Royal Soc. Of Tropical Medicine & Hygiene*, vol. 73, 1979, pp. 3–9.

Svennerholm, A. et al., "Intestinal Antibody Responses After Immunisation With Cholera B. Subunit", *The Lancet*, Feb. 6, 1982, pp. 305–308.

Finkelstein, M. et al., "Protection In Rabbits Induced By The Texas Star–SR Attenuated $A^{-B+}$ Mutant Candidate Live Oral Vaccine", Infection and Immunity, vol. 36, No. 1, Apr. 1982, pp. 221–226.

Pearson, G. et al., "Molecular Cloning Of *Vibrio cholerae* Enterotoxin Genes In *Escherichia coli* K–12", *Proc. Natl. Acad. Sci. USA*, vol. 79, May 1982, pp. 2976–2980.

Lee, C. et al., "Use Of Cloned Intl Genes of *Escherichia coli* To Introduce mtl Deletion Mutations Into the Chromosome", J. Of Bacteriology, vol. 153, No. 2, Feb. 1983, pp. 685–592.

Mekalanos, J., "Duplication and Amplification Of Toxin Genes In *Vibrio cholerae*", *Cell*, vol. 35, Nov. 1983, pp. 253–263.

Lockman, H. et al., "Nucleotide Sequence Analysis Of The A2 and B Subunits Of *Vibrio cholerae* Enterotoxin", *J. Of Biological Chemistry*, vol. 258, No. 22, Nov. 1983, pp. 13722–13726.

Levine, M. et al., "New Knowledge On Pathogenesis Of Bacterial Enteric Infections As Applied To Vaccine Development", *Microbiological Reviews*, vol. 47, No. 4, Dec. 1983, pp. 510–550.

Mekalanos, J. et al., "Cholera Toxin Genes: Nucleotide Sequence, Deletion Analysis And Vaccine Development", *Nature*, vol. 306, Dec. 8, 1983, pp. 551–557.

Svennerholm, A. et al., "Local And Systemic Antibody Responses And Immunological Memory In Humans . . . ", *Bulletin of World Health Org.*, vol. 62 (6), 1984, pp. 909–918.

Barrineau, P. et al., "The DNA Sequence Of The Mercury Resistance Operon of the IncFII Plasmid NR1", *J. of Molecular and Applied Genetics*, vol. 2, No. 6, 1984, pp. 253–261.

Sporecke, I. et al., "Genetic Mapping Of *Vibrio cholerae* Enterotoxin Structural Genes", *J. Of Bacteriology*, vol. 157, No. 1, Jan. 1984, pp. 253–261.

Levine, M. et al., "Evaluation In Humans Of Attenuated *Vibrio cholerae* El Tor Ogawa Strain Texas Star–SR . . . ", *Infection and Immunity*, vol. 43, No. 2, Feb. 1984, pp. 515–522.

Kaper, J. et al., "Recombinant Nontoxinogenic *Vibrio cholerae* Strains As Attenuated Cholera Vaccine Candidates", *Nature*, vol. 308, Apr. 12, 1984, pp. 655–658.

Lockman, H. et al., "*Vibrio cholerae* Enterotoxin Genes: Nucleotide Sequence Analysis of DNA . . . ", *J. Of Bacteriology*, vol. 159, No. 3, Sep. 1984, pp. 1086–1089.

Kaper, J. et al., "A Recombinant Live Oral Cholera Vaccine", *Bio/Technology*, Apr. 1984, pp. 345–349.

Kaper, J. et al., "Development And Testing Of A Recombinan Live Oral Cholera Vaccine", *Vaccines 85, Cold Spring Harbor Lab.*, pp. 107–111. (1985).

Brown, N. et al., "The Nucleotide Sequence Of the Mercuric Resistance Operons Of Plamd R100 and Transposon TN501 . . . ", *Mol Gen Genet*, 202, 1986, pp. 143–151.

Black, Robert. et al., "Protective Efficacy In Man Of Killed

Whole Vibrio Oral Cholera Vaccine . . . ", Infection & Immun., 1987, 23 pages.

Kaper, J. et al., "Recent Advances In Developing A Safe And Effective Live Oral Attenuated *Vibrio cholerae* Vaccine", *Advan. In Research on Cholera & Related Diarrheas*, 6, eds. 1988, pp. 161–167.

Levine, M. et al., "Volunteer Studies Of Deletion Mutants Of *Vibrio cholerae* O1 Prepared By Recombinant Techniques", *Infection & Immunity*, vol. 56, No. 1., Jan. 1988, pp. 161–167.

Rader, A. et al., "Nucleotide Sequences And Comparison Of The Hemolysin Determinants . . . ", *Infection & Immunity*, vol. 56, No. 6, Jun. 1988, pp. 1414–1419.

Levine, M. et al., "Safety, Immunogenicity, And Efficacy Of Recombinant Live Oral Cholera . . . ", *The Lancet*, Aug. 28, 1988, pp. 467–470.

Migasena, S. et al., "Preliminary Assessment Of The Safety And Immunogenicity Of Live Oral Cholera . . . ", *Infection & Immunity*, vol. 57, No. 1, Nov. 1989, pp. 3261–3264.

Galen, J. et al., "Cloning, Sequencing, and Expression Of The Gene, nanH, For *Vibrio cholerae* . . . ", *Advances In Research On Cholera and Related Diarrheas*, 7, 1990, pp. 143–153.

Brickman, T. et al., "Molecular Cloning And Nucleotide Sequence Analysis Of Cholera Toxin Genes . . . ", *Infection & Immunity*, vol. 58, No. 12, Dec. 1990, pp. 4142–4144.

Cryz, S. Jr. et al., "Randomized Double–Blind Placebo Controlled Trial To Evaluate The Safety . . . ", *Vaccine*, vol. 8, Dec. 1990, pp. 577–580.

Fasano, A. et al.; "*Vibrio cholerae* Produces A Second Enterotoxin, Which Affects Intestinal Tight Junctions", *Proc. Natl. Acad. Sci.*, USA, vol. 88, pp. 5242–5246, Jun. 1991.

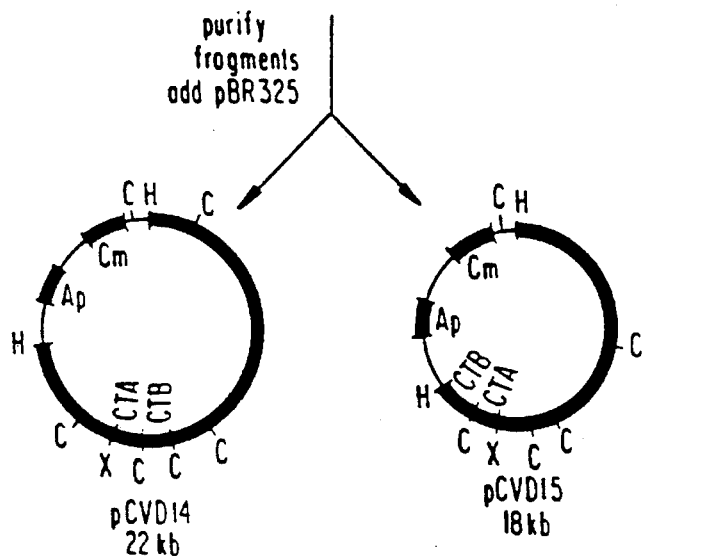
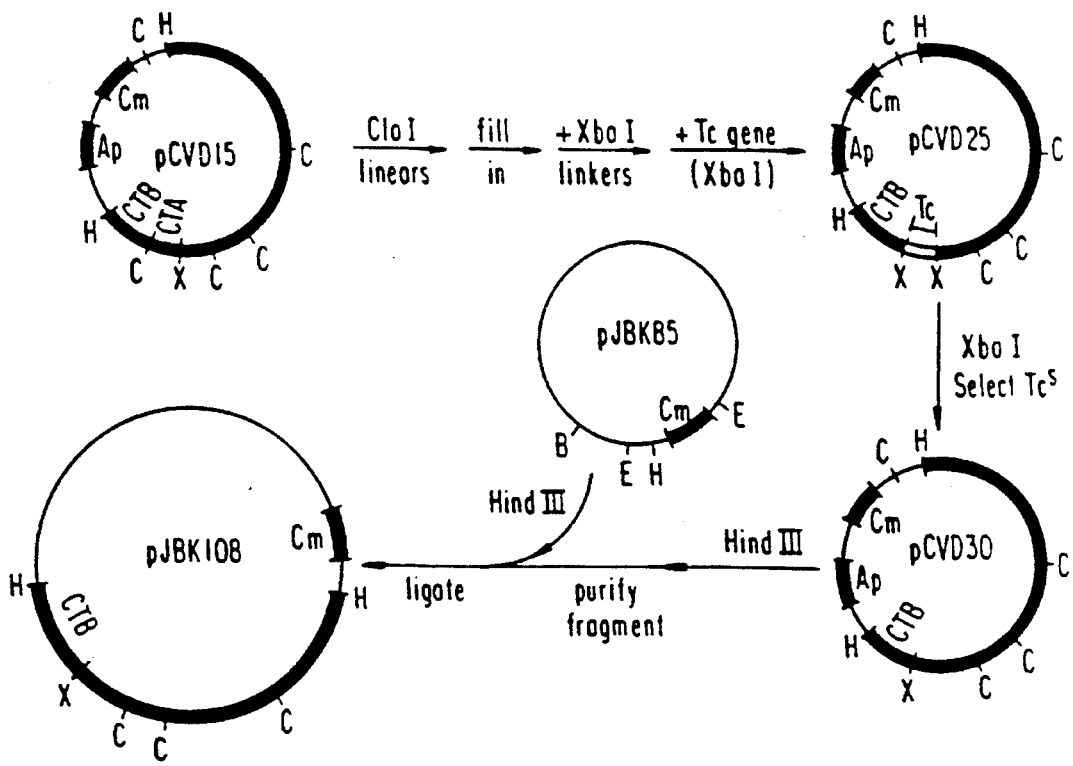

```
         A₁                              A₂
         Xbo I                           Cla I
         ___                             ___
GAT  TCT AGA  CCT                TCA TCG ATG  AGT
CTA  AGA TCT  GGA                AGT AGC TAC  TCA
ASP  SER ARG  PRO                SER SER MET  SER

A₁         A₂
              Xbo I
              ___
        GAT  TCT AGA  GCG ATG
        CTA  AGA TCT  CGC TAC
        ASP  SER ARG  ALA MET
```

| SAMPLE | N | MEAN | S.D. | P |
|---|---|---|---|---|
| 395 | 30 | 244.2 | 107.9 | 0.002 |
| MEDIUM | 14 | 373.7 | 129.0 | |
| CVD101 | 32 | 230.2 | 75.5 | 0.004 |
| MEDIUM | 30 | 305.8 | 96.3 | |
| 395N1 | 31 | 305.8 | 80.1 | 0.322 |
| MEDIUM | 31 | 289.1 | 83.8 | |

FIG. 15C

```
  1   ATACAGCGGGCTTTCTGTTCTTTTTAGGGTTAGACCAAGGCGCTGGCTATCGTGCTTCAGGC
                                        M  S  I  F  I  H  H  G
      TTTGATGACCCGTTCGCCCTGCCGAGCGTTAAACCTATGAGTATCTTTATTCATCACGGC  120

A  P  G  S  Y  K  T  S  G  A  L  N  L  R  L  L  P  A  I  K
 121  GCGGCCAGGCTCTTATAAAACGTCCGGGCATTATGGCTTGCGTCTGCTGCCGGCGATTAAG  240

S  G  R  H  I  T  N  V  R  G  L  N  L  E  R  I  A  K  Y
 241  TCAGGCCGTCACATCATCACGAATGTGCGAGGCTTAAACCTTGAACGCATAGCTAAGTAC

L  K  M  D  V  S  D  I  S  E  F  I  D  T  D  H  P  D  G
      TTAAAAATGGACGTCTCAGACATCGAGTTTATTGATACAGACCATCCAGACGGT  360

R  L  T  M  A  R  F  W  H  W  A  R  K  D  A  F  L  F  I  D
 361  CGCTTAACGATGGCGCGGTTTTGGCACTGGGCGGAGAAAGGACGCGTTTCTCTTTATTGAT

E  C  G  R  I  N  P  P  R  L  T  A  T  N  L  K  A  L  D  T
      GAATGTGGTCGCATCTGGCCGCCGAGACTGACGGCCACCAATTTAAAGGCGCTCGACACG  480

P  P  D  L  V  A  E  D  R  P  E  S  P  E  V  A  F  D  M  H
 481  CCGCCGGATTTGGTCGCAGAGGATAGGCCTGAGAGCTTTGAGGTCGCTTTTGACATGCAT

R  H  G  W  D  I  C  L  T  P  N  I  A  K  V  H  N  M
      CGTCACCACGGCTGGGATATCTGCCTAACCACGCCTAACATTGCCAAGTGCACAACATG  600

I  R  E  A  E  I  G  Y  R  H  F  N  R  A  T  V  G  L  G
 601  ATAAGAGAGGCGGAGATAGGCTATCGCCACTTTAACCGCGCCACGGTGGGGCTAGGG

A  K  F  T  L  T  L  H  D  A  A  N  S  G  Q  M  D  S  H  A
      GCAAAGTTTACCCTGACCACCCTGGACCTCTGGACAGATGGATTCGCACGCG  720

L  T  R  Q  V  K  K  I  P  S  I  F  K  M  Y  A  S  T
 721  CTGACACGCCAAGTCAAAAAAATTCCAAGTCCGATTTTTAAGATGTACGCAAGCACCACC
```

FIG.18A

```
        T  G  K  A  R  D  T  M  A  G  T  A  L  W  K  D  R  K  I  L
 721    ACAGGCAAAGCACGGGACACGGATGGCCGGAACGGCTGTGGAAAGACAGAAAGATCCTT

F  L  F  G  M  V  F  L  M  F  S  Y  S  F  Y  G  L  H  D  N
 841    TTCTTGTTCGGCATGGTTTTTTGATGTTCTCTTATTCGTTTACGGCCTTACACGACAAT    840

P  I  F  T  G  G  N  D  A  T  I  E  S  E  Q  S  H  P  Q  S
        CCAATTTTTACAGGGGGAAATGATGCAACTATCGAGTCAGAGCAATCCGAGCCTCAGTCA    960

K  A  T  A  G  N  A  V  G  S  K  A  A  P  A  S  F  G  F
 961    AAGGCTACTGCTGGGAATGCTGTCGGGAGCAAGGCGGCTCCTGCTTCTTTTGGTTTT

C  I  G  R  L  C  V  Q  D  G  F  V  T  V  G  D  E  R  Y  R
        TGTATTGGTCGGCTTTGTGTCCAAGATGGTTTTGTCACTGTTGGTGATGAGCGTTATCGC    1080

L  V  D  N  L  D  I  P  Y  R  G  L  W  A  T  G  H  H  I  Y
 1081   CTCGTAGACAACAATTGGACATTCCTTATCGTGGTCTATGGGCGACAGGTCATCACATTAC

K  D  L  T  V  F  F  E  T  E  S  G  S  V  P  T  E  L  F
        AAGGATCTTACAGTGTTTTTTGAAACCGAGAGTGGCAGCGTCCCAACAGAGCTGTTT    1200

A  S  S  Y  R  Y  K  L  Y  L  P  L  P  D  F  N  H  F  V  V  F
 1201   GCATCGAGTTACCGCTACAAGGTGCTACCGGTTACCGGATTTCAATCACTTTGTGGTGTTC

D  T  F  A  A  Q  A  L  W  V  E  V  K  R  G  L  P  I  K  T
        GATACCTTTGCAGCGGCAAGGCGCTGTGGGTAGAAGTGAAACGGGGTTTACGGATAAAAACA    1320

E  N  D  K  K  G  L  N  S  I  F  *
 1321   GAAAATGATAAAAAAGGACTAAATAGTATATTTGATTTTTGATTTTTGATTTTTGATTT

TTGATTTTTGATTTTTGATTTTGATTTCAAATAATACAAATTTATTTACTTATTTAATT
        GTTTTGATCAATTATTTTCTGTAAACAAAGGGAGCATTATATGGTA    1428
```

FIG. 18B

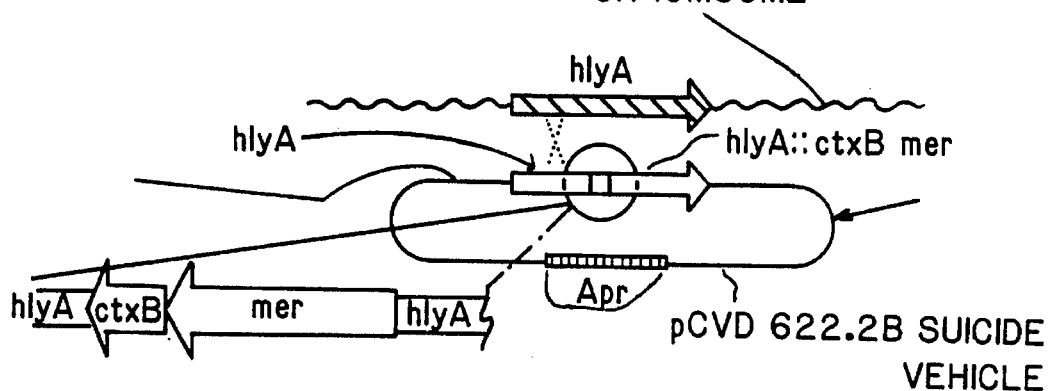
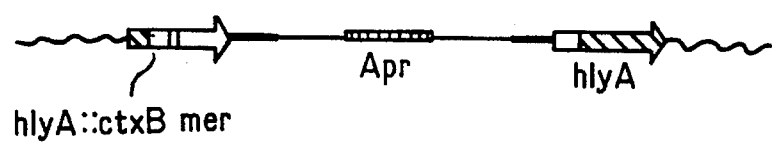
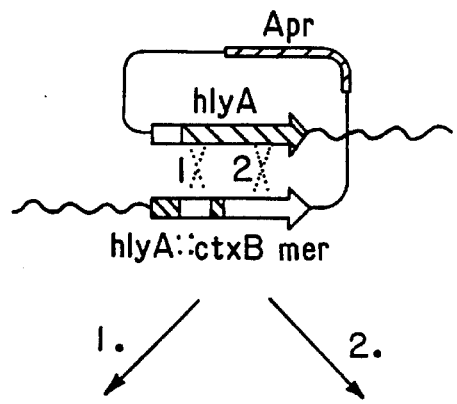
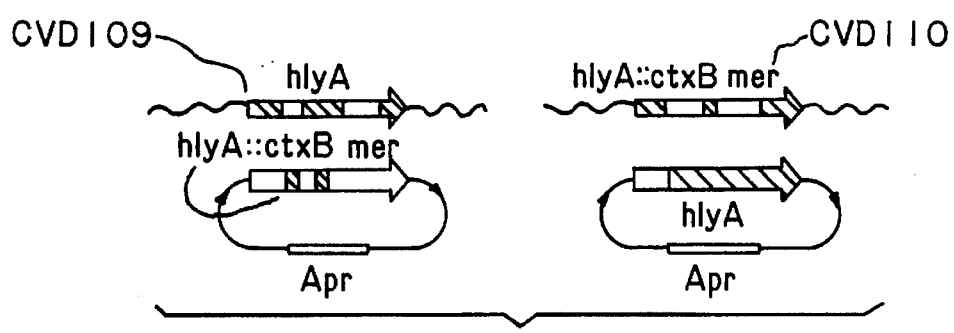
FIG.20

ATGCCAAAACTCAATCGTTGCGCAATCGCGATATTCACAATATTAAGCGCAATATCCAGT
CCAACCCTGTTGGCAAATATCAATGAACCAAGTGGTGAAGCGGCGGATATTATTAGTCAA
GTCGCTGATAGTCATGCAATAAAATATTACAATGCTGCTGATTGGCAAGCCGAAGACAAC
GCATTACCGAGCTTAGCTGAGCTGCGCGATTTGGTGATTAACCAGCAAAAACGCGTTTTG
GTTGATTTCAGTCAGATCAGTGATGCTGAAGGTCAAGCAGAGATGCAAGCCCAATTCAGA
AAGGCTTATGGGGTGGGTTTTGCTAATCAATTTATTGTCATCAGTGAACATAAAGGGGAA
CTGCTGTTTACACCTTTTGATCAGGCAGAAGAGGTTGACCCTCAATTACTCGAAGCGCCG
CGTACCGCTCGCTTATTAGCGCGCTCTGGTTTTGCAAGTCCGGCACCGGCAAACAGCGAA
ACAAATACCTTGCCGCATGTGGCTTTTTACATCAGTGTCAACCGTGCGATCAGCGATGAA
GAGTGTACCTTTAACAACTCTTGGTTGTGGAAAAACGAAAAGGGCAGTCGTCCGTTCTGT
AAAGATGCCAATATCTCATTGATTTATCGAGTTGGGTACCCCGTCAGTGCTGGCGCAATG
GTACTGACGACTGCCCCTCAACATAATGCCGCGCCACATAATACGCACTAAGGATGTGGA
ATAAAAACATCATACTTGCAGTAATACATGTTTGGGCAAAACGGTTGCTTCTCATCATCG
AACCACAAAAAGCCCACTGAGGTGGGCTTTTTATATCTTAATTTGCCATACTAATTGCG
GCAATCGCATGAGGCGTTTTATTATTCCATACACATAACTTTTCGACTTTAGCTTCAGTA
AGATATGCAATCCTCAGGGTATCCTTCATCCTTTCAATCGCTTTTTTTGTGAATCTATA
TGTTGACTACTTGGTACTTCTACTTGAAAAATTGCACCATTCTTAAAAGTAATGATAGCC
ATCTCTCTTTTTCCAGCTAGAGATTCTGTATACGAAAATATCTTATCATTTAGCGTATAT
ATTTGTGTGTTGTGTGATTCTGCACACAAATCAGTAATATTTTGAGGTGTTCCATGTGCA
TATGCTGAAGATAGTAAAACTGTAAAAAAAACACCAAATTTTAATTTAATCATAATTCAT
CCTTAATTCTATTATGTGTATCAATATCAGATTGATAGCCTGAAAATATTTGTCTTTTAA
CTTTAGATTGGTATTCGTCAAGGAATTTTACACCTAGACTTTGGGTTTTTTCATCGCAAG
TATTACTGATCGCTCTAGAATCTGCCCGATATAACTTATCATCATTTGCATATGAAAATG
ATGATAAGAAAATAAAAAACACAAATATTATCTTTACCATATAATGCTCCCTTTGTTTAA
CAGAAAAATAATTGATCAAAACAATTAAATAAGTAAATAAATTTGTATTATTTGAAATCA
AAAATCAAAATCAAAATATACTATTTAGTCCTTTTTTATCATTTTCTGTTTTTATCGGT
AAACCCCGTTTCACTTCTACCCACAGCCTTGCGGGGTACCCCCCTCGCCCAGCACCCACG
CGCCTATTTCCGGCATCAGGCCGAACGACTCGGCCAGCGGCAGGAACTGGCCGGGCGGCA
ACAGGCCAAGCCTCGGATGCCGCCAGCGCATCAACGCTTCCGCGCCGACAGTCCGGTGAT
CGCGCAGATCGACCAGCGGCTGGTAATGCAGGTCAAGCTGTCCGCGCGCCGCCGCCTGCG
CCAACTCGGCCGCCGTCCATCCGGCGGGCTGCGAACTCGTCATGATCCGCCCCGGAAGGC
GCGCAGCAGCCGCGTTACGGCCAGAACGAACAAGCCGGTCAGCGCGAGCGCGGCAACACC
CCAATGCTCGCCAAGGAAGGCACCGGCGGTCGTCCCGGCCAGCACGGCGGCGAGAATCGG
CAGATGGCAGGGCAGGTCAACACGGCCAGCGCACCCCACAGGTAGCCGGAAACGGGTTG
```

FIG.21A

```
GCGCGTCTCGGGCGGCAGTTTGTCAGGGGCGTTCACGGCAATGCCTCCTCGTGCGCCCGC
TCGGCTGGCATGGAGGCCAGTTGCGCGTCCAGATGGGCCAACGCCGCGCGCCGCCGCTCG
ACCAACTGGCGCAGACGGCAAGCTGCGCTGCGGCTTGTGCGCCGTCCGCTGCGTCGAGCG
CACGGCACAGCCGCGCCAGGGCATCCAGGCCGATACCCGCCTCGAAGGCCGCGCGCACGA
AGCACAGCCGTTGCAAGGCCGCATCGTCGAACACGCCGTAGCCGCCCGTGGTGCAGGCCA
CCGGCCGTAACAAGCCGCGCACCAGGTAGTCGCGCACGATATGTACGCTCACCCCAGCGT
TATGGGCCAGTTGCGATACCGTGTAGGCGCTCATCGCACACCTCCTTGTCCTCACCCGGC
GCAGCAGGAAAGCTGCTTCACATCCTTGTTGAAGGTCTGCGCCGCGAGCTTCAACCCTTC
GACCATCGTCAGGTAGGGGAACAACTGGTCGGCCAGTTCCTGCACCGTCATCCGGTTGCG
AATCGCCAGTGCGGCCGTCTGGATCAGTTCGCCCGCTTCCGGGGCCACTGCCTGCACGCC
GATCAGTCGTCCGCTGCCTTCTTCAACCACCAGTTTGATGAAGCCGCGCGTGTCGAAGTT
GGCGAGCGCGCGCGGCACGTTGTCCAGCGTTAGCGTGCGACTATCAGTTTTGATGCCGTC
ATGGTGCGCTTCCGCCTCGCTGTAGCCTACGGTCGCCACTTGCGGGTCGGTGAACACCAC
GGCCGGCATCGCGGTCAGGTTCAGGGCCGCGTCACCGCCGGTCATGTTGATCGCGGCGCG
AGTGCCGGCCGCTGCCGCCACATAGACGAACTGCGGCTGGTCGGTGCAGTCGCCTGCGGC
GTAGATGTGTTCCACGCTTGTACGCATGCCGGGGTCGATGACGATAGCGCCTTGCGGGGT
GAGCGTGACGCCCGTCGCATCCAGTGCCAGCTTGCGTGTGTTGGGCGCGCGGCCGGTGGC
GACCAGCAGCTTGTCGGCGCGCAGTTCGCCGTGCGCCGTGGTGAGCACGAATTCGCCGTC
CCCTTCACCATTGATATACGCGACCTGGCTGGCCTGGGTGTGTTCCCTCACCTCGATGCC
CTCCATGCGGAATGCGGCCGTGACAGCTTCGCCTATAGCTGGGTCTTCGCGGAAGAACAG
CGTGCTGCGAGCCAGGATCGTCACCTTCGCTCCGAGTCGGGCGAACGCCTGCGCCAGCTC
CAGCGCCACCACTGATGAGCCAATCACGGCCAGGCGCTTAGGAATCGTCTCGCTGACCAG
CGCTTCAGTGGAAGTCCAGTACGGAGTGTCTTTCAGGCCGGGAATCGGCGGCACGGCCGG
GCTCGCGCCGGTGGCGATCAGGCAGCGGTCGAATGCCACCACGCGCTCGCCGCCGTCGTT
GAGTTGCACGATCAGGTTGCGATTGTCCTTAAAGCGGGCGGAGCCGTGCAGCACAGTGAT
CGCCGGATTGCCCTCCAAGATGCCTTCGTACTTGGCGTGGCGCAGTTCATCGACGCGGGC
CTGCTGCTGGGCCAGCAGCGCCGTGCGCTGGATGGTCGGCGTGGTAGCGGCGATGCCGCC
ATCGAACGGGCTTTCCCGGCGCAGATGGGCGATATGGGCGGCGCGGATCATGATCTTGGA
CGGCACACAACCGACATTGACGCAGGTGCCGCCGATGGTGCCGCGCTCGATCAGCGTGAC
ACGTGCGCCTTGCTCGACGGCCTTCAGCGCCGCTGCCATCGCGGCCCCGCCGCTGCCGAT
GACGGCGATATGCAATGCGCCGCTGCTACCCGTCTTGTCGTTTCTGCCCAGCAGATCGCG
CATCTTGTCGAGCAATCCGCCCGGCGTCGAAACTGAGGCGGCATCGGCCAGCGTGGCCCG
ATAACCGAGTCCAGCTACAGCGGCCGTCAGCGCGTCGGGTGACGTGCCCACCTCAATGGC
GAGCTTGGCGCTGCCCTTGGCGTAGGAGACATCCGCTGATTGCACGCCGGGCACTTTCTC
```

FIG. 21B

```
CAGGGCGTCCTTGACATGCACTGCGCACGAGTCGCAAGTCATGCCGGTGATTTTGAGAGT
GCTCATACCATCGTTCCTTATTCGTGTGGGCCGCCGTGTCGCACGGTCAGCCGTCTTTCA
CAAGCGCTTGGCGGGGAGTTCGCAGCCGTCCGGTCCGCAACGGCGATGCGCCGGCGACAC
GAAGTCCAGATCGACACCCCAATCATCAAGGCCAGGCCGACGTACATCAGGTTCGCCGT
CCACCAGTTGCCGAGCAGCCAGACCGTGGCCGCAAACACGATGGCCGGGCCGATCATGCC
GAGCAGACTGCGCAGCCATTGCCGATGACTGAACCAACCCAGCGCGTTCGCCAGGAAGGC
CAGCGCGGCAAACAGCGGCAGCAGGCGGCTGATGAACAGTCCCTCGTACTGGCTCAAGAA
GCCCAGCCCGATGGCCGCGCCGAAGCTGGCGAGGGCTGGAAAGCAGGCGGCGCAGCCCAT
CGCGGAAACGACGCTGCCGAGCGCGCCGGTTTTATCGGCAATGCGTGTCATCAGTCCCAT
GAAGCGGCTCTCGCTGTTGTCGTTGGCTTGCTGGCTCACTGCTTGACGCTGGACGGATAG
CCGGCGTCTGCGGTGGCCTTGGTCAGCTTCTGTACGCTGGCCTTGGTGTCGTCAAAAGTG
ACGACGGCCTCGCGCTTCTCGAAGCCCACATCGACCTTCGTCACGCCTTCGACCTTGGAG
AGCGCTTTCTTGACTGTGATCGGGCAGGCGGCGCAAGTCATGCCGGGAACCGCTAGCGTG
ACGGTCTGGGTAGCGGCCCACACCGGGGCAACAGCGGCGGCGAGGGCAAGGGAGGCAAAC
AGTTTCTTCATGATGAACTCCTGGTTAATAGAAAAATGGAACGACATAGGGAAATCCAAG
CGCGACCAGGACCAGCACGGCCACGATCCAGAAAATCAGCTTGTAGGTGGCGCGCACCTG
CGGAATCGCGCAGACCTCACCTGGCTTGCATGCCTGCACGGGCCGGTAAATCCGCTTCCA
GGCGAAGAACAGCGCCACTAGCGCCGCGCCGATGAACAACGGTCGATAGGGTTCCAGCAC
CGTCAGGTTGCCGATCCAAGCACCGGAGAAGCCCAGGGCGACCAGTACTAGCGGCCCCAG
GCAGCAGGTCGATGCAAGAATGGCGGCCAGCCCGCCGGCGAAGAGCGCACCGCGCCCGTT
TTGTGGTTCAGACATACGTTGGCCCTTTTGAATTTGGATTGGATAGCGTAACCTTACTTC
CGTACTCATGTACGGAGTCAAGCGATATGGAAATAATTTGGAAAACCTGACCATTGGCG
TTTTTGCCAAGGCGGCCGGGGTCAACGTGGAGACAATCCGCTTCTATCAGCGCAAGGGCC
TGTTGCGGGAACCGGACAAGCCTTACGGCAGCATCCGCCGCTATGGGGAGGCGGACGTGG
TTCGGGTGAAATTCGTGAAATCGGCACAGCGGCTGGGGTTCAGTCTGGACGAGATTGCCG
AGCTGTTGCGGCTCGACGATGGCACCCACTGCGAGGAGGCCAGCAGCCTGGCCGAACACA
AGCTCAAGGACGTGCGCGAGAAGATGGCCGACTTGGCGCGCATGGAAACCGTGCTGTCTG
AACTCGTGTGCGCCTGCCATGCACGAAAGGGGAATGTTTCCTGCCCGTTGATCGCGTCAC
TACAGGGCGAAGCAGGCCTGGCAAGGTCAGCTATGCCTTAGCGTGCTTTATTTTCCGTTT
TCTGAGGTGCCCCCTAATAGTGTTCTTCCATTTCGGTAAAAATCCCTACCATGGGGTACC
CAACCTACAACACACAAGACTATCGTATTGAGCGTAATGCGAAGAATGCGCAAGCGGTTA
GCTTTACATGGAATCGTCAACAATACGCGACAGCAGAATCGCTACTCAATCGTTCGACCG
ATGCTTTGTGGGTGAATACCTACCCGGTAGATGTAAACCGTATTAGCCCGCTGAGCTACG
CGAGTTTTGTGCCGAAAATGGATGTGATTTATAAAGCCTCAGCCACAGAGACAGGCAGTA
```

FIG. 21C

CGGATTTTATCATCGACTCTTCGGTCAATATCCGCCCAATCTATAACGGTGCTTATAAGC
ACTACTATGTGGTCGGTGCTCATCAATCCTACCATGGCTTTGAAGATACCCCACGTCGTC
GAATCACGAAATCGGCAAGCTTTACGGTCGATTGGGATCACCCAGTATTCACGGGTGGCC
GCCCGGTCAACCTACAACTTGCCAGCTTTAACAACCGCTGTATTCAAGTCGATGCTCAAG
GTCGCTTGGCGGCCAATACGTGCGATAGCCAGCAATCAGCGCAATCGTTCATCTATGATC
AGCTTGGTCGATATGTGAGTGCGAGTAACACCAAGCTCTGTCTTGATGGTGAGGCATTAG
ACGCATTGCAACCCTGTAACCAAAACCTGACTCAGCGTTGGGAGTGGCGTAAAAGCACAG
ATGAATTGACCAATGTCTACAGCGGCGAGTCCCTTGGACATGACAAACAAACCGGTGAGC
TTGGTTTGTATGCGAGCAGCAACGATGCGGTAAGTTTACGTACCATCACCGCTTATACCG
ATGTGTTTAATGCGCAAGAAAGTTCGCCGATTCTGGGTTACACACAAGGGAAAATGAATC
AGCAGCGTGTGGGACAAGATCATCGTTTGTATGTGCGAGCGGGTGCTGCCATTGATGCAT
TAGGGTCCGCCTCCGATTTATTGGTTGGTGGCAATGGTGGTAGCTTGAGTTCGGTGGATC
TGTCCGGCGTCAAATCCATCACGGCAACCTCTGGTGATTTCCAATATGGCGGTCAGCAGT
TGGTGGCGCTGACATTCACCTACCAAGATGGACGTCAGCAAACGGTAGGCTCGAAAGCGT
ATGTCACCAATGCTCATGAAGACCGTTTCGATTTACCGGCTGCCGCTAAGATCACTCAAC
TGAAAATTTGGTCTGACGATTGGTTGGTGAAAGGGGTTCAATTTGATTTGAACTAA 7076

FIG. 21D

```
  1  GATATCCACTCACGGCATTAAGTGGGCTCGTCGTCAGGTCGGTAAGACGTTGTTTGATATT
                A
 61  TCAAAGCATTTTGGTGGGTGATTTGGAAAGGGTGTTTGGGCGTTGATTTCTAAGGAAATT   120

121  CACGACGATTCACTCAACCTTCCAGATTCTTATATGAAGTTAATTGATGAAATTATGGGT   180

181  GATTAATATGAAATCTCGTTTGTTTTTGGTGCCTCTCATTCTGAAGGGTG---AG        240
                                                        AGT
241  TAAGACTGGTGCTCCTTACCTTATCCCAGTGCTTTTTGTTGGTAAGCCGATTCGCCAGTG   300
                      A   T
301  GAAAAACGATAAAGGCCAATGTTTGACGTTTGGCTTGCAGCATCAGGAAGTGAAATTTGT   360

361  ATCCAGTGACGGCGATGACCAGAAAACTCGAACAGACCCGCCTTTCCGGTTCTTGTCACGTT 420

421  TGACAATGAGCCAGACCCAGAAGACCCATCGCGTAACCTCGTGATTGATTATCAAGTGGT   480
                                            A    C
481  GTGTTCCTTGTTTGACAACGTGCCGGGCGCAAGCCATTGGATAAACCTCAACCCATTAAA   540

541  TCTTGATGGACTTAACCCATTATGTCTGGAGCGAGGCGCTCTATTTCGCGGTGGTCAAGG   600
                                    A
```

FIG.24A

```
601  CCGTTCTCGTTCTGTTCTTTACATCCTTTGGGATTGGCGCGGTTGCCAGTCTCATTTTAT   660
                                                    T
661  CCACGGTAAAGGAGAAGCTACATGTTTAGCTCACTGAAAACAAACTTAATACCTTTAAA    720
721  AGCACCCTTTCACTCGGGGGTTTTCTTGCTGTTTCCGCATTTGCTAACCAAGCACTCGCG   780
            G
781  GCTGCTGATACGGGTTTGGTCGCGGAAGTCACCAAAACACTGGGCACCAGTAAAGATACG   840
              G                 A
841  GTGATTGCGCTTGGGCCCGCTTATCATGGCCGTGGGAGCAATTGTTCTGATTGTTACC    900
                              C                            G
901  GTGATTGGCTTAATTCGTAAGGCTAAATAGTGCTTGAGTTGTGGCTGGGTCTCTTTGGCT   960
961  CAGCGGTCATCATTATCGGCTTTGTCGGGCTTATATTTGGTTTAAGGGAGGAGGGCGA    1020
                         M  R  Y  F  L  L  F  L  T  L  L  F  L  S  P
1021 GCGTTCGCCCCTTTTTTATGCGCTATTTCTACTGTTTTGACATTGCTCTTTCTTTCTCC   1080
      S  V  T  A  S  S  I  N  C  D  P  N  T  T  S  H  Q  L  L
1081 ATCGGTAACAGCTTCCTCCATCAATTGTGATCCTAATACTACTAGCGTCACCAGTTACT   1140
                G                                  G
      F  G  F  G  S  P  I  V  Q  S  V  L  F  D  G  C  M  L  D  I
1141 TTTCGGTTTTGGCTCTCCCATTGTGCAATCGGTGTTATTTGATGGCTGCATGCTTGATAT  1200
```

FIG.24B

```
        E  K  D  D  Y  G  F  V  W  S  C  L  S  N  E  N  G  D  Y  C
1201    TGAAAAAGATGACTATGGTTTTGTTTGTTCTTGTCTCTCAAATGAAAATGGGACTATTG    1260

K  G  L  Y  K  P  R  F  T  Q  G  V  S  P  N  W  P  M  C  D
1261    CAAGGGGCTCTACAAACCCCGTTTTACACAAGGGGTGTCCCCGAACTGGCCGATGTGCGA    1320
                                  T                       A

L  S  G  A  S  A  E  R  C  I  Y  P  Y  C  P  E  G  E  E  C
1321    CTTGTCCGGAGCATCTGCAGAGAGGCGCTGCATTTATCCTTATGCCCTGAGGGGAAGAGTG    1380

V  P  L  P  P  S  P  P  S  D  S  P  V  D  G  L  S  S  S  F
1381    CGTTCCCCTTACCACCTTCACCGCCCAGTGATTCCCCTGTTGATGGGCTGAGCAGCTCGTT    1440

K  S  A  F  N  Q  V  Y  K  N  Q  S  E  M  A  S  T  L  N  H
1441    TAAGTCTGCGTTCAATCAGGTCTATAAAAACCAATCAGAGATGGCTTCGACTCTCAATCA    1500

V  S  G  Q  V  S  H  S  Q  D  M  V  Q  L  N  T  K  F  H  A
1501    TGTCAGTGGTCAGGTGTCCCACTCTCAAGATATGGTTCAGCTCAATACGAAGTTTCACGC    1560

D  R  V  L  E  K  V  N  A  I  N  N  R  L  N  G  Q  I  N  Y
1561    GGACCGTGTTCTTGAAAAAGTGAACGCCAATCAATCGATTGAATGGGCAGATAAACTA    1620
              T          GG    C    C  G        T   GG    A  GG  G

L  E  E  V  R  I  D  V  W  D  T  Q  R  E  V  R  K  A  K  D
1621    TCTTGAAGAAGTTCGCATCGATGTATGGGATACACAACGGGAGGTCAGAAAAGCCAAGGA    1680
                               G                T     T  G           
                               A                    C                
```

FIG.24C

```
          E  L  S  S  R  V  G  S  V  A  H  D  V  Y  Q  S  K  N  A  V
1681    TGAACTCTCTTCACGTGTTGGTGTTCTGTTGCACGATGTTTACCAAAGTAAGAATGCTGT    1740
                       G   T AC  T        CGG    T    T         GCTTT  T  CG   CT AA

L  R  A  I  D  E  L  K  D  S  L  G  G  V  V  P  P  N  P
1741    GCTTCGGGGCGATTGATGAGCTTAAAGATTCACTCGGTGGGGTTGTCGTTCCGCCTAACCC    1800
            C                                                       AC

D  Q  P  N  P  T  P  P  D  S  S  S  P  N  Y  T  G  A  L  N
1801    AGACCAACCCAATCCCACGCCACCCGATAGCAGCAGCCCCCAATTATACAGGGGCGCTTAA    1860

T  I  S  K  K  L  N  T  L  E  T  I  S  Q  Q  L  D  T  M  N
1861    TACCATCTCTAAAAAAGCTCAATACCTTAGAGACGATTTCACAGCAACTCGACACCATGAA    1920

T  A  L  S  G  R  C  S  N  P  A  R  C  Q  F  P  I  R  E  A
1921    CACGGGCGCTATCAGGGGCGCTGTAGTAACCCTGCTCGTCAGTTTCCGATACGCGAGGC    1980
                                                                 AA                                    A

E  T  E  L  E  T  A  Q  Q  N  L  K  Q  M  I  N  D  K  I  T
1981    CGAGACCGAGTTAGAAACGGCTCAGCAGAATTAAAGCAGATGATCAACGATAAAATCAC    2040
                                                                          G

Q  S  A  L  H  Q  F  K  G  S  A  A  V  P  S  F  C  S  Y  V
2041    CCAGTCGGCTTTGCATCAGTTCAAAGGCTCGGCGGCGGTGCCTTCGTTTGCTCCTATGT    2100

E  F  G  Y  N  L  C  F  D  F  S  L  F  S  E  N  L  H  I
2101    CGAGGAGTTTGGTTACAACCTCTGTTTTGACTTCTCCCTCTTTTCTGAAAACCTGCACAT    2160
                     C
```

FIG. 24D

```
           I  R  M  I  V  L  A  M  A  Y  I  L  A  A  M  L  I  L  F  R
2161    CATCCGCATGATAGTGCTCGCGATGGCGTACATTCTGGCCGCCATGCTCATTTTGTTTAG              2220

M  L  M  M  D  P  L  Y  D  W  L  I  D  G  F  T  W  L  V
2221    GTGATGCTTATGATGGACCCCTTATGACTGGCTAATTGATGGCTTTACGTGGCTTGTG                2280
                                A

I  K  L  G  I  M  W  I  E  S  K  I  F  V  I  Q  F  F  W  E
2281    ATCAAGCTCGGTATTATGTGGATTGAGAGCAAGATTTTTGTCATCCAATTCTTCTGGGAG              2340
                                                    T

M  S  Q  K  V  I  D  M  F  T  I  Y  P  L  I  Q  Q  A  I  D
2341    ATGTCCCAGAAAGTGATTGATATGTTTACCATCTATCCGCTTATCCAACAGGCTATCGAT              2400

M  L  S  P  Q  Y  S  G  F  L  F  F  L  G  L  D  Q  A  L  A
2401    ATGCTGTCTCCTCAATACAGCGGGCTTTCTGTTCTTTTTAGGTTAGACCAAGCGCTGGCT              2460
                        C

I  V  L  Q  A  L  M  T  R  F  A  L  R  A  L  N  L
2461    ATCGTGCTTCAGGCTTGATGACCCGTTTCGCCCTGCGAGCGTTAAACCTATGAGTATCT                2520
                                                T

2521    TTATTCATCACGGCGCCAGGCTCTTATAAAACGTCCGGGCATTATGGCTTCGTCTGC                  2580
                                                        A

2581    TGCCGGCGATTAAGTCAGGCCGTCACATCATCACGAATGTGCGAGGCTTAAACCTTGAAC              2640

2641    GCATAGCTAAGTACTTAAAAATGGACGTCTCAGACATCAGTATCGAGTTTATTGATACAG              2700
            G                                       T   G
```

FIG.24E

```
2701    ACCATCCAGACGGTCGCTTAACGATGGGCGCGTTTTTGGCACTGGGCGAGAAAGGACGCGT    2760
                 T
2761    TTCTCTTTATTGATGAATGTGGTCGCATCTGGCCCGCCCGAGACTGACGGCCACCAATTTAA    2820
                     C                                         T
2821    AGGCGCTCGACACGCCCGGATTTGGTCGCAGAGGATAGGCCTGAGAGCTTTGAGGTGG    2880
2881    CTTTTGACATGCATCGTCACCACGGCTGGGATATC    2915
```

FIG.24F

METHOD OF ISOLATING RESTRICTION FRAGMENT DELETIONS IN *VIBRIO CHOLERAE*, AND PRODUCTS THEREOF

This application is a continuation-in-part of applicants' U.S. patent application No. 07/821,872, filed Jan. 16th, 1992, now abandoned, which is a continuation of applicants' U.S. patent application No. 07/533,315, filed Jun. 5th, 1990, now abandoned, which are incorporated herein by reference. U.S. patent application No. 07/533,315 is a continuation-in-part of applicants' U.S. patent application No. 06/581,406 filed Feb. 17th, 1984, issued as U.S. Pat. No. 5,135,862, on Aug. 4th, 1992, which is a continuation-in-part of U.S. patent application No. 06/472,276, filed Mar. 4th, 1983, now abandoned, which are incorporated herein by reference. U.S. patent application No. 07/533,315 is also a continuation-in-part of applicant's U.S. patent application No. 07/363,383, filed Jun. 5th, 1989 and issued as U.S. Pat. No. 4,935,364, on Jun. 19th, 1990 which is a continuation of U.S. patent application No. 06/867,633, filed May 27th, 1986, now abandoned, which is a continuation of U.S. patent application No. 06/472,276, filed Mar. 4th, 1983, now abandoned, which are incorporated herein by reference. The research outlined in this application was supported by the National Institute of Health and in part by the Medical Biotechnology Center of the Maryland Biotechnology Institute.

BACKGROUND OF THE INVENTION

*Vibrio cholerae* (*V. cholerae*) is a non-invasive enteropathogen of the small bowel that does not penetrate the mucosal surface. Local SIgA mediated immunity at the mucosal surface is therefore implicated as a protective mechanism. Pathogenic *V. cholerae* 01 elaborate a protein enterotoxin (also know as cholera enterotoxin, or choleragen, or cholera toxin) which is responsible for induction of copious secretion by the intestine resulting in watery diarrhea, the clinical consequence of cholera infection. The genes responsible for cholera toxin are the ctx genes (also known as the tox genes). Cholera diarrhea can be extraordinarily severe and result in loss of so much body water and salts that dehydration, acidosis, shock, and death ensue without prompt therapy. Applicants have discovered that a second enterotoxin is produced by *V. cholerae* called zonula occludens toxin, reported in Fasano et al, *Vibrio cholerae Produces a Second enterotoxin Which Affects Intestinal Tight Junctions*, Proc. Nat. Acad. Sci. (USA) 88, 5242–5246 (1991). Further, there is a region of the chromosome containing the ctx genes which contains multiple copies of a 2700 base pair sequence called RS1 (for repetitive sequence). Mekalanos, *Cell* 35, 253–263 (1983).

The cholera vaccines that have been developed can be broadly divided into two categories; those aiming to stimulate antitoxic immunity and those intending to induce antibacterial immunity. Experiments with animal models support a protective role for either or both antitoxic and antibacterial immunity. It has been suggested that when both types of immunity work in unison, there is a synergistic effect. [Holmgren, J. et al. *J. Infect. Dis.* 136 Suppl., S105–S1122 (1977); Peterson, J. W. *Infect. Immun.* 26, 594 (1979); Resnick, I. G. et al. *Infect. Immun.* 13, 375 (1980); Svennerholm, A. -M. et al. *Infect. Immun.* 13, 735 (1976)]. However, it appears that protective immunity in humans can be conferred without such synergistic effect, that is by either antitoxic immunity or antibacterial immunity [Eubanks, E. R. et al. *Infect. Immun.* 15, 533 (1977); Fujita, K. et al. *J. Infect. Dis.* 125, 647 (1972); Holmgren, J., *J. Infect. Dis.*, supra; Lange, S. et al. *Acta Path. Microbiol. Scand Sect. C* 86, 145 (1978); Peterson, J. W., supra (1979); Pierce, N. F. et al. *Infect Immun.* 37, 687 (1982); Pierce, N. F. et al. *Infect. Immun.* 21, 185 (1978); Pierce, N. F. et al. *J. Infect. Dis.* 135, 888 (1977); Resnick, I. G. et al., supra; Svennerholm, A. -M. et al, supra].

KILLED WHOLE CELL VACCINES

1. Parenteral Whole Cell Vaccines

For almost a century, killed whole *V. cholerae* have been employed as parenteral vaccines; these vaccines are still commercially available. Experience with the parenteral whole cell vaccines has been reviewed in Joo, I. "Cholera Vaccines." In *Cholera.* (Barua D. and Burrows W., eds.), Saunders, Philadelphia, pp. 333–355 (1974) and in Feeley, J. D. et al. In *Cholera and Related Diarrheas.* 43rd Nobel Symp., Stockholm 1978. (O. Oucherlong, J. Holmgren, eds.) Karger, Basel, pp. 204–210 (1980). Such vaccines stimulate high titers of serum vibrioicidal antibodies. They also stimulate increases in intestinal SIgA antibody to *V. cholerae* somatic O antigen when given to Pakistanis but not to Swedes [Svennerholm, A. -M. et al. Infect. Immun. 30., 427 (1980); Svennerholm, A. -M. et al. *Scan. J. Immun.* 6, 1345 (1977)]. It has been suggested that the Pakistani vaccine recipients respond in this way because they are already immunologically primed from prior antigenic contact, while persons living in a non-endemic area (e.g., Sweden) are not. In field trials parenteral killed whole cell vaccines have been shown to confer significant protection against the homologous *V. cholerae* serotype, but usually for a period of less than one year [Joo, I. supra; Feeley, J. C., supra; Svennerholm, A. -M. et al. supra, (1980); Svennerholm, A. -M. et al. supra, (1977); Mosley, W. H. et al. *Bull. Wld. Hlth. Org.* 49, 13 (1973); Philippines Cholera Committee, *Bull. Wld. Hlth. Org.* 49, 381 (1973)]. There is some evidence to suggest that parenteral whole cell Inaba vaccine provides good, short term protection against Ogawa, as well as against Inaba cholera, while Ogawa vaccine is effective only against Ogawa.

By use of adjuvants, it has been possible to maintain a vaccine efficacy of approximately 70% for up to one-and-one-half years with parenteral vaccine (see, e.g., Saroso, J. S. et al. *Bull. Wld. Hlth. Org.* 56, 619 (1978)). However, the adverse reactions encountered at the site of inoculation with adjuvanted vaccines (which include sterile abscesses) are sufficiently frequent and severe to preclude routine use of such adjuvanted vaccines.

2. Oral Whole Cell Vaccines

Killed whole vibrios administered orally stimulate the appearance of local intestinal antivibrio antibody. [Freter, R. *J. Infect Dis.* 111, 37 (1972); Freter R. et al. *J. Immunol.* 91 724 (1963); Ganguly, R. et al. *Bull. Wld. Hlth. Org.* 52, 323 (1975)]. Other investigators have shown substantial vaccine efficacy, but a large proportion of the vaccines developed diarrhea after subsequent challenge with pathogenic vibrios [Cash, R. A. et al. *J. Infect. Dis.* 130, 325 (1974)].

TOXOIDS

Immunizing agents intended to prevent cholera by means of stimulating antitoxic immunity include:

1) Formaldehyde-treated cholera toxoid 2) Glutaraldehyde-treated cholera toxoid; 3) Purified B subunit; and 4) Procholeragenoid (with or without formaldehyde treatment).

1. Formaldehyde-Treated Cholera Toxoid

Treatment of purified cholera toxin in vitro with formaldehyde eradicates its toxicity, resulting in a toxoid that exhibits little toxic biological activity but stimulates antitoxic antibodies following parenteral immunization of animals. However, when the first toxoid of this type was administered to monkeys and man as a parenteral vaccine, the toxoid reverted to partial toxicity causing unacceptable local adverse reactions at the site of inoculation [Northrup, R. S. et al. *J. Infect. Dis.* 125, 471 (1972)]. An aluminum-adjuvanted formalinized cholera toxoid has been administered parenterally to Bangladeshi volunteers, including lactating mothers, but no field trials with this vaccine have been undertaken [Merson, M. H. et al. *Lancet I*, 931 (1980)]. Formalinized cholera toxoid prepared in the presence of glycine has also been tried by the parenteral route, but the vaccine showed no evidence of efficacy [Ohtomo, N. In *Proceedings of the 12th Joint Conference on Cholera*, U.S.-Japan Cooperative Medical Science Program, Sapporo (Fukumi H., Zinnaka Y., eds.) pp. 286–296 (1976); Noriki, H. In *Proceedings of the 12th Joint Conference on Cholera*, U.S.-Japan Cooperative Medical Science Program, Sapporo (Fukumi H., Zinnaka Y., eds.) pp. 302–310 (1976)].

2. Glutaraldehyde-Treated Cholera Toxoid

Methods have been developed for the large-scale preparation of a glutaraldehyde-treated cholera toxoid that is essentially free of contaminating somatic antigen [Rappaport, E. S. et al. *Infect. Immun.* 14, 687 (1976)]. It was hoped that this antigen could be used to assess in a "pure" manner the protective role of antitoxic immunity alone. A large-scale field trial of this toxoid given as a parenteral vaccine was carried out in Bangladesh in 1974 [Curlin, G. et al. In *Proceeding of the 11th Joint Conference on Cholera*, U.S.-Japan Cooperative Medical Science Program. pp. 314–329, New Orleans, (1975)]. The toxoid stimulated high titers of circulating antitoxins in Bangladeshi recipients. Two waves of cholera, E1 Tor Inaba followed by E1 Tor Ogawa, struck the field area allowing a fair evaluation of vaccine efficacy. A protective effect could be demonstrated in only one age group and was restricted to the period of the Inaba epidemic, so that glutaraldehyde-treated cholera toxoid given alone as a parenteral vaccine provided little protection and was substantially inferior to similar field trials in the same population with parenteral killed whole cell vaccines.

The use of glutaraldehyde-treated cholera toxoid as an oral vaccine has been investigated on the assumption that toxoid given by this route might be more efficient by stimulating intestinal antitoxin [Levine, M. M. et al. *Trans. Roy. Soc. Trop. Med. Hyg.* 73, 3, (1979)]. Two groups of volunteers were immunized with three 2.0 mg., or three 8.0 mg doses of toxoid given directly into the small intestinal lumen (via intestinal tube) at monthly intervals. The vaccines and unimmunized controls then participated in experimental cholera challenge studies. In neither challenge study was the attack rate or severity of diarrhea significantly diminished in the vaccines when compared with controls. The lack of efficacy of oral glutaraldehyde-treated cholera toxoid may be due to the fact that the capacity of B subunits to bind to GM1 ganglioside is greatly diminished as a consequence of toxoiding with glutaraldehyde.

3. Purified B Subunit

Cholera enterotoxin is composed of two subunits designated A and B. The A subunit induces the enzymatic changes which lead to fluid secretion, while the non-toxic B subunit is the immunogenic moiety that binds to the receptor for toxin (GM1 ganglioside) on intestinal epithelial cells [Holmgren, J. *Nature* 292, 413 (1981)]. It has been shown that purified B subunit given either orally or parenterally to Bangladeshis stimulates the appearance of SIgA antitoxin in intestinal fluid, a result attributable to immunological priming in a cholera-endemic area [Svennerholm, A. -M. et al. *Lancet I*, 305 (1982)].

The major advantages of B subunit oral vaccine to stimulate antitoxic immunity include its complete safety (there is not potential for reversion to toxin as exists with toxoids) and retention of its capacity to adhere to toxin receptors on enterocytes. Animal studies suggest that it is less potent than native holotoxin in stimulating antitoxin [Pierce, N. F. supra, (1982)].

It will be understood that the purified B subunit can be used, if at all, in conjunction with e.g. oral killed vibrios as a combination oral vaccine intended to stimulate both antibacterial and antitoxic antibodies.

4. Procholeragenoid

Procholeragenoid is the large molecular weight toxoid (ca. 1,000,000 MW) that results when cholera enterotoxin is heated at 65° C. for at least five minutes [Finkelstein, R. A. et al. *J. Immunol.* 107, 1043 (1971)]. It is immunogenic while retaining less that 5% of the biological toxic activity of the parent toxin. Heating for longer times (e.g., 25 minutes) produces less biological toxicity [Germanier, R. et al. *Infect. Immul* 13, 1692 (1976)], and subsequent treatment with formaldehyde completely abolishes residual biological toxicity. The resultant formaldehyde-treated procholeragenoid is at least as potent as the parent toxin in stimulating serum antitoxin following immunization of rabbits. Swiss volunteers developed brisk serum antitoxin responses following parenteral immunization with 10, 30, or 100 mcg doses of formaldehyde-treated procholeragenoid [Germanier, R. et al. *J. Infect. Dis.* 135. 512 (1977)]. No notable adverse reactions were observed.

As an oral antigen procholeragenoid is more immunogenic when given in the form without formaldehyde-treatment. In dogs, untreated procholeragenoid is tolerated as well as an oral vaccine; oral doses (with $NaHCO_3$) up to 500 mcg do not case diarrhea. Five 500 mcg doses spaced over 42 days stimulate significant protection in dogs against oral challenge with pathogenic *V. cholerae*. Doses of 50 mcg and 200 mcg with $NaHCO_3$ have been given to groups of six and four adult volunteers, respectively, without eliciting adverse reactions.

It will be understood that procholeragenoid can be used in conjunction with e.g. killed vibrios or other relevant antigens capable of stimulating antibacterial immunity so that the antitoxic immunity induced by procholeragenoid is enhanced.

COMBINATION VACCINES

The major attraction of non-living, oral cholera vaccine is its safety. An oral vaccine consisting of a combination of antigens, intending to stimulate both antibacterial and antitoxic immunity, would be most likely to succeed for the following reasons: Toxoid vaccines that stimulate purely antitoxic immunity have not been shown to be efficacious in protecting man against cholera, although they may protect animal models. In addition, oral or parenteral killed whole cell vaccines that stimulate no antitoxic immunity provide significant protection against cholera in man, albeit for a short period of time. Furthermore, combinations of antigens (such as crude cholera toxin, or toxin plus lipopolysaccharide) that stimulate both antitoxic and antibacterial immunity, give synergistic protection.

Two studies so far have been carried out in many with combination vaccines. In the first, nine volunteers who ingested glutaraldehyde-treated cholera toxoid (2 mg weekly for four weeks) plus killed E1 Tor Inaba vibrios ($10^{10}$ vibrios twice weekly for four weeks) were challenged after one month with $10^6$ pathogenic E1 Tor Inaba vibrios, along with six unimmunized controls. Diarrhea occurred in only two of nine vaccines, versus four of six controls (vaccine efficacy 67%) and illness was clearly attenuated in the two ill vaccines. More pertinent, perhaps, is the observation that *V. cholerae* could be directly cultured from stools of only two of nine vaccines, versus six of six controls. This demonstrates that immunologic mechanisms impeded the proliferation of vibrios.

More recently, three doses of B subunit/killed whole cell vaccine was given to adult volunteers who participated in a vaccine efficacy challenge. The combination vaccine was give on days 0, 14, and 28. Each of the three doses of vaccine contained 0.5 mg of purified B subunit and $2\times10^{11}$ killed *V. cholerae* ($5\times10^{10}$ classical Inaba, $5\times10^{10}$ classical Ogawa, and $1\times10^{11}$ E1 Tor Inaba).

A group of eleven volunteers immunized with this combination vaccine were challenged one month after their last dose with $10^6$ pathogenic *V. cholerae* E1 Tor Inaba, along with seven control volunteers. Diarrhea occurred in seven of seven controls, but in only four of eleven vaccines (p=0.01). The illness in the four vaccines was definitely milder.

Thus, results of studies with oral toxoid/killed whole cell vaccine combinations demonstrate a measurable degree of efficacy. The protective vaccine efficacy, however, is only moderate (55–65%) and multiple doses are required to induce the protection.

ATTENUATED V. CHOLERAE VACCINES

Both classical and E1 Tor clinical cholera infections stimulate a high degree of protective immunity for at least three years in NorthAmerican volunteers [Cash, R. A. et al., supra (1974); Levine, M. M. et al., supra (1979); Levine, M. M. et al. "Volunteers studies in development of vaccines against cholera and enterotoxigenic *Escherichia coli*: a review," in *Acute Enteric Infections in Children: New Prospects for Treatment and Prevention*. (T. Holm, J. Holmgren, M. Merson, and R. Mollby, eds.) Elsevier, Amsterdam, pp. 443–459 (1981); and Levine, M. M. et al. *J. Infect. Dis.* 143, 818 (1981)]. Based on these observations in volunteers, perhaps the most promising approach toward immunologic control of cholera may be with attenuated non-toxigenic *V. cholerae* strains employed as oral vaccines.

1. Naturally-Occurring Strains

Non-toxigenic *V. cholerae* 01 strains isolated from environmental sources in India and Brazil have been evaluated in volunteers as potential vaccine candidates with disappointing results. They either failed to colonize the intestine of man, or did so minimally; vibrocidal antibody responses were meager, and they failed to provide protection in experimental challenge studies [Cash, R. A. et al. *Infect. Immun*, 10, 762 (1974); Levine M. M. et al. *J. Infect. Dis.* 145, 296 (1982)]. Many of these strains appear to lack the toxin gene, as measured by hybridization with a radioactive DNA probe [Kaper, J. B. et al. *Infect. Immun.* 32, 661 (1981)].

2. Mutagenized Attenuated Strains

Classical Inaba 569B has been mutagenized with nitrosoguanide (NTG) and hypotoxinogenic mutant isolated [Finkelstien, R. A. et al. *J. Infect. Dis.* 129, 117 (1974); Holmes, R. K. et al. *J. Clin. Invest.* 55, 551 (1975). This mutant strain, M13, was fed to volunteers. Diarrhea did not occur but the strain colonized poorly. Challenge studies demonstrated that some protective efficacy was conferred by immunization with multiple doses [Woodward, E. et al. *Develop. Biol. Stand.* 33, 108, (1976)].

E1 Tor Ogawa 3083 has also been mutagenized [Honda, T. et al. *Proc. Nat. Acad. Sci.* 76, 2052 (1979)]. Brute force selection and analysis of thousands of colonies yielded one isolate that continued to produce the immunogenic B subunit while failing to produce detectable A subunit or holotoxin. The one isolate, Texas Star-SR, fulfilled these criteria. Texas Star-SR produces normal or increased amount of B subunit but is negative in assays for holotoxin activity or A subunit activity.

Texas Star-SR has been extensively evaluated in volunteers (see, e.g., Levine M. M. et al. *Acute Enteric*, supra (1981)). Groups of five volunteers received two $10^9$ organism doses one week apart and eighteen more volunteers ingested two $2\times10^{10}$ organism doses one week apart. Some degree of diarrhea was seen in sixteen of the sixty-eight vaccines (24%). In only one individual did the total stool volume exceed 100 liter (1464 ml). Typically, the vaccine-induced diarrhea consisted of two or three small, loose stools totalling less than 400 ml in volume. Vaccine organisms were recovered from coprocultures of approximately one-half of the vaccine recipients. Where jejunal fluid was cultured (recipients of doses of $10^8$ or more vaccine organisms), cultures were positive in thirty-five of forty-six vaccines (76%). Hundreds of Texas Star clones recovered from coprocultures and jejunal fluid cultures were examined for cholera holotoxin by the sensitive Y-1 adrenal cell assay; none were positive.

Significant rises in serum antitoxin were detected in only 29% of the vaccines; however, 93% manifested significant rises in serum vibriocidal antibody and the titers were substantially close to those encountered following infection with pathogenic *V. cholerae*. In experimental challenge studies in volunteers, Texas Star-SR was found to confer significant protection against challenge with both EL Tor Ogawa And E1 Tor Inaba vibrios. One or two doses of Texas Star-SR attenuated oral vaccine confers good protection against E1 Tor cholera.

It is clear that the use of attenuated strains has intrinsic advantages since such strains mimic infection-derived immunity to cholera. However, the Texas Star-SR strains suffers from certain drawbacks. To begin with, mutagenesis (e.g., with nitrosoguanidine) induces multiple mutations, not all of which are necessarily recognized. Furthermore, the precise genetic lesion that is presumed to be responsible for the attenuation of Texas Star-SR is not known. In addition, Texas Star-SR may revert to virulence, like any pathogen mutated with nitrosoguanidine.

Applicants of the present invention have isolated, by novel method, deletion mutants of a virulent strain of *Vibrio cholerae* known to produce both immunity and disease in volunteers. The deletions are restriction endonuclease fragments. The vaccine strains of the present invention have been specifically altered through the use of recombinant DNA techniques to render the avirulent without affecting other components necessary for immunity. This attenuation was accomplished by using restriction endonucleases which cleave the DNA of the bacterium at specific sites, to specifically delete the genes responsible for cholera toxin (i.e., the ctx gene). Plasmids carrying the ctx gene were digested with restriction endonucleases to delete the ctx gene, but were constructed to retain extensive lengths of flanking DNA of the *V. cholerae* chromosome. Conjugal gene transfer of the plasmids into *V. cholerae* yielded an avirulent *V. cholerae* strain carrying the extrachromosomal copies of the plasmids. Subsequent conjugation with cells having other plasmids produced, after appropriate selection of selectable plasmid markers, *V. cholerae* strains having deletions in the ctx regions. Such nontoxigenic deletion mutants would then be capable of colonizing the small intestine and stimulating local, protective immunity directed against the bacterial cell. After the transient colonization episode, the vaccine would be protective against subsequent infection with virulent toxigenic *V. cholerae* strains.

The genes for *V. cholerae* toxin have been cloned [Pearson, G. D. N. et al. *Prod. Nat. Acad. Sci.* 79, 2976 (1982); Kaper, J. B. et al. *Amer. Soc. Micribiol. Abstr. Annu. Meeting, Atlanta, Georgia*, 36 (1982); Kaper, J. B. et al. *Symposium on Enteric Infections in Man and in Animals: Standardization of Immunological Procedures*, Dublin, Ireland, Abstract No. 2.5 (1982)]. Toxin structural gene deletion mutants of *V. cholerae* have been isolated, but only by infection with mutagenic vibriophages capable of integration at random sites along to chromosome [Mekalanos, J. J. et al. *Proc. Nat. Acad. Sci.* 79, 151, (1982)]. Recombination in *Vibrio cholerae* has been reported, but it has not been used to isolate restriction fragment deletions in the ctx genes for vaccination purposes [Parker, C. et al. *J. Bact.* 112, 707 (1972); Johnson, S. R. et al. *Molec. Gen. Genet.* 170, 93 (1979); Sublett, R. D. et al. *Infect. Immun.* 32 1132 (1981) and Thomson, J. A. et al. *J. Bact.* 148, 374 (1981)].

BRIEF DESCRIPTION OF THE INVENTION

A culture of *Vibrio cholerae* is described comprising a *Vibrio cholerae* strain having a restriction endonuclease fragment of DNA deleted to confer avirulence and to retain capacity to colonize the intestine of a host animal. The DNA fragment deleted may code for the *V. cholerae* toxin or portions thereof such as the $A_1$ subunit. One isolated deletion mutant encompasses a deletion in the ctx gene, as defined by Acc I restriction endonuclease sites.

A method of isolating such deletion mutants of *Vibrio cholerae* is also described, comprising the steps of (a) constructing a first plasmid comprising *Vibrio cholerae* flanking sequences of one or more deleted restriction endonuclease fragments and a gene for a first selectable marker of foreign origin ligated to said flanking sequences to substitute for and to be in the place of said deleted fragment, wherein said sequences are of sufficient length to promote detectable in vivo recombination;

(b) mating a virulent strain of *Vibrio cholerae* with a first microorganism carrying the first plasmid;

(c) selecting for *Vibrio cholerae* expressing the first selectable marker;

(d) mating the selected product of step (c) with a second microorganism carrying a second plasmid with a second selectable marker, said second plasmid being incompatible with the first plasmid; and (e) selecting for *Vibrio cholerae* expressing both the first selectable marker and the second selectable marker.

A second culture of *Vibrio cholerae* is described comprising a *Vibrio cholerae* strain having a first restriction endonuclease fragment of DNA deleted to confer avirulence and retain capacity to colonize the intestine of a host animal and having a second restriction endonuclease fragment of DNA coding for zonula occludens toxin (ZOT) deleted to reduce residual diarrhea in the host animal. The first DNA fragment deleted may code for the *V. cholerae* toxin or portions thereof such as the $A_1$ subunit. One isolated deletion mutant encompasses a deletion in the ctx gene, as defined by Acc I restriction endonuclease sites, and a deletion in the zot gene. Another isolated deletion mutant encompasses a deletion in the ctx gene, as defined by Xba I and Cla I restriction endonuclease sites, and a deletion in the zot gene, as defined by Stu I and Acc I restriction endonuclease sites A method of isolating such deletion mutants of *Vibrio cholerae* is also described, comprising the steps of (a) constructing a first plasmid comprising *Vibrio cholerae* flanking sequences of one or more deleted restriction endonuclease fragments and a gene for a selectable marker of foreign origin ligated to said flanking sequences to substitute for and to be in place of said deleted fragment, wherein said sequences are of sufficient length to promote detectable in vivo recombination;

(b) mating a virulent strain of *Vibrio cholerae* with a first microorganism carrying the first plasmid;

(c) selecting for *Vibrio cholerae* expressing the first selectable marker;

(d) mating the selected product of step (c) with a second microorganism carrying a second plasmid with a second selectable marker, said second plasmid being incompatible with the first plasmid;

(e) selecting for *Vibrio cholerae* expressing both the first selectable marker and the second selectable marker;

(f) constructing a third plasmid comprising *Vibrio cholerae* flanking sequences of one or more deleted restriction endonuclease fragments homologous to those described in step (a) but differing in the absence of a selectable marker of foreign origin;

(g) mating the selected product of step (e) with a third microorganism carrying a third plasmid described in step (f); and (h) selecting for *Vibrio cholerae* which no longer expresses the first selectable marker.

This method may be used for ZOT minus only strains or for making a ZOT minus derivative of a strain which is already deleted for cholera toxin genes.

A third culture of *Vibrio cholerae* is described, comprising a *Vibrio cholerae* strain having a region of the chromosomal DNA coding for cholera toxin and zonula occludens toxin (ZOT) deleted. A method of isolating such deletion mutants of *Vibrio cholerae* is also described comprising the steps of (a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae;*

(b) mating a microorganism carrying said plasmid with a virulent strain of *Vibrio cholerae* containing said sequences inserted between flanking identical copies of a second sequence such as RS1 elements of sufficient length to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker, and therefore have a region of the chromosomal DNA coding for cholera toxin and zonula occludens toxin deleted.

A fourth culture of *Vibrio cholerae* is described, comprising a *Vibrio cholerae* strain having a region of chromosomal DNA coding for cholera toxin and zonula occludens toxin deleted, and having inserted a mercury resistance gene and DNA coding for B subunit of *Vibrio cholerae* toxin. A method of isolating such deletion mutants is also described comprising the steps of:

(a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae*;

(b) mating a microorganism carrying said plasmid with a virulent strain of *Vibrio cholerae* containing said sequences coding for cholera toxin and zonula occludens toxin inserted between flanking identical copies of a second sequence of sufficient length to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker, and therefore have a region of the chromosomal DNA coding for cholera toxin and zonula occludens toxin deleted;

(f) constructing a second plasmid comprising a mercury resistance gene and DNA coding for B subunit of *Vibrio cholerae* toxin and a gene for a second selectable marker of foreign origin wherein said plasmid is incapable of replicating extrachromosomally in *Vibrio cholerae*, and wherein sequences of sufficient length to promote detectable in vivo recombination flank said mercury resistance gene and DNA coding for B subunit of *Vibrio cholerae* toxin;

(g) mating a microorganism carrying said second plasmid with said *Vibrio cholerae* recited in step (e) containing sequences homologous to said sequences of sufficient length to promote detectable in vivo recombination;

(h) selecting for *Vibrio cholerae* expressing said second selectable marker;

(i) growing the selected product of step (h) in the absence of the second selective agent;

(j) selecting for *Vibrio cholerae* which no longer express the second selective marker; and (k) screening said *Vibrio cholerae* recited in step (j) for *Vibrio cholerae* that have a mercury resistance gene and DNA coding for B subunit of *Vibrio cholerae* toxin and have a region of chromosomal DNA coding for cholera toxin and zonula occludens toxin deleted.

The *Vibrio cholerae* deletion mutants of this invention are useful in vaccination against cholera.

One *Vibrio cholerae* strain of the present invention, designated CVD101, is expected to confer substantially close to 100% efficacy in humans against subsequent disease with a strain of a similar serotype. Other *Vibrio cholerae* strains of the present invention, designated by the second culture, and the third culture such as CVD109, are expected to confer substantially 100% efficacy in humans against subsequent disease with a strain of a similar serotype and to avoid undesirable side effects such as diarrhea and nausea, and cramping. Another *Vibrio cholerae* strain of the present invention, CVD110, is designated by the fourth culture.

BRIEF DESCRIPTION OF THE DRAWINGS

FIG. 9. Scheme for construction of pCVD14 and pCVD15.

FIG. 10. Scheme for construction of pJBK108.

FIGS. 15A, 15B, and 15C. Freeze-fracture studies of rabbit ileal tissue exposed to culture supernatants of *V. cholerae* a, An intact ZO with numerous intersections (arrowheads) between junctional strands M, microvilli. b, An affected ZO from ileal tissue exposed to *V. cholerae* 395; the reticulum appears simplified due to greatly decreased incidence of strand intersections. c, Quantitation of ZO complexity in tissues exposed to culture supernatants or broth control.

FIG. 18 (pages 1 and 2). DNA sequence of the zot gene for zonula occludens toxin from nucleotides number 1 to 1428. Letters above the DNA sequence indicate the predicted amino acid sequence of the ZOT protein encoded by the zot gene.

FIG. 20. Scheme for construction of CVD110.

FIG. 21 (pages 1 to 6). DNA sequence of the ctxB gene and mer gene inserted into the hlyA gene.

Figure 22:
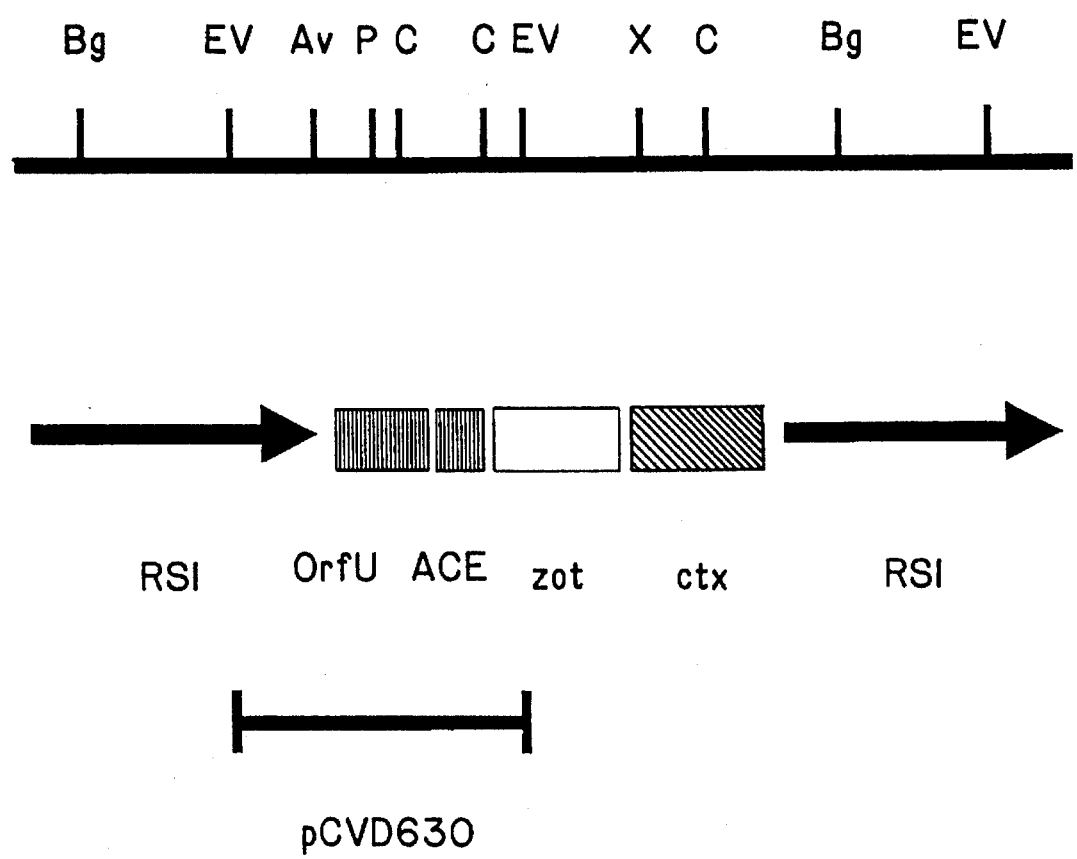

Abbreviations for restriction endonuclease sites in the drawings are as follows:
- A=Acc I restriction endonuclease site
- B=Bgl II restriction endonuclease site
- C=Cla I restriction endonuclease site
- E=Eco RI restriction endonuclease site
- H=Hind III restriction endonuclease site
- P=Pst I restriction endonuclease site
- S=Sal I restriction endonuclease site
- X=Xba I restriction endonuclease site
- K=Kpn I restriction endonuclease site Other abbreviations in the drawings and elsewhere include:
- Ap=Ampicillin resistance gene
- $Ap^r$=Ampicillin resistance phenotype
- $Ap^s$=Ampicillin sensitive phenotype
- Chrom=Chromosome
- CT=Cholera toxin
- ctx=gene for cholera toxin
- CTA=gene for A subunit of cholera toxin
- ctxA=gene for A subunit of cholera toxin
- CTB=gene for B subunit of cholera toxin
- ctxB=gene for B subunit of cholera toxin
- hylA=gene for hemolysin
- kb=Kilobases
- mer=gene for mercury resistance
- p=plasmid
- Su=Sulfonamide
- $Su^r$=Sulfonamide resistance phenotype
- Tc=tetracycline
- $Tc^s$=tetracycline sensitive phenotype
- Tp=Trimethoprin
- zot=gene for zonula occludens toxin FIG. 22 Map showing the relative positions of the ctx, zot and ace genes, OrfU (open reading frame of unknown function), and the RS1 flanking sequences. (RS1 is shown by large arrows). The two boxes with the vertical stripes correspond to the two open reading frames in which ACE activity was initially localized. It is now thought that ACE activity is localized to the open reading frame adjacent to the zot gene. The fragment contained in the clone pCVD630 is shown.

FIG. 23. Using chamber activity of V. cholera strains CVD110 and CVD110 containing pCVD630. Panel on left shows changes induced in short circuit current (ISC) and panel on right shows changes in potential difference (PD).

FIG. 24. DNA sequence of the 2.9 kb EcoRV fragment containing ACE activity (sequence GATATC at beginning and end of sequence is the EcoRV site). The complete DNA sequence for classical strain 395 is shown (SEQ ID No.: 1). Below the 395 sequence is shown the sequence for this region from El Tor strain E7946 (SEQ ID No.: 4)—only those bases of E7946 which differ from those in 395 are shown. Where the sequence is identical for the two strains, only the 395 sequence is shown. (Dashed lines at bases 236–239 show that E7946 has a 3 base insert (AGT) which is not present in 395). Above the primary DNA sequence line is shown the amino acid sequence (in single letter code) predicted from the 395 sequence. The two ORFs are translated; classical 395 OrfU spans bases 1034 to 2218 (SEQ ID No.: 3); classical 395 ACE spans bases 2221 to 2508 (SEQ ID No.: 2); El Tor OrfU spans bases 1037 to 2221 (SEQ ID No.: 6); and, El Tor ACE spans bases 2224 to 2511 (SEQ ID No.: 5).

DETAILED DESCRIPTION OF THE INVENTION

The principle of the present invention is the isolation of a *Vibrio cholerae* vaccine strain specifically altered through recombinant DNA technology to render it avirulent without affecting other components necessary for immunity. This attenuation was accomplished by restriction endonuclease digestion of plasmids carrying appropriate *V. cholera* sequences, to specifically delete the genes coding for cholera toxin, or portion thereof. Conjugal gene transfer of these digested plasmids, followed by procedures for selecting in vivo recombinants with virulent host *V. cholera*, resulted in strains without the toxin genes portion thereof. It will be understood that the methods of the present invention are applicable to the isolation of other deletion mutants of virulent *V. cholerae*, or to the isolation of strains having all or part of such deleted sequences reintroduced into the *V. cholerae* cell.

The starting material for the vaccine was the toxigenic *Vibrio cholerae* strain N16961, which has been demonstrated to produce in volunteers both typical diarrheal disease and strong, protective immunity to subsequent infection [Levine, M. M. et al., *Acute enteric*, supra. 1981]. The region of the bacterial chromosome which was found to be responsible for production of cholera toxin was cloned into the plasmid cloning vehicle pBR325, after screening Hind III digest of *V. cholerae* with an *E. coli* heat-labile enterotoxin gene probe [Kaper et al. Amer. Soc., supra; Kaper et al. *Symposium*, supra]. The *V. cholerae* chromosome fragment was found to contain all genes necessary for toxin production. Next, this chromosomal region was then analyzed and mapped for the exact portions containing the toxin genes [Kaper, J. B. et al. *Lancet II*, 1162 (1981)]. Restriction enzymes were employed to cut out the DNA fragments containing these genes and a DNA fragment encoding a selectable marker (e.g., resistance to ampicillin) was inserted by ligation. The ampicillin resistance gene and the flanking *Vibrio* DNA were then cloned in a derivative of pRK290 which can be transferred from *E. coli* to *V. cholerae*. The resulting plasmid, pJBK55, was transferred from *E. coli* t K-12 to *V. cholerae* N16961 by conjugation.

Figure 1:
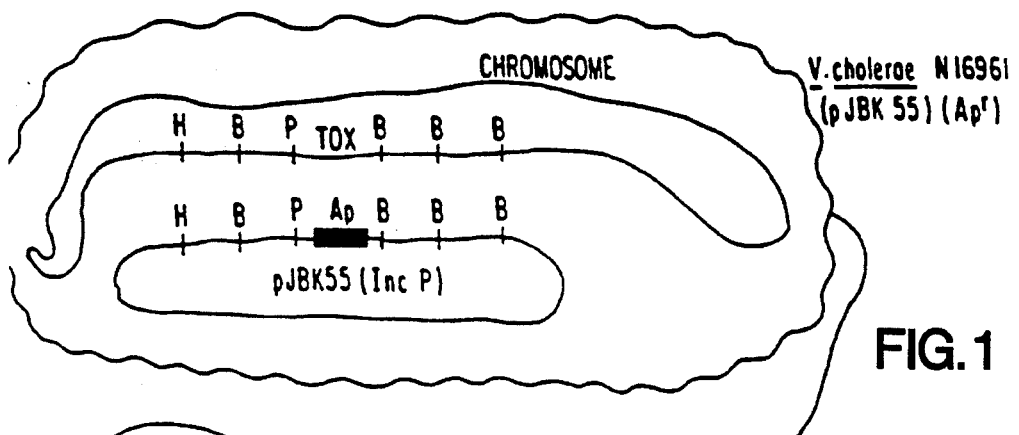
FIG. 1. *V. cholerae* N16961 (pJBK55) (Ap')
Figure 2:
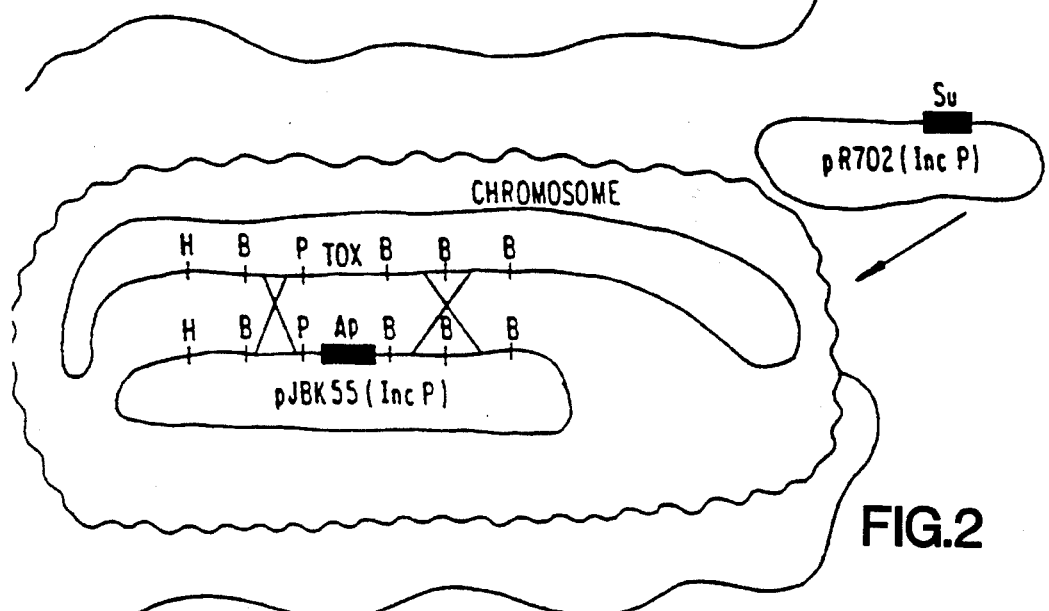
FIG. 2. Processes of crossing-over and conjugal gene transfer to construct *V. cholerae* JBK56.
Figure 3:
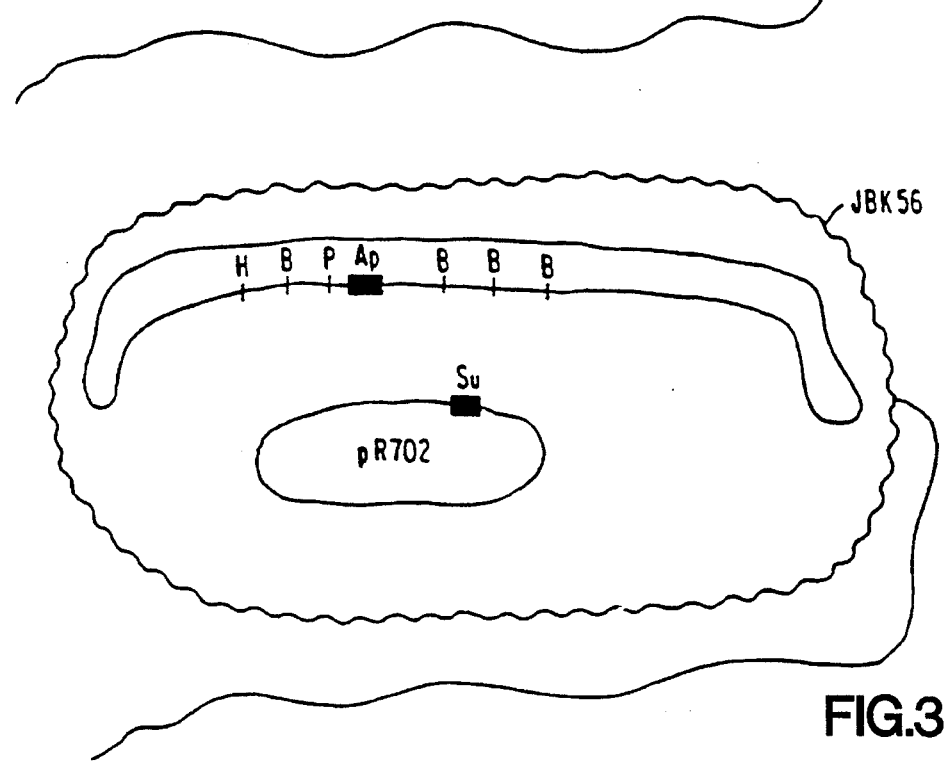
FIG. 3. *V. cholerae* JBK56.
Figure 5:
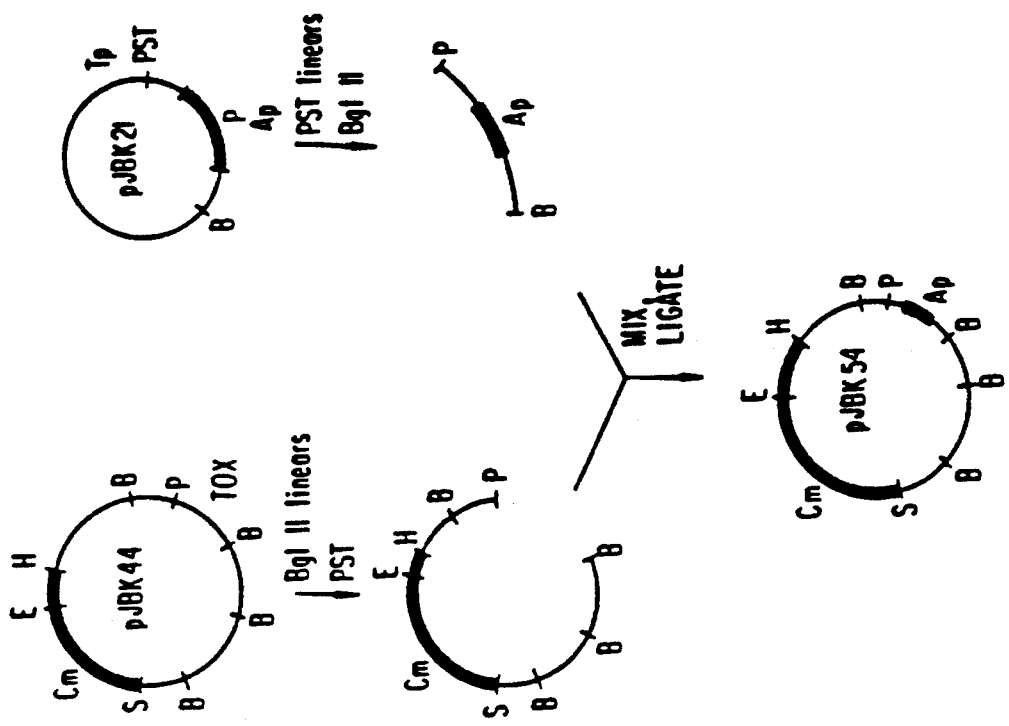
FIG. 5. Scheme for construction of pJBK54.

The resulting strain, *V. cholerae* N16961 (pJBK55) ($Ap^r$) contained a region in its chromosome having intact toxin genes and, in an extrachromosomal state, a plasmid containing this same region with the toxin genes deleted and a gene for ampicillin substituted. (See FIG. 1.) At a low frequency, perhaps one in $10^6$ to one in $10^8$, the identical regions flanking the chromosomal toxin genes and the extrachromosomal (plasmid) ampicillin resistance gene will exchange and "cross over" or undergo in vivo recombination so that the region of DNA containing the resistance gene displaces the toxin gene on the chromosome (FIG. 2). This rare event is selected by testing a mixture of mutated and non-mutated cells for individual cells which are able to serve as host for an incoming incompatible plasmid [Ruvkun, G. B. et al. Nature 289, 85 (1981)]. Plasmids are divided into groups designated A through W, the members of which cannot stably coexist with each other. For example, a plasmid of incompatibility group P cannot be stably maintained in the same cell as another P group (Inc P) plasmid. Thus, Inc P plasmids, such as R702, which specify resistance to sulfonamide, cannot be maintained in a cell which has another Inc P. plasmid such as PRK 290, pJBK45, or pJBK55. Therefore, R702 can be maintained in a strain in which the ampicillin resistance has recombined into the chromosome but not one in which an Inc P Plasmid (e.g. pJBK55) is replicating extrachromosomally. By mating an E. coli strain containing Inc P R702 (sulfonamide resistant) and V. cholerae pJBK55 (ampicillin resistant) and selecting for *V. cholerae* which are resistant to both ampicillin and sulfonamide, colonies are isolated in which the sulfonamide resistance is mediated extrachromosomally by p702 and the ampicillin resistance is mediated chromosomally through substitution of the ampicillin resistance gene for the toxin gene (FIG. 3). One such strain, designated *V. cholerae* JBK56 was isolated and when tested for toxin production was found to be nontoxinogenic.

The final version of the vaccine strain, JBK70, was produced by substituting resistance to ampicillin, a therapeutically useful antibiotic, with resistance to mercury. This substitution was accomplished by cloning a gene for mercury resistance directly into the ampicillin resistant gene of pJBK55, thereby inactivating ampicillin resistance and conferring mercury resistance. The resulting plasmid, pJBK66 was also incompatible with R702 and was transferred to *V. cholerae* JBK56. A mutant in which the mercury resistance was recombined into the chromosome was selected using the Inc P plasmid R702 and selecting for *V. cholerae* which were ampicillin sensitive, mercury resistant, and sulfonamide resistant. A spontaneous derivative was later selected which was cured of pR702. The final mutant, JBK70, was nontoxinogenic and resistant to mercury only.

The vaccine strain *V. cholerae* JBK70 is one of the Inaba serotype. The other major serotype of *V. cholerae* is the Ogawa serotype. It is expected that a vaccine prepared from one serotype will protect against the other serotype (34). In the event that this is not the case, a live vaccine strain can be prepared from an Ogawa serotype and protection in volunteers [Levine, M. M. et al. *Acute enteric*, supra (1981)]. The exact mutation created in strain *V. cholerae* Inaba JBK56 was recreated in strain E7946 by directly transferring the region of the chromosome containing the ampicillin resistance in place of the toxin gene in JBK56 into E7946 through genetic recombination mediated by P, the sex factor of *V. cholerae* [Parker, C. et al., supra]. The P factor, which is distinct from Inc P plasmid, was transferred into JBK56 and was then mated with a rifampin resistant mutant of E7946. By selection of a mutant which was resistant to both ampicillin and rifampin, a vaccine strain was isolated which was of the Ogawa serotype with the toxin genes completely deleted.

If antibacterial immunity is insufficient for protection, then an antitoxic component can be added by adding back the genes for production of cholera toxin B but not A subunit. This has been accomplished by cloning the B subunit gene into the cloning vector pMS9. The resulting plasmid, pJBK51, produces high levels of B subunit and was reintroduced into the nontoxic vaccine strain *V. cholerae* JBK70 to make an attenuated vaccine strain JBK70 (pJBK51) which fails to produce the A subunit.

The vaccine strains of the present invention are derived inter alia from *V. cholerae* N16961 having the serotype Inaba. It will be understood that other strains or other biotypes and serotypes can be used to substitute for N16961 to produce vaccine strains having specific deletions in the ctx gene or genes, or in other locations along the *V. cholerae* chromosome. Since the object of isolating such vaccine strains is to mimic the infection process without associated pathological phenomena, site-directed mutagenesis of virulent strains, as described in this application, produces substantial possibilities in the prophylactic vaccination against cholera.

For example, applicants have produced another *V. cholerae* vaccine strain CVD101, characterized by a deletion of most of the A subunit gene in 2 copies of the ctx gene. It is expected that the efficacy of CVD101 is substantially close to 100%, since the parent strain 395 confers 100% efficacy.

Construction of CVD101 followed in general the principles outlined supra, e.g. the construction of JBK70, except that the resulting CVD101 had no resistance gene that needed curing. The final step in isolating the second and find in vivo recombinant included a scheme for selecting sensitivity to an antibiotic e.g. tetracycline sensitivity, whereas the parent strain had inserted at the location of the A gene of CT a tetracycline resistance gene. It will be understood that such antibiotic sensitivity is another example of a selectable marker.

Production of vaccine strains can be performed by a variety of methods, including the following: *Vibrio cholerae* is subcultured from stock cultures into brain/-heart infusion agar (BHIA) and grown at 37° C. overnight. Identity is tested with group-and type-specific antisera and twenty to thirty colonies are suspended in BHI broth. Preincubated BHIA plates are inoculated with BHI suspension. After incubation for five to six hours, each plate is harvested with 5 ml of sterile saline buffered to pH 7.2±0.1. Harvested organisms are centrifuged in the cold at 750 g for ten minutes, resuspended and washed twice in four-times the original volume. The suspension is standardized spectrophotometrically and diluted to approximate the number of organisms required for vaccination (ca $10^6$, which varies depending on the results of volunteer studies). Replicate, pour-plate quantitative cultures are made of the inocula before and after challenge to confirm inoculum size. The final inoculum is examined with Gram's stain and agglutinated with homologous antiserum prior to feeding.

The *Vibrio cholerae* strains of the present invention can be administered by the oral route. Two grams of $NaHCO_3$ are dissolved in five ounces of distilled water. Volunteers drink four ounces of the $NaHCO_3$/water; one minute later the volunteers ingest the vibrios suspended in the remaining one ounce of $NaHCO_3$/water. Volunteers are NPO ninety minutes pre- and postinoculation.

With regard to safety, the major concern is that the vaccine strain does not revert to toxigenicity (i.e., produce intact cholera toxin) which could cause disease. The two major assays for testing toxin are the Y-1 adrenal cell assay [Sack, D. A. et al. *Infect. Immjun.* 11, 334 (1975)] and the enzyme-linked immunosorbent assay (ELISA) [Sack, D. A. et al. *J. Clin. Micro.* 11, 35 (1980)]. The vaccine strain (JBK70) has been repeatedly tested in these two assays and found to be negative each time. Far more important, however, are the genetic assays performed for the presence of toxin genes. The DNA for cholera toxin genes can be radioactively labeled and used as a specific probe to identify other cholera toxin genes in the strain, according to the method of Southern, E. M. *J. Mol. Bio.* 98, 503 (1975). When tested by this method, the vaccine strain described in the invention possesses no detectable genetic material that can enclose cholera toxin. The vaccine has also been tested in an infant mouse model, according to Baselski, V. et al. *Infect. Immun.* 15, 704 (1977). After repeated (ten in all) serial passages, no fluid accumulation (i.e., evidence of disease has been found. As expected, JBK70 was found to colonize the infant mouse intestine.

In order to avoid undesirable side effects of the vaccine strains, such as diarrhea and nausea, cramping, and other symptoms, the vaccine strains may further comprise a second restriction endonuclease fragment of DNA coding for zonula occludens toxin (ZOT) deleted.

A culture of *Vibrio cholerae* comprises a *Vibrio cholerae* strain having a first restriction endonuclease fragment of DNA deleted to confer avirulence and retain capacity to colonize the intestine of a host animal and having a second restriction endonuclease fragment of DNA coding for zonula occludens toxin (ZOT) deleted to reduce residual diarrhea in the host animal. The first DNA fragment deleted may code for the *V. cholerae* toxin or portions thereof such as the $A_1$ subunit. One isolated deletion mutant encompasses a deletion in the ctx gene, as defined by Acc I restriction endonuclease sites, and a deletion in the zot gene. Another isolated deletion mutant encompasses a deletion in the ctx gene, as defined by Xba I and Cla I restriction endonuclease sites, and a deletion in the zot gene, as defined by Stu I and Acc I restriction endonuclease sites.

A method of isolating such deletion mutants of *Vibrio cholerae* comprises the steps of (a) constructing a first plasmid comprising *Vibrio cholerae* flanking sequences of one or more deleted restriction endonuclease fragments and a gene for a selectable marker of foreign origin ligated to said flanking sequences to substitute for and to be in place of said deleted fragment, wherein said sequences are of sufficient length to promote detectable in vivo recombination;

(b) mating a virulent strain of *Vibrio cholerae* with a first microorganism carrying the first plasmid;

(c) selecting for *Vibrio cholerae* expressing the first selectable marker;

(d) mating the selected product of step (c) with a second microorganism carrying a second plasmid with a second selectable marker, said second plasmid being incompatible with the first plasmid;

(e) selecting for *Vibrio cholerae* expressing both the first selectable marker and the second selectable marker;

(f) constructing a third plasmid comprising *Vibrio cholerae* flanking sequences of one or more deleted restriction endonuclease fragments homologous to those described in step (a) but differing in the absence of a selectable marker of foreign origin;

(g) mating the selected product of step (e) with a third microorganism carrying a third plasmid described in step (f); and (h) selecting for *Vibrio cholerae* which no longer expresses the first selectable marker.

This method may be used for ZOT minus only strains or for making a ZOT minus derivative of a strain which is already deleted for cholera toxin genes.

Another culture of *Vibrio cholerae* comprises a *Vibrio cholerae* strain having a region of the chromosomal DNA coding for cholera toxin and zonula occludens toxin (ZOT) deleted. A method of isolating such deletion mutants of *Vibrio cholerae* comprises the steps of (a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae*;

(b) mating a microorganism carrying said plasmid with a virulent strain of *Vibrio cholerae* containing said sequences to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker; and therefore have a region of the chromosomal DNA coding for cholera toxin and zonula occludens toxin deleted. Step (b) may comprise: (b) mating a microorganism carrying said plasmid with a virulent strain of *Vibrio cholerae* containing said sequences inserted between flanking identical copies of a second sequence such as RS1 elements of sufficient length to promote detectable in vivo recombination.

The *Vibrio cholerae* deletion mutants of this invention are useful in vaccination against cholera.

Herein reported is a new toxic factor elaborated by *V. cholerae* which increases the permeability of the small mucosa by affecting the structure of the intercellular tight junctions or zonula occludens (ZO) (the paracellular pathway of ion transport). Production of this factor by *V. cholerae* correlates with diarrheagenicity in volunteers. By disturbing the normal absorptive processes of the small intestine via the paracellular pathway, this factor could be responsible for the residual diarrhea induced by ctx deletion mutants of *V. cholerae* and may contribute to the severe diarrhea that distinguishes cholera from other diarrheal diseases.

Changes in intestinal function induced by three strains of *V. cholerae*, one wild type and two attenuated vaccine strains, were examined. *V. cholerae* strain 395, classical biotype, Ogawa serotype, is a highly virulent strain which has been extensively characterized in volunteer studies conducted at the Center for Vaccine Development. This strain induces diarrhea with a mean stool volume of 5.5 liters (range of 0.3 to 44 l) in greater than 90% of volunteers ingesting $10^6$ organisms [Levine, M. M. et al, *Infect. Immun.* 56, 161–167 (1988)]; [Levine, M. M., *Cholera and Related Diarrheas*, 195–203] (Karger, Basel, 1980). Cholera diarrhea is principally due to the enzymatic effects of the A subunit of CT on intestinal mucosa. The CT A subunit, encoded by ctx, stimulates adenylate cyclase and results in net secretion of fluid into the intestinal lumen. Gill, D.M. *Adv. Cyclic Nucleotide res.* 8, 85–118 (1977). *V. cholerae* vaccine strain CVD101 is a ctx deletion mutant of 395 in which 94% of the sequences encoding the $A_1$ peptide of CT have been removed. Surprisingly, although CVD101 no longer produces active CT, this strain caused mild to moderate diarrhea (mean stool volume of 0.9 l with a range of 0.3 to 2.1 l) in 54% of volunteers ingesting this organism. A second derivative of 395, vaccine strain 395N1, constructed by Mekalanos, et al., *Nature* 306, 551–557 (1983), lacks ca. 77% of the sequences encoding the $A_1$ peptide by applicants' calculation. In contrast to CVD101, 395N1 induced very mild diarrhea (0.3 l stool volume) in only 1 of 21 volunteers (P=0.002 compared to 13 of 24 volunteers with diarrhea after ingestion of CVD101). [Herrington, D. A. et al. *J. Exp. Med.* 168, 1487–1492 (1982)]. Since these strains were similar in their ability to colonize the intestine, applicants hypothesize that CVD101 produces a secretogenic factor which is expressed weakly or not at all by 395N1 and that this factor is responsible for the diarrhea seen in volunteers ingesting CVD101.

Figure 13B:
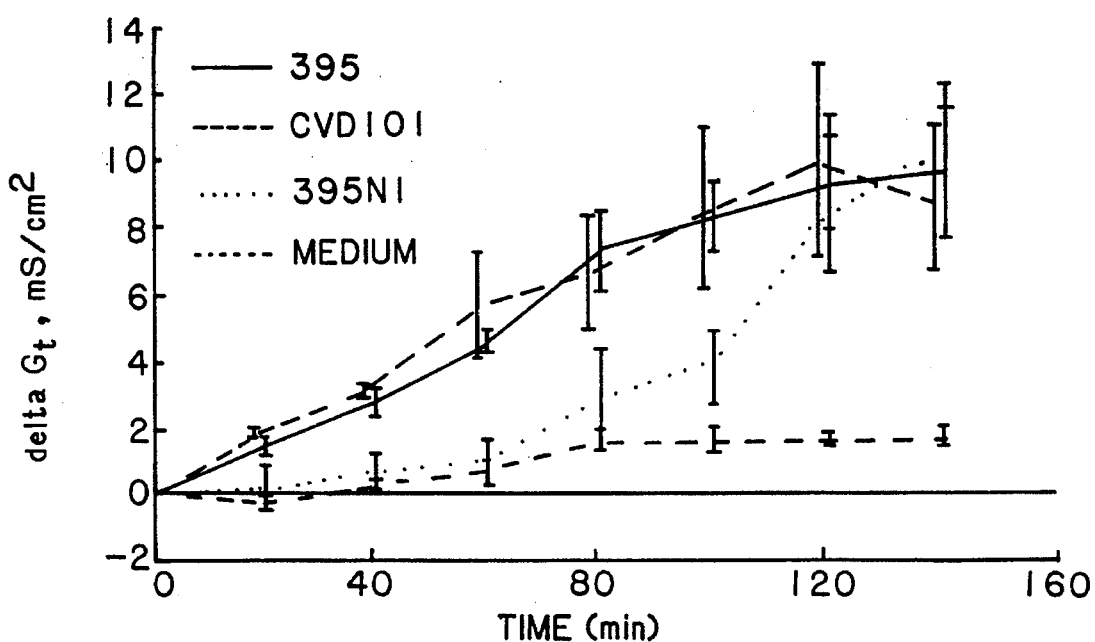
FIGS. 13A and 13B. Effect of *V. cholerae* culture supernatant on ileal short circuit current (Isc) and tissue ionic conductance (Gt). Values are means for 6 animals at each time-point; brackets are 1 standard error a, Effect of *V. cholerae* 395 supernatants on Isc (solid lines) and Gt (dashed lines). b, Effect of *V. cholerae* 395 (solid Line), CVD101 (long dashed line) and 395N1 (dotted line) supernatants on Gt. Medium control (short dashed line) consisted of uninoculated culture medium.
Figure 13A:
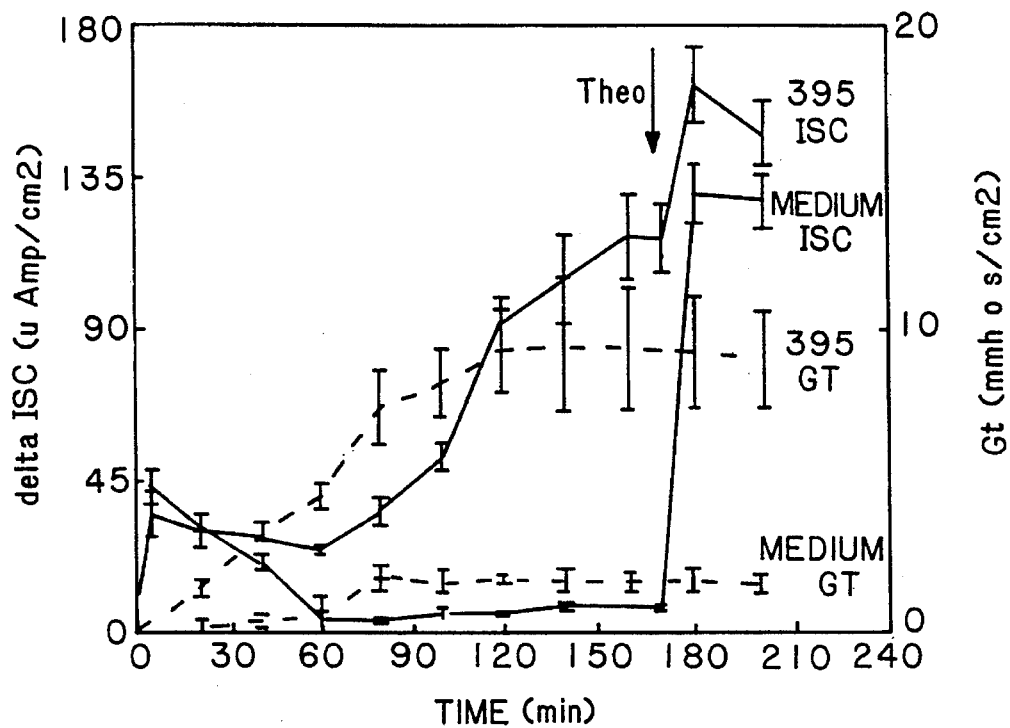
Figure 14A:
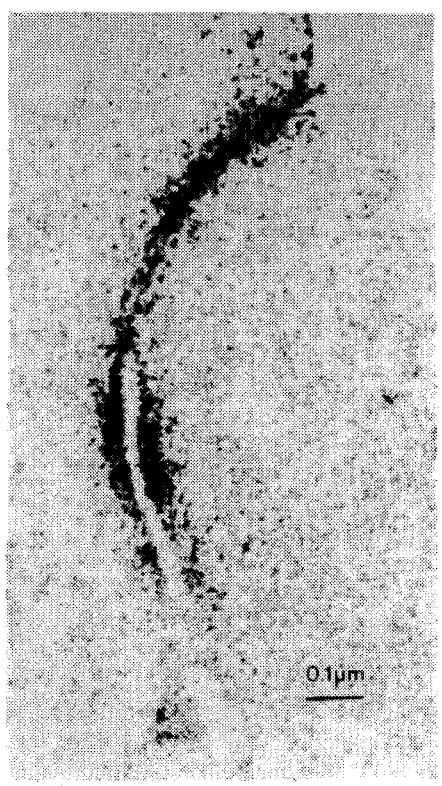
FIG. 14, panels A, B, C, and D. Wheat germ agglutinin - horseradish peroxidase (WGA-HRP) permeability assay on rabbit ileal tissues exposed to culture supernatants of various *V. cholerae* strains. a, medium control; b, *V. cholerae* 395; c, *V. cholerae* 395N1; d, *V. cholerae* CVD101.
Figure 14B:
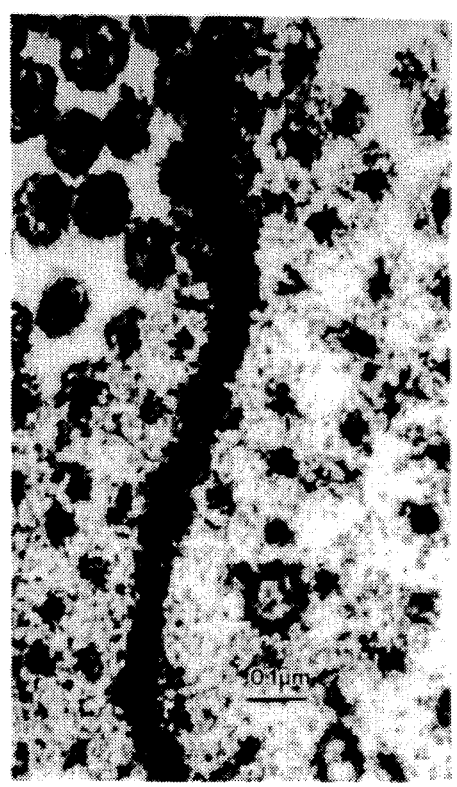
Figure 14C:
Figure 14D:

These strains were studied using rabbit intestinal tissue mounted in Ussing chambers, a classic technique for studying the transport process across intestinal tissue. Supernatants of *V. cholerae* cultures were added to the chambers and potential difference (PD) and short circuit current (Isc) were measured. PD is the difference in voltage measured on the mucosal side vs. the serosal side of the tissue and Isc is the amount of current needed to nullify the PD. From these measurements, tissue conductance (Gt) was calculated using Ohm's law: Isc=PD×Gt. Applicants first studied the effect of supernatants of the wild type strain 395 on these parameters using uninoculated culture media added to matched ileal tissue from the same animal as a negative control. FIG. 13A shows the Isc and Gt variations obtained. The initial peaks in Isc and PD that occurred in both negative controls and test samples were most likely due to the cotransport of Na and nutrients present in the media. In the negative control, Isc and PD returned to baseline values after approximately one hour and subsequently Isc, PD and Gt remained unchanged for the rest of the experiment. In contrast, tissues exposed to strain 395 supernatant exhibited a significant increase in Gt, reaching a maximum value after 2 hrs of incubation. In such samples, the Isc never returned to the baseline, but a steady state period for Isc was noted between 40 and 60 minutes. Since Isc is equivalent to PD×Gt and the observed PD after 60 min. was similar to the initial value (data not shown), the significant increase in Isc in 395-treated tissues at that time point can only be due to an increase in Gt (see FIG. 13A time 60 Min.) (12). After 60 min., Isc began to rise again along with PD in 395-treated tissues. This second phase probably reflects the effect of cholera toxin on ion fluxes since purified CT increases Isc in rabbit ileal tissue only after a lag time of at least 40 minutes. These data suggest that there are two factors expressed by *V. cholerae* 395 that can alter ion transport in Ussing chambers. One factor, cholera toxin, induces an increase in Isc and PD beginning ca. 60 minutes after addition of culture supernatant while a second factor induces an immediate increase in tissue conductance which is observable within 20 minutes after addition of culture supernatant.

Gt variation induced by culture supernatants of the attenuated *V. cholerae* strains CVD101 and 395N1 was next studied. CVD101 induced an immediate increase in Gt which was indistinguishable from that seen with 395 (FIG. 13B). In contrast, 395N1 induced no immediate increase in Gt; Gt variation in 395N1-treated tissues was similar to the negative broth control and significantly lower than that seen with 395 and CVD101 for almost 100 min of incubation. After this period, Gt modification in tissues exposed to 395, CVD101 and 395N1 were similar. These results suggest that 395N1 produces lower amounts or a less active form of the factor responsible for this increase in Gt.

Figure 15A:
Figure 15B:

Variation in transepithelial conductance reflects modification of tissue permeability through the intercellular space, since plasma membrane resistances are relatively high. Since ZO represents the major barrier in this paracellular pathway and variation in Gt is the most sensitive measure of ZO function, morphological modifications of ZO induced by *V. cholerae* 395, CVD101 and 395N1 supernatants were examined. If a low-molecular weight electron-dense marker such as wheat germ agglutinin-horseradish peroxidase (WGA-HRP) is added to the mucosal side of an epithelial sheet, it will usually not pass beyond to ZO [Alberts, B. et al., *Molecular Biology of the Cell 2nd ed* (1989)]. WGA-HRP was added to the mucosal side of intestinal tissue treated with culture supernatants of 395, CVD101, 395N1 or uninoculated broth control for 60 minutes. As seen in FIG. 14, tissues treated with uninoculated culture medium were not permeable to WGA-HRP (FIG. 14, panel A), while 395 and CVD101-treated tissues showed the entry of the stain into the paracellular space (FIG. 14, panels b and d). Tissues exposed to 395N1 supernatants were unaffected, inasmuch as the intercellular space remained tight enough to exclude the passage of WGA-HRP (15C). These results were confirmed and extended using freeze-fracture electron microscopy wherein the number of strands lying in parallel at the ZO correlates with transepithelial electrical conductance. Tissues exposed to culture supernatants showed a mixture of unaltered ZO (FIG. 15A) and altered ZO with decreased strand complexity (FIG. 15B). Strands lying perpendicular to the long axis of the ZO appeared to be preferentially lost, resulting in a decreased number of strand intersections. The complexity of the ZO exposed to each strain supernatant was quantified by measuring the density of strand intersections. As seen in FIG. 15C, tissues treated with culture supernatants of 395 or CVD101 showed a significant decrease in the number of strands and in the complexity of the reticulum of the ZO when compared to tissues treated with uninoculated broth or supernatants of 395N1.

The alterations of ZO morphology induced by 395 and CVD101 parallel the increased tissue conductance induced by these strains. The function of intestinal ZO is to regulate the paracellular pathway and restrict or prevent the diffusion of water-soluble molecules through the intercellular space back into the lumen. This diffusion is driven by concentration gradients created by the transepithelial transport processes. As a consequence of alteration of the paracellular pathway, intestinal mucosa becomes more permeable and water, Na and Cl leak into the lumen, resulting in diarrhea. The alteration of the paracellular pathway induced by *V. cholerae* 395 and CVD101 is specific for the small intestine; substitution of rabbit cecal tissue for ileal tissue resulted in no variation in Gt induced by 395 supernatant (data not shown). This is the first report of a bacterial factor which is capable of loosening tight junctions in intact intestinal tissue and may represent a new mechanism of bacterial diarrhea. *Clostridium difficile* toxin A, influenza, and vesicular stomatitis (VSV) viruses have been shown to loosen tight junctions in tissue culture monolayers but such activity in intact tissue or correlation with diarrhea have not been reported.

Figure 16:
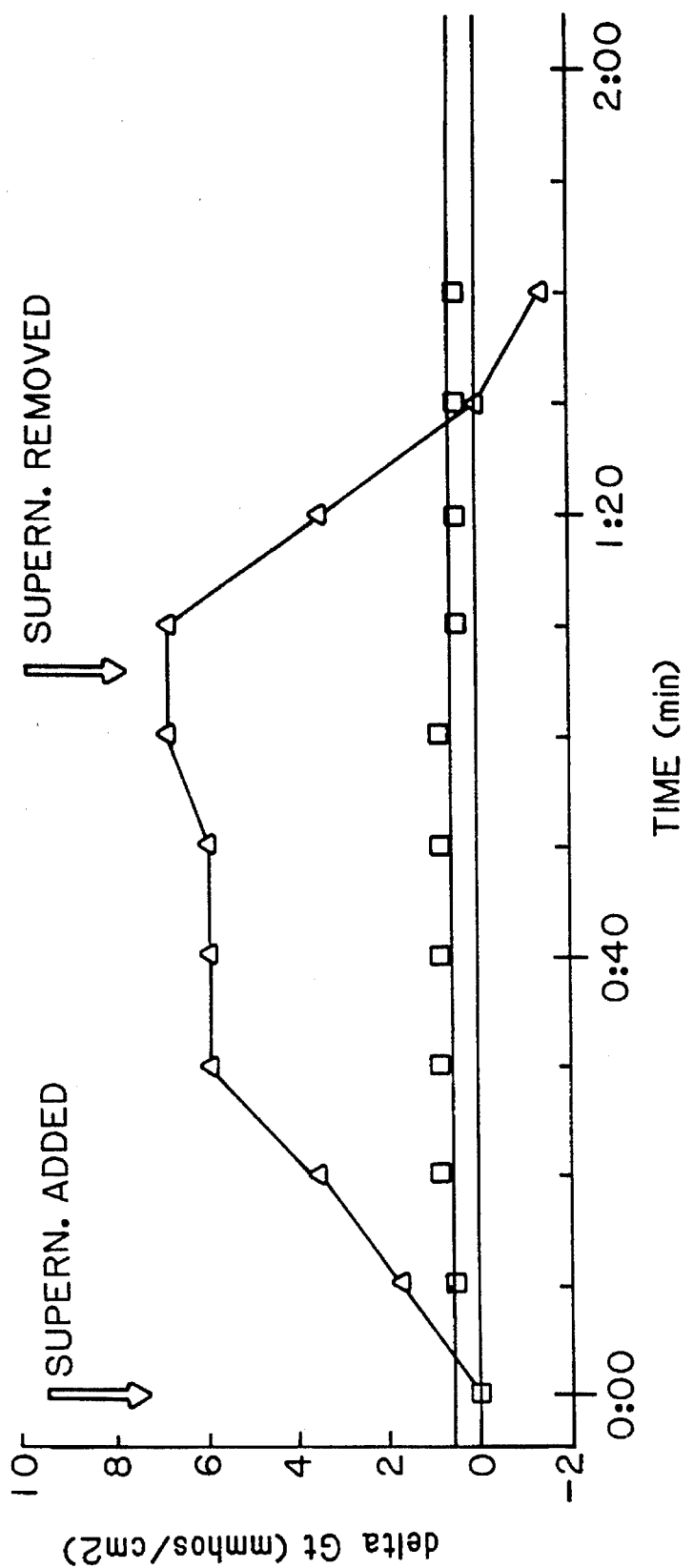
FIG. 16. Reversibility of Gt variations induced by *V. cholerae* 395 supernatant. Culture supernatants of *V. cholerae* (triangles) and uninoculated medium (squares) were added and removed at the time indicated by arrows.

Thus, *V. cholerae* 395 and CVD101 produce a factor which may be responsible for diarrhea seen in volunteers ingesting ctx deletion mutants of *V. cholerae*. The diarrhea induced by these ctx mutants is equivalent to that seen with many strains of enterotoxigenic *E. coli*. This secretogenic factor, which applicants have termed ZOT for zonula occludens toxin, induces an early increase in Isc and tissue conductance which is not related to the effects of CT on ion fluxes. This increase in Gt is associated with loosening of the tight junctions, an effect which was quickly reversed upon removal of the supernatant (FIG. 16). The quick reversal of this effect is in contrast to the long-lasting effect of CT. These results do not account for previously unexplained observations of Fields, et al., *J. Clin. Invest.* 51, 796–804 (1972) who noted an immediate increase in Isc induced by crude, but not purified CT preparations, and may account for Nishibuchi et al., *Infect. Immun.* 40, 1083–1091 (1983) who noted an early fluid accumulation (FA) unrelated to the delayed CT-induced FA in suckling mice fed *V. cholerae*. The ability of CT-negative *V. cholerae* to induce diarrhea in volunteers correlates with production of ZOT by two attenuated strains derived from the same parent strain; CVD101 (diarrheagenic) produces ZOT while 395N1 (non-diarrheagenic) produces little or no ZOT activity.

Another culture of *Vibrio cholerae* comprises a *Vibrio cholerae* strain having a region of chromosomal DNA coding for cholera toxin and zonula occludens toxin deleted, and having inserted a mercury resistance gene and DNA coding for B subunit of *Vibrio cholerae* toxin. A method of isolating such deletion mutants is also described comprising the steps of:

(a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae*;

(b) mating a microorganism carrying said plasmid with a virulent strain of *Vibrio cholerae* containing said sequences coding for cholera toxin and zonula occludens toxin inserted between flanking identical copies of a second sequence of sufficient length to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker, and therefore have a region of the chromosomal DNA coding for cholera toxin and zonula occludens toxin deleted;

(f) constructing a second plasmid comprising a mercury resistance gene and DNA coding for B subunit of *Vibrio cholerae* toxin and a gene for a second selectable marker of foreign origin wherein said plasmid is incapable of replicating extrachromosomally in *Vibrio cholerae*, and wherein sequences of sufficient length to promote detectable in vivo recombination flank said mercury resistance gene and DNA coding for B subunit of *Vibrio cholerae* toxin;

(g) mating a microorganism carrying said second plasmid with said *Vibrio cholerae* recited in step (e) containing sequences homologous to said sequences of sufficient length to promote detectable in vivo recombination;

(h) selecting for *Vibrio cholerae* expressing said second selectable marker;

(i) growing the selected product of step (h) in the absence of the second selective agent;

(j) selecting for *Vibrio cholerae* which no longer express the second selective marker; and (k) screening said *Vibrio cholerae* recited in step (j) for *Vibrio cholerae* that have a mercury resistance gene and DNA coding for B subunit of *Vibrio cholerae* toxin and have a region of chromosomal DNA coding for cholera toxin and zonula occludens toxin deleted.

This method for isolating deletion mutants of *Vibrio cholerae* having a region of chromosomal DNA coding for cholera toxin and zonula occludens toxin deleted, and having inserted a mercury resistance gene and DNA coding for B subunit of *Vibrio cholerae* may use in step (f) flanking sequences of sufficient length comprising a gene that can be disrupted without affecting colonization and immunity of *Vibrio cholerae*. An example is the hemolysin gene. *V. cholerae* CVD110 was constructed according to this method, and has a region of chromosomal DNA coding for A and B subunits of cholera toxin and zonula occludens toxin deleted, and has a mercury resistance gene and DNA coding for B subunit of *Vibrio cholerae* toxin inserted at the site of hemolysin gene. Other examples of sequences of sufficient length comprise the his gene (Hone, Microbial Pathogenesis 5, pp. 407–478 (1989)) and the nanH gene (Vimr, J. of Bacteriology 170, pp. 1495–1504 (1988)).

In the examples that follow, any of the techniques, reactions, and separation procedures are already well known in the art. All enzymes, unless otherwise stated, are available from one or more commercial sources, such as New England BioLabs——Beverly, Mass.; Collaborative Research——Waltham, Mass.; Miles Laboratories——Elkhart, Ind.; Boehringer Biochemicals Inc.——Indianapolis, Ind.; and Bethesda Research Laboratory——Rockville, Md.., to mention a representative few. Buffers and reaction conditions for restriction enzyme digestion are used according to recommendations supplied by the manufacturer for each enzyme, unless indicated otherwise. Partial digestions with restriction enzymes are carried out using a reduced enzyme concentration which must be predetermined from preliminary experiments for each enzyme batch. Standard methodology for other enzyme reactions, gel electrophoresis separations, and *E. coli* transformation may be found in *Methods in Enzymology* Volume 68, Ray Wu, editor, Academic Press (1979). Another standard reference is Maniatis, T. et al. *Molecular Cloning*, Cold Spring Harbor (1982). Bacteria were grown according to procedures generally described in Miller, *Experiments in Molecular Genetics*, Cold Spring Harbor Laboratory (1972) *Vibrio cholerae* were propagated according to procedures generally described in Lennett, E. A. et al., eds., *Manual of Clinical Microbiology* 3rd Edition, American Society of Microbioloy, Washington (1980). *E. coli* and *V. cholerae* were mated according to procedures generally described in Johnson, Steven R. et al. *J. Bact.* 137, 531 (1979); and Yokata, T. et al. *J. Bact.* 109, 440 (1972).

The strains of this invention have been deposited at the American Type Culture Collection, located in Rockville, Md.7, prior to execution of the present application. The strains deposited are *V. cholerae* JBK56, *V. cholerae* JBK70, *V. cholerae* N1696, *V. cholerae* JVK70 (pJBK51), V. cholerae Ogawa 395, CVD101, CVD109, *V. cholerae* E7946, and *E. coli* SM10 lamda pir pCVD51, *V. cholerae* CVD110, and *E. coli* SY327 lamda pir (pCVD622.2B), which have ATCC accession numbers 39,317, 39,318, 39,315, 39,316, 39,541, 39,540, 55,057, (deposited Jun. 4th, 1990), 55,056 (deposited Jun. 4th, 1990), 68,335 (deposited Jun. 5th, 1990), 55188 (deposited Jun. 3rd, 1991), and 68630 (deposited Jun. 3rd, 1991, respectively.

EXAMPLE 1

Figure 4:
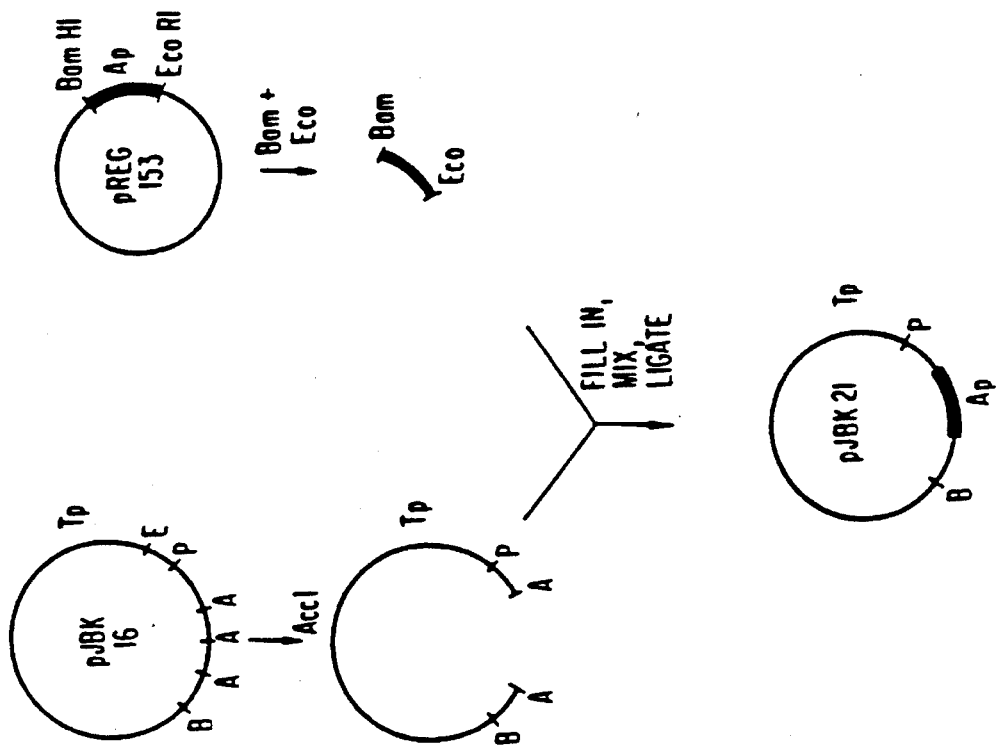
FIG. 4. Scheme for construction of JBK21.
Figure 7:
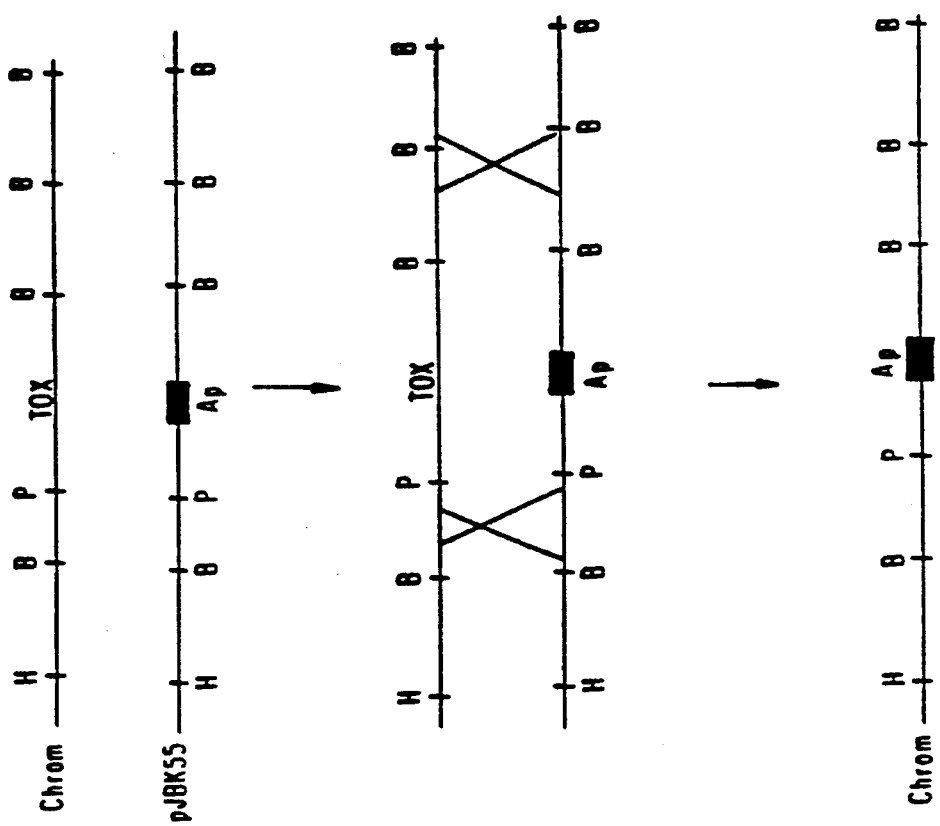
FIG. 7. Recombination in vivo by cross over and elimination of ctx gene.
Figure 6:
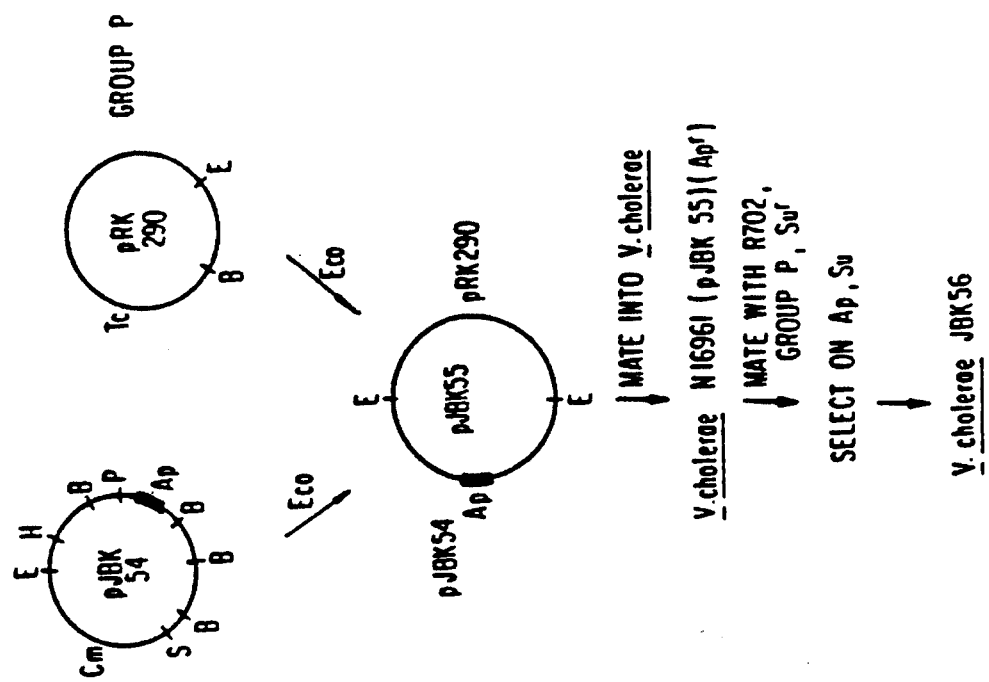
FIG. 6. Scheme for construction of *V. cholerae* JBK56.
Figure 8:
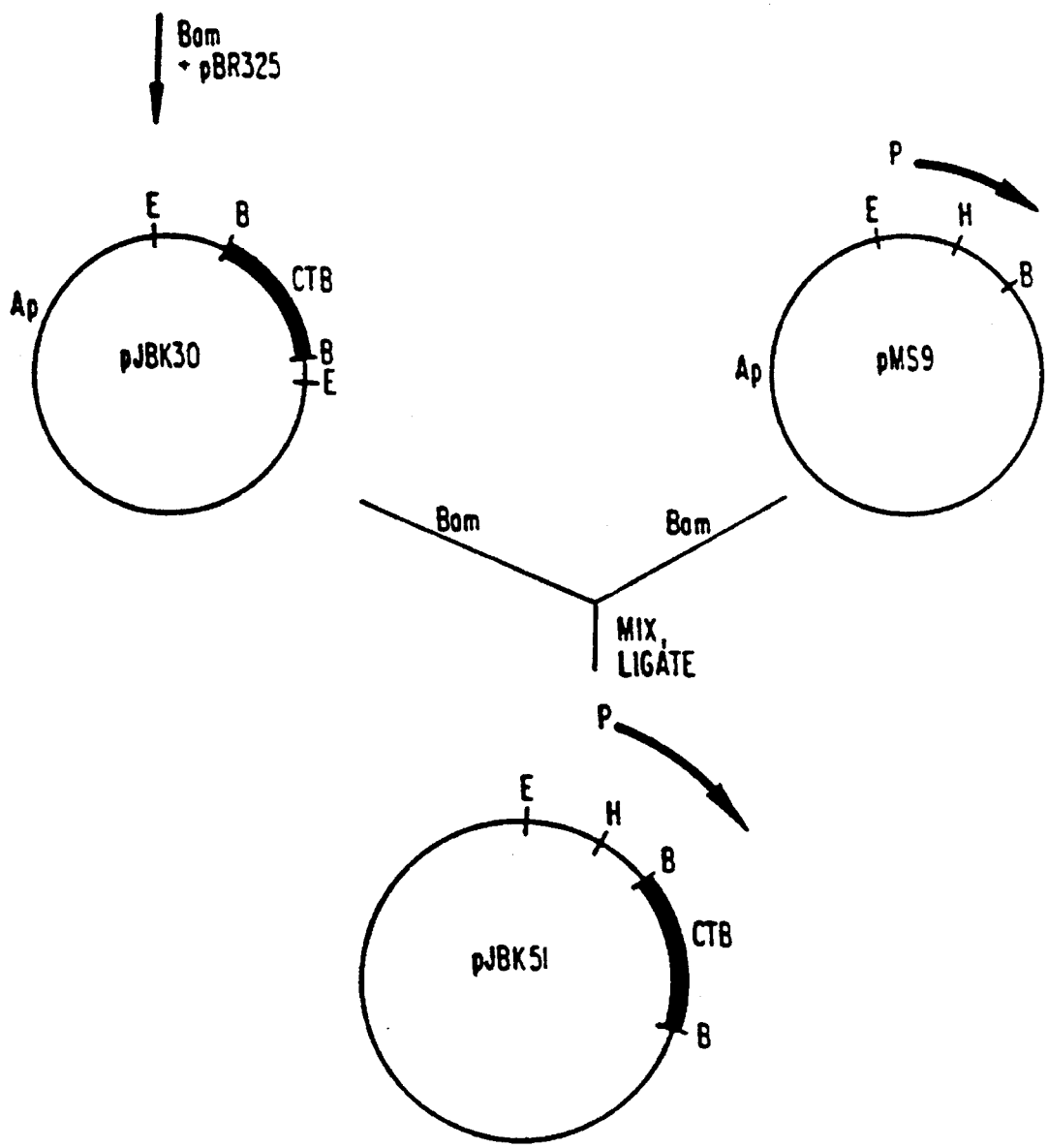
FIG. 8. Scheme for construction of pJBK51.

Construction of a Plasmid Having a Selectable Marker Gene Inserted to Replace the Toxin Genes The plasmid JBK16 contains a 4 kb PstI -Bgl II fragment of the chromosome containing the toxin genes. The toxin genes are flanked by Acc I sites and contain an internal Acc I site. JBK16 was digested to completion with Acc I and the Acc I fragments containing the toxin genes were separated from the rest of the plasmid. The remaining overlapping or "sticky" Acc I ends were made blunt-ended by "filling in" with the Klenow fragment of *E. coli* polymerase (i.e., the single-stranded DNA remaining after Acc I digestion were made double-stranded with flush ends). A gene encoding ampicillin resistance was purified from the plasmid pREG153 (pREG153 is a derivative of pREG151 [Weiss, A. et al. *J. Bact.* 152, 549–552] altered by substitution of ampicillin resistance for trimethoprin resistance and addition of cos sequences) and the "sticky" ends "filled in" as above. This fragment was then ligated to the vibrio DNA so that the Ap resistance genes were in exactly the same place as the now-deleted toxin genes, flanked by the same vibrio sequences. The resulting plasmid was designed pJBK21 (FIG. 4) containing the deletion toxin region and the Ap resistance gene.

EXAMPLE 2

Addition of Flanking Homologenous Sequences, Followed by Conjugal Gene Transfer into V. *Cholerae*

To insure the specific insertion into the chromosome of the deletion in pJBK21, approximately 7,000 bp of additional DNA was added to each end of the Pst-Bgl II fragment from pJBK21. (The probability of the homologous recombination event occurring increases with increasing length of flanking homologous sequences.) To achieve this, an approximately 18 kb fragment was cloned from the chromosome of N16961. This clone was designated pJBK44 and contains the 4 kb Pst-Bgl tox gene fragment flanked by approximately 7 kb of DNA on each side (see FIG. 5). The plasmid pJBK21 was partially digested with Pst I so that only one of the Pst sites would be cut (an additional Pst side was added within the ampicillin resistance gene) followed by digestion with Bgl II to isolate the 4 kb Pst-Bgl II fragment containing the deletion toxin region and the Ap resistance region. The plasmid pJBK44 containing the ca 18 kb Vibrio fragment was partially digested with Blg II so that only one of the 4 Bgl II sites present would be cut. This partial digestion was followed by complete digestion with Pst I and the resulting fragments separated by electrophoresis through 0.3% agarose. The separated fragments were then purified and analyzed and one fragment was found which contained all of the sequences of pJBK44 except for the 4 kb. Pst-Bgl tox gene fragment (see FIG. 5.). This fragment representing the flanking DNA was then mixed ligated to the Pst-Bgl fragment from pJBK21 containing the ampicillin resistance. The resulting plasmid, pJBK54, contained approximately 17 kb of Vibrio chromosome with an ampicillin resistance gene substituted for the deleted toxin genes.

The modified chromosomal region was then cloned into a plasmid which can be readily mobilized in *V. cholerae*. The plasmid pRK290 [Ditta, G. et al. *Proc. Nat. Acad. Sci.* 77, 7347 (1980)] belongs to the plasmid incompatibility group P and possesses a single Eco RI site into which pJBK54 was cloned (FIG. 6). The resulting plasmid pJBK55 was then mated into *V. cholerae* N16961 using the conjugative plasmid pRK2013, yielding *V. cholerae* N16961 (pJBK55) ($Ap^r$).

EXAMPLE 3

Recombination in vivo

The mutant toxin genes, after conjugal gene transfer as described in Example 2, now existed extrachromosomally in *V. cholerae* strain N16961 (see FIG. 1). At a very low frequency (perhaps $10^{-6}$ to $10^{-8}$) the homologous flanking sequences base pair and cross over into the chromosome (see FIG. 7). This rare event will result in the substitution of the deleted toxin region on the plasmid for the ctx genes on the chromosome. To select for this rare event, the plasmid incompatibility phenomenon was exploited [Ruvkin, G. B., supra]. Plasmids can be divided into incompatibility groups, designated A through W, on the basis of their ability to be stably maintained together in the same cell. If two plasmids cannot be stably maintained together in the same cell, they are incompatible and belong to the same incompatibility group presumably because they utilize the same replication mechanism in the cell. By selectively using an antibiotic resistance present on one plasmid but not on the other, it is possible to select which of two incompatible plasmids will be maintained. The plasmid pJBK55, because of its pRK290 origin, belongs to the (Inc) group P. The plasmid R702 also belongs to the Inc P group and encodes resistance to kanamycin, tetracycline, sulfonamide, and streptomycin, but not ampicillin. By mating pR702 ($Su^R$) into N16961(pJBK55)($Ap^R$) and selecting on media containing both ampicillin and sulfonamide, selection was made for cells in which the ampicillin resistance had been incorporated into the chromosome and sulfonamide resistance remains on the plasmid R702, since pR702 and pJBK55 are incompatible (see FIG. 2). The resultant strain JBK56 (FIG. 3) was ampicillin resistant, and toxin negative when tested in Y-1 adrenal cells and by $Gm_1$ ELISA. Furthermore, when chromosomal DNA was hybridized to DNA probes containing clone cholera toxin (CT) genes, JBK56 was negative, suggesting that the toxin genes were completely deleted.

The antibiotic resistance encoded on R702 was eliminated by selecting a spontaneously cured derivative lacking the plasmid (this occurred at a frequency of about 1 in 2,000).

EXAMPLE 4

Elimination of the Selectable Marker of Example 1

To eliminate the ampicillin resistance, a derivative of pJBK55 was constructed in which genes encoding resistance to mercury ($Hg^r$) from R100 were cloned into the Pst site of the Ap gene, thereby insertionally inactivating the ampicillin resistance. This derivative was then mated into *V. cholerae* JBK56, followed by pR702 and selection made as above for $Hg^r$, $Ap^s$ *V. cholerae*. The final strain, *V. cholerae* JBK70, is sensitive to all antibiotics tested, resistant to mercury, and phenotypically toxin negative. Its chromosomal DNA did not detectably hydridize to DNA probes containing CT genes. Short of sequencing the DNA for the entire chromosome, JBK70 appears to be unaltered from the parent strain N16961 except for the deletion of the toxin genes and insertion of mercury resistance and inactive ampicillin resistance genes. Such a strain cannot revert to toxigenicity because the toxin genes are not merely mutated but are completely deleted.

EXAMPLE 5

Conjugal Gene Transfer to Confer Antitoxic Immunity

If both antibacterial immunity and antitoxic immunity are desired for synergy, a derivative of JBK70 can be made to produce the B subunit of cholera toxin only. To accomplish this end, a toxin derivative was made that produces B only and lacks the genes for A (FIG. 8). A Hpa II fragment from pJBK16 containing the B structural gene was cloned into a phage cloning vector, M13mp7 placing a Bam HI and an Eco RI site on either side of the gene (FIG. 8). The fragment, now flanked by Bam HI sites was cloned into pMS 9 which contains the very strong trp promoter. The placing of the B genes under the transcriptional control of a strong promoter insures high production of B antigen. Of the clones examined, approximately 50% produced no antigen. This finding reflects the two possible orientations for the cloned insert——one forward, one backward. One derivative, pJBK51, which produced B subunit was mated into *Vibrio cholerae* JBK70 and found to produce even more B antigen then the parent strain N16961, yielding JBK70 (pJBK51). Other B0only mutants have been created using different promoters, including the $P_L$ promoter and these can be evaluated in appropriate models for any significant in vivo expression differences.

EXAMPLE 6

Colonization of Infant Mouse Intestine with JBK70 without Reversion to Toxigenicity Suckling mice (2.0–3.5 g.) were removed from their mothers and starved for 3 to 8 hours. Four of them were then inoculated on day 1 per os to stomach using a 22 g animal feeding needle. The inoculum was about $10^8$ CFU (colony-forming units)/mouse of JBK70 in a volume of between 0.05 ml and 0.1 ml. The inoculum was prepared in BHI broth essentially as described in Baselski, V. et al, supra. The inoculum contained about 0.01% Evans blue dye. The presence of this dye in the stomach, seen through the abdominal wall, indicated proper delivery of the inoculum. Addition of Evans blue dye was discontinued after day 1 (see Table I), to avoid inhibition of JBK70.

Subsequent inoculations involved mouse-to-mouse (MXM), or alternatively, mouse-to-plate-to-mouse (MXPXM), but required different procedures to prepare the inoculum compared to the Baselski protocol for the inoculation on day 1.

To prepare MXM inoculum, the gut was dissected from stomach to anus under sterile precautions. The gut was weighed, placed in a glass homogenizer tube, and about 0.5 ml BHI broth added. The mixture was homogenized briefly with a Teflon pestle until tissue was liquified. The resulting suspension was used to inoculate about $10^{-8}$ CFU into each infant mouse. It was checked for purity by streaking on MEA (meat extract agar) plates. No Evans blue dye was added.

To prepare MXPXM inoculum, a sterile loop was used to transfer cells from an MEA plate to BHI broth. About $10^{11}$ CFU/ml were added to about 1 ml of BHI so that a dense suspension was formed. The mixture was vortexed to homogeneity, and 0.05–0.1 ml. (about $10^{10}$ CFU) inoculated per os into each infant mouse. No Evans blue dye was added.

For all inoculations, mice were held in beakers at room temperature of 73°–76° F. Beakers were placed in a plastic box which was loosely covered in order to maintain the mice at slightly above ambient temperature, about 78° F.

As the results in Table I indicated, there were sufficient cells in the intestine to inoculate the next animal, as checked by streaking on MEA plates. The Vibrio cholerae JBK70 therefore colonized the gut of infant mice. Furthermore, the fluid accumulation levels did not increase since there were no substantial increases in the FA ration (an FA ratio greater than or equal to 0.065 is a positive fluid accumulation). Evidence of reversion to toxigenicity would have indicated otherwise.

EXAMPLE 7

Construction of V. cholerae strain CVD101 having a Restriction Fragment Deletion within the Gene coding for the A Subunit Another classical strain chosen for attenuation was Vibrio cholerae Ogawa 395 (alternatively designated "395") which, like N16961, has been extensively studied in volunteers and confers solid immunity [Levine, M. M. "Immunity to cholera as evaluated in volunteers," in Cholera and Related Diarrheas: 43rd Nobel Symposium, Stockholm 1978. (O. Ouchterlong & J. Holmgren, eds.) Basel: S. Karger, pp. 195-2-3 (1980); Levine, M. M et al. Acute Enteric, supra (1981)]. The procedure employed in the attenuation of 395 was not substantially different from that employed for N16961 (as described in Examples 1–5).

The first step involved the cloning and mapping of the two toxin gene copies of 395. Southern blot analysis revealed two Hind III fragments of about 16 and about 12 kb in length, both of which hydridized with cloned cholera toxin genes. These fragments were purified by agarose gel electrophoresis and cloned into alkaline phosphates treated-Hind III digested pBR325 (FIG. 9). The resulting recombinant plasmids containing the toxin genes were designated pCVD14 and pCVD15.

Plasmids pCVD14 and pCVD15 were then mapped with restriction endonucleases. A Xba I-Cla I fragment of about 550 bp was found, containing the entire base sequence of the $A_1$ subunit with the exception of codons for the first 10 amino acid residues of $A_1$. This Xba I-Cla I fragment was deleted in vitro from both pCVD14 and pCVD15 in a series of steps as shown in FIG. 10 for pCVD15. First, partial digestion with Cla I yielded a population of linear molecules in which only one of five Cla I sites was cut. Next, the ends of the linear molecules were made blunt-ended by filling in with DNA polymerase. Xba I linkers were ligated onto the blunt-ended Cla I sites yielding a collection of molecules to which a Xba I enzyme was added to trim the linker, and a tetracycline resistance gene on a Xba I fragment was added and ligated. After transformation into E. coli K-12 and selection on tetracycline, the plasmid content of a number of transformants was examined. A variety of deletion mutations were found in which one or more Xba I-Cla I fragments were deleted. One deletion mutant was chosen which lacked only the 550 bp Xba I- Cla I fragment containing the $A_1$ gene. This deletion mutant, designated pCVD25 was purified, digested with Xba I and religated to delete the tetracycline resistance gene. The resulting clone, pCVD30, was negative for holotoxin as measured in Y-1 adrenal assay [Sack, D. A. et al. supra (1975)], but positive for production of B subunit, as measured by ELISA [Sack, D.A. et al. supra (1980)], and lacked the genes for $A_1$, as shown by DNA hybridization using labeled $A_1$ probe. The Hind III fragment of pCVD30 containing the toxin deletion mutation was then cloned into pJBK85, a Tc sensitive, Cm resistant derivative of pJBK108. The resulting plasmid was designated pJBK108.

Figures 11, 12:
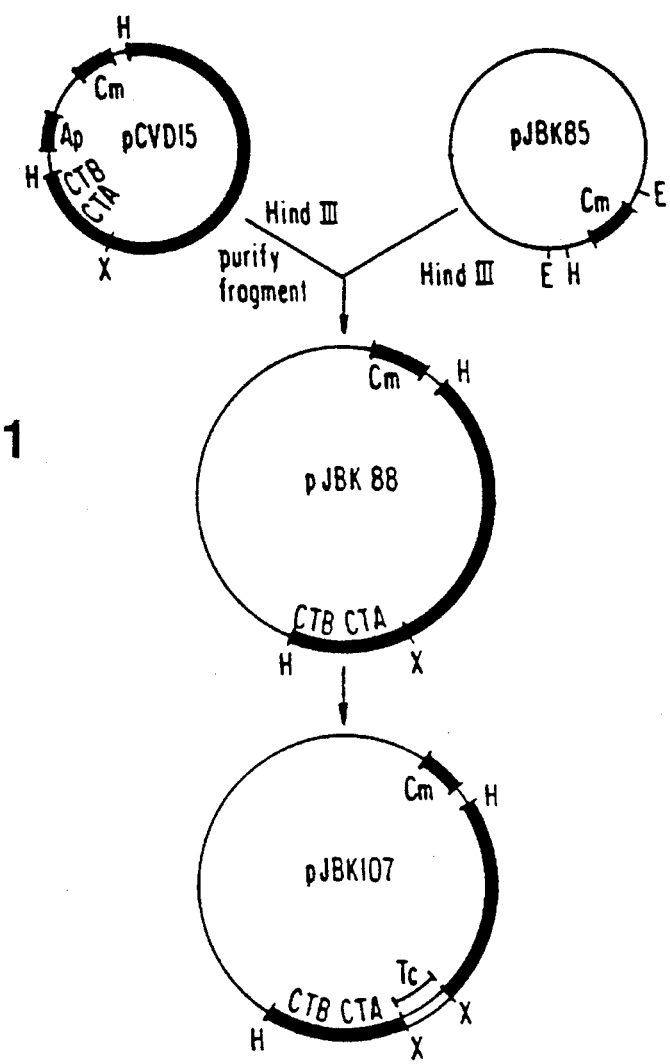
FIG. 11. Scheme for construction of pJBK107.
FIG. 12. DNA sequence of (top) the Xba I and Cla I sites, which determine the ends of the deleted Xba I-Cla I 550 bp fragment of the A subunit in Ogawa 395, and for (bottom) the junction in CVD101 after deletion of this fragment and insertion of an Xba I linker.

The lack of selectable marker in the toxin deletion mutation in pJBK108 necessitated a modification of the method previously used to attenuate El Tor N16961. To accomplish the deletion of the $A_1$ genes from 395, the Hind III fragment from pCVD15 was cloned into pJBK85, resulting in pJBK88 (FIG. 11). The tetracycline resistance gene on a Xba I fragment wa then cloned into the Xba I site within the $A_1$ gene of pJBK88, yielding pJBK107. This tetracycline resistance gene was then recombined into the chromosome of 395 as previously done for V. cholerae pJBK56. pJBK107 ($Tc^r$, $Cm^r$) was mobilized into 395 and a second Inc P plasmid, pR751 ($Tp^r$) was introduced. Selection of $Tc^r$, $Tp^r$ $Cm^s$ conomies resulted in V. cholerae JBK113, which contained tetracycline resistance genes in both chromosomal toxin gene copies. pJBK108, containing the deletion mutation, was then mobilized into V. cholerae JBK113. Homologous recombination of the deletion mutation into the chromosome will result in the loss of the $A_1$ gene sequences, an event which can be detected by loss of tetracycline resistance. Because the recombination even occurs at a very low frequency, an enrichment procedure for tetracycline sensitive cells in a population of tetracycline resistant cells was employed. This enrichment procedure exploited the fact that tetracycline is a bacteriostatic antibiotic whereas ampicillin and D-cyclo-serine are bactericidal. Therefore, a culture of *V. cholerae* JBK113 containing pJBK108 was grown for 3 hr at 37° in L-broth containing 2 micro g/ml tetracycline, 50 micro g/ml ampicillin and 50 micro g/ml D-cycloserine. At the end of 3 hours, most of the tetracycline resistant cells were killed, and tetracycline sensitive cells were detected by plating onto L-agar and replica plating onto L-agar with tetracycline. Tetracycline sensitive colonies were probed for the presence of $A_1$ genes by DNA hybridization. One tetracycline sensitive strain having deletions for both gene copies of the $A_1$ subunit was designated *V. cholerae* CVD101 and tested for production of B subunit by ELISA [Sack, supra]. *V. cholerae* CVD101 was found to produce B subunit antigen at levels substantially equivalent to the toxigenic parent *V. cholerae* 395.

EXAMPLE 8

DNA sequence of the Toxin Genes

The entire DNA sequence of the toxin genes of *V. cholerae* Inaba 62746 has been determined, part of which has been reported by Lockman, et al., *J. Biol. Chem.* 258, 13722 (1983). The restriction endonuclease mapping of pCVD14 and pCVD15 indicates that the sequences found in strain 62746 are also present in the toxin genes of 395. The predicted junction after deletion of the 550 bp Xba I-Cla I fragment, but with addition oa a Xba I linker sequence, is shown in FIG. 12. The Xba I site of the cholera toxin sequence spand amino acid residues 10 and 11 of the $A_1$ structural gene (not counting the 18 amino acid leader sequence for $A_1$.

EXAMPLE 9

Construction of a *V. Cholerae* Strain Having a Zonal Occludens Toxin Deletion in CVD101

A zot deletion mutant of *V. cholerae* is prepared in the same way as the CVD101 cholera toxin deletion mutant described in Example 7. The zot gene is contained in the recombinant plasmid pBB68. pBB68 consists of an Eco RI-Pbr I chromosomal DNA fragment from *V. cholerae* 569B which contains the zot gene and the ctx genes which have a deletion of a 550 bp Xba I-Cla I fragment. A Stu I-Acc I restriction fragment of 575 base pairs is deleted in vitro from pBB68 by digesting with the restriction enzymes Stu I and Acc I, and making the ends of the molecules blunt-ended by filling in with DNA polymerase. (This will remove 48% of the 1199 base par zot gene). One half of the sample is ligated to a tetracycline resistance gene (of foreign origin), these giving a selectable marker.

The zot deletion mutant constructed in vitro above is introduced into the chromosome of *V. cholerae* CVD101 as previously described for the construction of the ctx deletion mutant of CVD101. The tetracycline resistant clone derived above is cloned into the Inc P plasmid pJBK85. This plasmid (Tc$^r$, Cm$^r$) is mobilized into CVD101, selecting for Tc$^r$. A second Inc P plasmid, pR751 (Tp$^r$) is introduced. Selection of Tc$^r$, Tp$^r$, Cm$^s$ colonies result in *V. cholerae* strains in which the Tc$^r$ gene has recombined into the zot gene.

The plasmid containing the Stu I-Acc I deletion mutant without the Tc$^r$ gene is then mobilized into the Tc$^r$ *V. cholerae* strain. Homologous recombination of the deletion mutant into the chromosome results in the loss of the zot gene sequences, an event which can be detected by loss of Tc$^r$. Tc$^s$ colonies are selected and screened for loss of zot sequences by DNA hybridization using the Stu I-Acc I fragment as a probe.

EXAMPLE 10

Construction of CVD109- a *V. Cholera* Strain Having Restriction Fragment Deletions of Sequences coding for *V. Cholera* Toxins and for Zonula Occludens Toxin The construction of attenuated *V. cholerae* strain CVD109 (ATCC#55057) involves in introduction of cloned Vibrio sequences along with sequences encoding a selectable marker into the chromosome of a virulent *V. cholerae* strain. An initial in vivo recombination event of homologous sequences from the recombinant plasmid into the chromosome provides a selectable marker at this site. A second in vivo recombination event between homologous flanking sequences results in excision of proficient genes from the chromosome with the end product being a deletion mutation.

Figure 17:
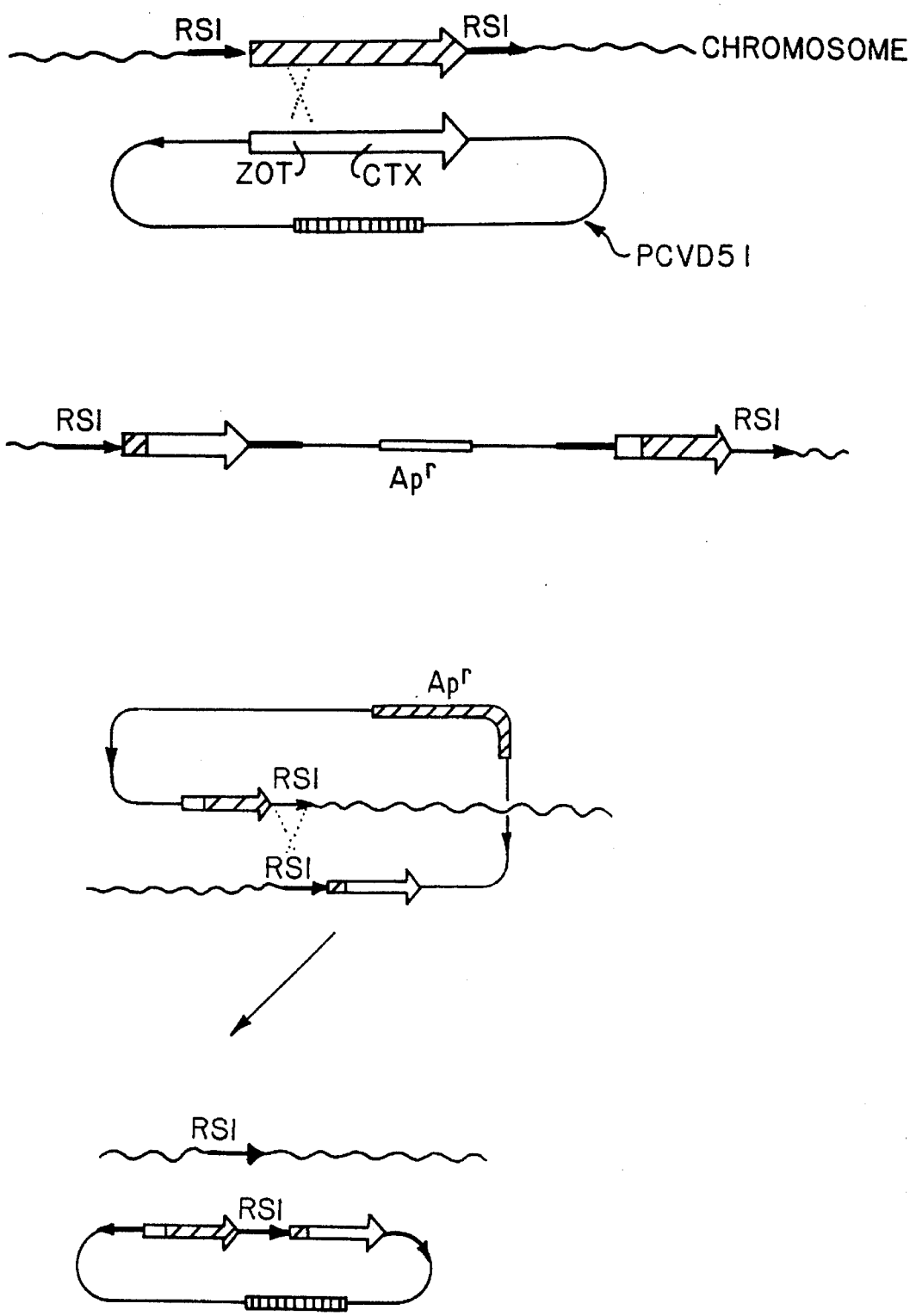
FIG. 17. Scheme for construction of CVD109. The zot and ctx genes are adjacent to each other on the *V. cholerae* chromosome and are in a region of the chromosome which contains multiple copies of a 2700 sequence sequence called RS1 (repetitive sequence). RS1 elements are on both sides of zot and ctx genes in virulent *V. cholerae* strain E7946 (El Tor biotype, Ogawa serotype). The zot and ctx genes are shown by a large open or hash-marked arrow. RS1 sequences are shown by a smaller, solid arrow.

FIG. 17 illustrates the construction of CVD109. The zot and ctx genes are adjacent to each other on the *V. cholerae* chromosome. Multiple copies of a 2700 base pair DNA sequence called RS1 (for repetitive sequence) are on both sides of the zot and ctx genes in virulent *V. cholerae* strain E7946 (El Tor biotype, Ogawa serotype). In FIG. 17A, the zot and ctx sequences are shown by a large open or hash-marked arrow. RS1 sequences are shown by a smaller, solid arrow.

The recombinant plasmid, pCVD51 (FIG. 17A), contains cloned zot/ctx sequences (open arrow) which are homologous to the chromosomal zot/ctx sequences (shown by hash-marked arrow in FIG. 17A) and contains a selectable marker, ampicillin resistance (Ap$^r$). The plasmid vector into which the Vibrio sequences were cloned is pGP704 (Miller and Mekalanos *J. Bacteril,* 170, 2575–2583 (1988)). This plasmid cannot replicate extrachromosomally in *V. cholerae* but can replicate in permissive *E. coli* strains. pCVD51 was mated from *E. coli* to *V. cholerae* E7946. Since this plasmid cannot replicate extrachromosomally in *V. cholerae*, selection of Ap$^r$ colonies yielded strains in which the entire plasmid, with the Ap$^r$ marker, was homologously recombined into the chromosome at the site of the zot/ctx sequences. (The exact site of recombination, whether in zot or ctx gene, is not known.) The result of this single cross over (not double cross over) event is termed a "cointegrate" structure and is depicted in FIG. 17B.

The RS1 sequences flanking the zot/ctx region are of sufficient length to provide detectable in vivo recombination; intra-molecular recombination between the homologous RS1 elements results in the loss of all sequences between them. The Ap$^r$ *V. cholerae* with the integrated plasmid was grown in the absence of ampicillin and the Ap sensitive (Ap$^s$) colonies were selected. Recombination of the RS1 elements flanking ctx and zot resulted in the loss of the intervening zot and ctx sequences along with the plasmid vector containing Ap$^r$ (FIG. 17C).

The Ap$^s$ *V. cholerae* colonies resulting from the above steps were screened by DNA hybridization for zot sequences. The DNA probe consisted of a 575 base pair Stu I - Acc I restriction fragment derived from the cloned zot gene. Colonies which did not hybridize to this probe were selected and probed for the presence of ctx genes by DNA hybridization using a ctx gene probe. The hybridization results confirmed the loss of both the zot and ctx genes. One representative strain was saved and designed CVD109. FIG. 17D depicts the chromosome of CVD109 which is deleted of zot and ctx sequences but retains one copy of the RS1 element. (The plasmid shown in 17D is not retained in the final Ap$^s$ strain but is depicted only to illustrate the outcome of the second cross-over event. This transient product is spontaneously lost since the plasmid cannot replicate extrachromosomally in *V. cholerae*.)

EXAMPLE 11

Construction of CVD110-a5 *V. Cholerae* Strain Having Restriction Fragment Deletions of Sequences Coding For A and B Subunits of *V. Cholerae* Toxin and for Zonula Occludens Toxin, and Having Inserted a Mercury Resistance Gene and DNA Coding for B Subunit of *V. Cholerae* Toxin CVD110 (ATCC#55188) was constructed directly from *V. cholerae* CVD109, the description of which has already been provided. *V. cholerae* CVD109 lacks both the A and B subunits of cholera toxin (CT) as well as the gene encoding zot and is sensitive to mercury. A gene fragment that contains the CT B subunit gene (ctxB) and a mercury resistance gene was constructed in vitro. This construction was then inserted into the chromosome of CVD109, specifically into the hemolysin gene. Thus, the final vaccine strain, CVD110, produces the B but not the A subunit of cholera toxin, is resistant to mercury and does not produce wild type HlyA protein (hemolysin).

Figure 19:
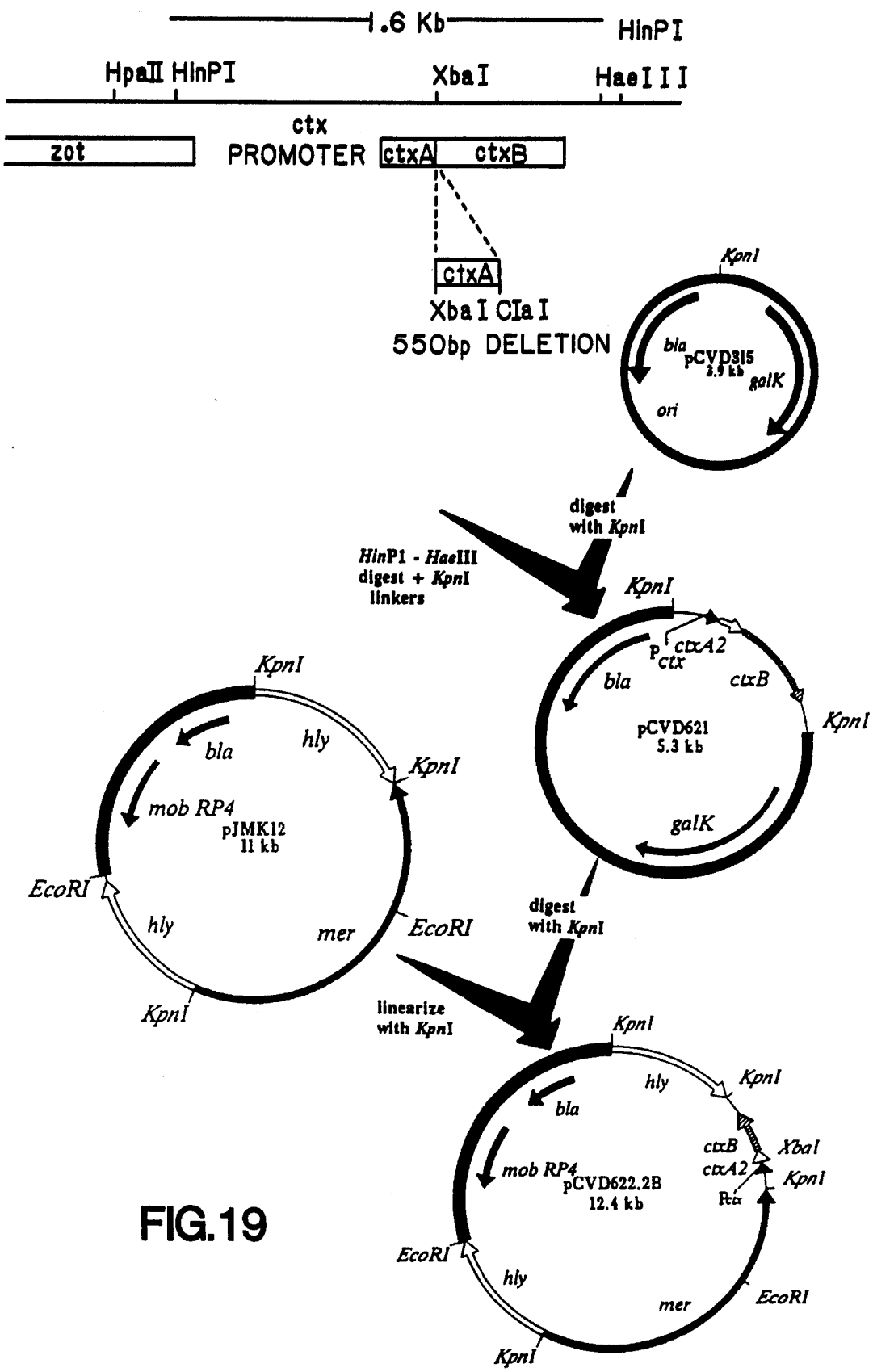
FIG. 19. Scheme for construction of plasmid pCVD621 and plasmid pCVD622.2B.

CT B construction: The ctxB and ctx promoter sequences were obtained from plasmid pCVD30, which is described in Example 7. This plasmid pCVD30 contains a deletion of the ctxA gene. A 1.4 kilobase fragment containing the ctxB gene and the ctx promoter but not the zot gene was obtained by digesting pCVD30 with Hin P1 and Hae III enzymes. The fragment was treated with T4 DNA polymerase to render the ends of this fragment blunt-ended and synthetic KpnI linkers were ligated to this fragment. The fragment was then cloned into the vector pCVD315 [Galen, et al. *Advances in Research on Cholera and Related Diarrheas*, vol. 7 (Sack et al., Eds.) pp. 143–153 (1990)] Vector pCVD315 has no particular significance for this purpose other than the presence of a Kpn I site. The resulting plasmid containing the ctxB gene was called pCVD621 (FIG. 19).

Mercury resistance genes: The source of the mercury resistance genes (mer) was the same as that used for *V. cholerae* JBK70. A 4.2 kb Nco I - Stu I fragment containing mer was originally derived from pDB7 [Barrineau, et al. *J. Molecular & Applied Genetics* (1984) vol. 2, pp. 601–619]. The fragment was treated with DNA polymerase (Klenow fragment) to render the ends of this fragment blunt-ended and synthetic Kpn I linkers were ligated to this fragment. The fragment was then cloned into plasmid pCVD43.2 (unpublished), which is a derivative of pCVD43 [Kaper, et al. *Advances in Research on Cholera and Related Diarrheas*, vol. 6 (Ohtomo, et al., Eds.) pp. 161–167 (1988)]. pCVD43 contains the cloned hemolysin genes (hlyA) of *V. cholerae* without a 400 bp Hpa I fragment internal to hlyA. The deletion of the 400 bp Hpa I fragment renders the gene inactive [Kaper, et al. Advances, etc. vol. 6]. pCVD43.2 is identical to pCVD43 except that a synthetic Kpn I linker has been ligated into the single Hpa I site of pCVD43. The combined clone of the mer genes inserted into the hylA gene is called pCVD43.3.

Insertion of ctxB and mer genes into CVD109: To introduce these genes into the chromosome of CVD109, plasmid vector pGP704, which is described in Example 10, was used. An 8.1 kb Cla I - Bgl II fragment from pCVD43.3 containing mer and hylA was cloned in pGP704 to produce pJMK12 (FIG. 19). pJMK12 was partially digested with Kpn I to yield a population of linear molecules in which only one of 3 Kpn I sites was cut. The 1.4 kb fragment of pCVD621 (described above) containing the ctxB gene was then ligated to pJMK12 to yield pCVD622.2B. The relative position and orientation of the inserted genes is shown in FIG. 19.

pCVD622.2B was then introduced into *V. cholerae* CVD109 by conjugation from an *E. coli* host strain. As described in Example 10, pGP704 cannot replicate extrachromosomally in *V. cholerae* but can replicate in permissive *E. coli* strains. Since pCVD622.2B cannot replicate extrachromosomally in *V. cholerae*, selection of Ap$^r$ colonies [pGP704 contains a gene encoding ampicillin resistance] yielded strains in which the entire pCVD622.2B plasmid, with the Ap$^r$ marker, was homologously recombined into the chromosome at the site of the hylA gene. [It could not recombine into the ctx or zot sequences because CVD109 lacks these genes.] The result of this single cross-over (not double cross-over) event is termed a "cointegrate" structure or "merodiploid" (these terms are used interchangeably) and is depicted in FIG. 20B.

A second cross-over event can occur between the homologous hylA sequences flanking the integrated pCVD-622.2B. This second cross-over event occurs spontaneously and is detected by selection of colonies which have lost the Ap$^r$ phenotype. This second cross-over event can have one of two possible outcomes, depending upon the exact site of recombination. Both possible outcomes result in the loss of the pGP704 plasmid vector sequences and are depicted in FIGS. 20C and 20D. One outcome simply re-generates the original situation, i.e., a strain identical to CVD109 which lacks ctx, zot, and mer. The second outcome results in the lost of pGP704 sequences but the mer and ctx sequences contained within the hlyA sequences are retained. The two possible outcomes are readily distinguished by DNA hybridization using radiolabeled ctx sequences as a probe. To isolate the desired outcome, a culture of CVD109 containing the integrated pCVD622.2B was grown up in L-broth without added antibiotics. This culture was plated on nonselective L-agar plates and the resulting colonies were replicated onto Ap containing L-agar plates. Ap$^s$ colonies were then hybridized to the ctX probe and colonies possessing ctx sequences were isolated. One such colony was designated *V. cholerae* CVD110. This strain was confirmed by DNA hybridization to contain ctx and mer sequences and to also lack pGP704 sequences and the 400 bp Hpa I fragment internal to the hlyA gene. *V. cholerae* CVD110 was also confirmed to produce the B subunit of cholera toxin by ELISA [Sack, D.A. et al. supra (1980)].

DNA sequence of inserted genes: The exact DNA sequences of the inserted ctx and mer genes are known from the literature. The exact site of the hlyA gene into which these genes were inserted is also known. FIG. 21 presents the expected DNA sequence of these genes, showing the relative positions of each gene. The start and stop points of the different genes are indicated; direction of the arrows indicates direction of transcription of the gene. Only those sequences which are retained in the final construction are presented, e.g., ctxB is given but the portion of ctxA which was deleted in this construction is not shown.

EXAMPLE 12

Description of ACE (Accessory Cholera Enterotoxin)

As previously described, (Example 10, p. 48) the zot and ctx genes are on a 4.3 kb region of DNA which, in many E1 Tor strains, is flanked by copies of the RS1 sequence. For the vaccine strain CVD110, this entire region is deleted. In addition to the zot and ctx genes, there are DNA sequences encoding a third toxin, ACE. In FIG. 22, the map of this region is shown. A 2.9 kb EcoRV fragment (SEQ ID No.: 1) was cloned into the vector pCVD315 (p. 47, line 289) to produce the clone pCVD630 (shown in FIG. 22).

Figures 23A, 23B:
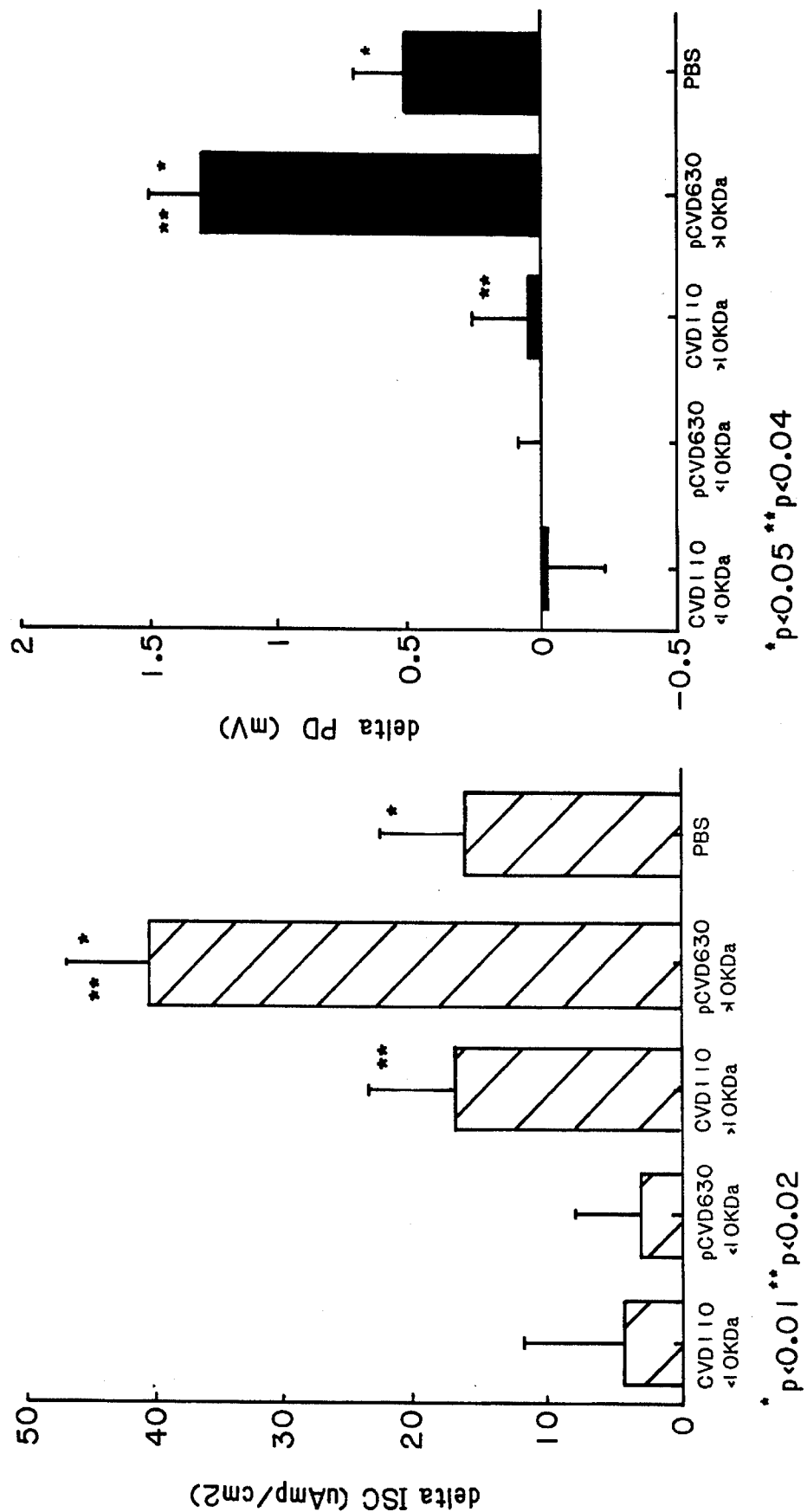

The plasmid pCVD630 was then introduced into *V. cholera* strain CVD110 and the activity of this strain in Ussing chambers was studied (Ussing chambers as previously described. Culture supernatants of CVD110 and CVD110 containing pCVD630 were tested as previously described. FIG. 23 (23A or left panel) shows the results of supernatant fractions which contained molecules less than 10 kDa in size and fractions which contained molecules greater than 10 kDa. Essentially no Ussing chamber activity was seen in the <10 kDa fraction. In the >10 kDa fraction, CVD110 produced some changes in short circuit current (Isc) but no more than the negative control, PBS (phosphate buffered saline). However, supernatants of the CVD110 (pCVD630) gave a significant increase in Isc. This difference was statistically different (p<0.02) than the result seen with CVD110 alone. As previously described, an increase in Isc can be due to either an increase in potential difference (PD) or tissue conductivity (Gt). The increase in Isc induced by the genes contained on pCVD620 is due an increase in PD, as shown in FIG. 23B.

Thus, the 4.3 kb region flanked by the RS1 elements in E1 Tor strains contains 3 putative enterotoxins. (This same 4.3 kb region is present in classical strains but RS1 sequences are found on only one side.) All three of these toxins are capable of increasing Isc in Ussing chambers using rabbit ileal tissue, an activity which correlates with diarrheagenicity in humans. Two toxins, cholera toxin and ACE, act by increasing PD while the third, ZOT acts by increasing tissue conductivity. It is desirable that all three activities are eliminated from an attenuated *V. cholera* vaccine strain to avoid the reactogenicity seen with CVD101 and other attenuated vaccine strains. CVD110 does lack all three activities and as seen in FIG. 23, produces changes in Ussing chamber comparable to changes induced by PBS (i.e. essentially no changes).

The DNA sequence of the 2.9 kb EcoRV fragment (SEQ ID No.: 1) contained in pCVD620 is shown in FIG. 24. There are two open reading frames (ORFs) immediately upstream of the zot gene. The smaller ORF immediately upstream of zot is a 297 bp ORF (ACE) which could potentially encode a protein of 11 kDa and the larger ORF immediately upstream of the 297 bp ORF is a 1185 bp ORF (OrfU) which could potentially encode a protein of 44 kDa. Ace activity is thought to be localized to the 297 bp open reading frame.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2912 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Vibrio cholerae
        ( B ) STRAIN: CLASSICAL 395

( i x ) FEATURE:
        ( A ) NAME/KEY: CDS
        ( B ) LOCATION: 1034..2218

( i x ) FEATURE:
        ( A ) NAME/KEY: CDS
        ( B ) LOCATION: 2221..2508

( x i ) SEQUENCE DESCRIPTION: SEQ ID NO:1:

```
GATATCCACT  CACGCATTAA  GTGGGCTCGT  CGTCAGGTCG  GTAAGACGTT  GTTTGATATT        60
```

-continued

| | | | | | |
|---|---|---|---|---|---|
| TCAAAGCATT | TTGGTGGTGA | TTTGGAAAGG | GTGTTTGGGG | CGTTGATTTC | TAAGGAAATT | 120 |
| CACGACGATT | CACTCAACCT | TCCAGATTCT | TATATGAAGT | TAATTGATGA | AATTATGGGT | 180 |
| GATTAATATG | AAATCTCGTT | TTGTTGTTTT | TGGTGCCTCT | CATTCTGAAG | GGGTGAGTAA | 240 |
| GACTGGTGCT | CCTTACCTTA | TCCCAGTGCT | TTTTGTTGGT | AAGCCGATTC | GCCAGTGGAA | 300 |
| AAACGATAAA | GGCCAATGTT | TGACGTTTGG | CTTGCAGCAT | CAGGAAGTGA | AATTTGTATC | 360 |
| CAGTGACGCG | ATGACCAGAA | AACTCGAACA | GACCGCCTTT | CCGGTTCTTG | TCACGTTTGA | 420 |
| CAATGAGCCA | GACCCAGAAG | ACCCATCGCG | TAACCTCGTG | ATTGATTATC | AAGTGGTGTG | 480 |
| TTCCTTGTTT | GACAACGTGC | CGGGCGCAAG | CCATTGGATA | AACCTCAACC | CATTAAATCT | 540 |
| TGATGGACTT | AACCCATTAT | GTCTGGAGCG | AGGCGCTCTA | TTTCGCGGTG | GTCAAGGCCG | 600 |
| TTCTCGTTCT | GTTCTTTACA | TCCTTTGGGA | TTGGCGCGGT | TGCCAGTCTC | ATTTTATCCA | 660 |
| CGGTAAAGGA | GAAGCTACAT | GTTTAGCTCA | CTGAAAAACA | AACTTAATAC | CTTTAAAAGC | 720 |
| ACCCTTTCAC | TCGGGGTTTT | CTTGCTGTTT | TCCGCATTTG | CTAACCAAGC | ACTCGCGGCT | 780 |
| GCTGATACGG | GTTTGGTCGC | GGAAGTCACC | AAAACACTGG | GCACCAGTAA | AGATACGGTG | 840 |
| ATTGCGCTTG | GGCCGCTTAT | CATGGGCGTG | GTGGGAGCAA | TTGTTCTGAT | TGTTACCGTG | 900 |
| ATTGGCTTAA | TTCGTAAGGC | TAAATAGTGC | TTGAGTTGTG | GCTGGGTCTC | TTTGGCTCAG | 960 |
| CGGTCATCAT | TATCGGCTTT | GTGTCGGGCT | TATATTTGGT | TTAAGGGAGG | AGGGCGAGCG | 1020 |
| TTCGCCCTTT | TTT ATG CGC TAT TTT CTA CTG TTT TTG ACA TTG CTC TTT | | | | | 1069 |
| | Met Arg Tyr Phe Leu Leu Phe Leu Thr Leu Leu Phe | | | | | |
| | 1 5 10 | | | | | |

| | | | | | | | | | | | | | | | | |
|---|---|---|---|---|---|---|---|---|---|---|---|---|---|---|---|---|
| CTT | TCT | CCA | TCG | GTA | ACA | GCT | TCC | TCC | ATC | AAT | TGT | GAT | CCT | AAT | ACT | 1117 |
| Leu | Ser | Pro | Ser | Val | Thr | Ala | Ser | Ser | Ile | Asn | Cys | Asp | Pro | Asn | Thr | |
| | | | 15 | | | | 20 | | | | 25 | | | | | |
| ACT | ACG | TCA | CAC | CAG | TTA | CTT | TTC | GGT | TTT | GGC | TCT | CCC | ATT | GTG | CAA | 1165 |
| Thr | Thr | Ser | His | Gln | Leu | Leu | Phe | Gly | Phe | Gly | Ser | Pro | Ile | Val | Gln | |
| | | 30 | | | | 35 | | | | 40 | | | | | | |
| TCG | GTG | TTA | TTT | GAT | GGC | TGC | ATG | CTT | GAT | ATT | GAA | AAA | GAT | GAC | TAT | 1213 |
| Ser | Val | Leu | Phe | Asp | Gly | Cys | Met | Leu | Asp | Ile | Glu | Lys | Asp | Asp | Tyr | |
| | 45 | | | | 50 | | | | 55 | | | | | | 60 | |
| GGT | TTT | GTT | TGG | TCT | TGT | CTC | TCA | AAT | GAA | AAT | GGG | GAC | TAT | TGC | AAG | 1261 |
| Gly | Phe | Val | Trp | Ser | Cys | Leu | Ser | Asn | Glu | Asn | Gly | Asp | Tyr | Cys | Lys | |
| | | | | 65 | | | | 70 | | | | | | 75 | | |
| GGG | CTC | TAC | AAA | CCC | CGT | TTT | ACA | CAA | GGG | GTG | TCC | CCG | AAC | TGG | CCG | 1309 |
| Gly | Leu | Tyr | Lys | Pro | Arg | Phe | Thr | Gln | Gly | Val | Ser | Pro | Asn | Trp | Pro | |
| | | | 80 | | | | 85 | | | | 90 | | | | | |
| ATG | TGC | GAC | TTG | TCC | GGA | GCA | TCT | GCA | GAG | CGC | TGC | ATT | TAT | CCT | TAT | 1357 |
| Met | Cys | Asp | Leu | Ser | Gly | Ala | Ser | Ala | Glu | Arg | Cys | Ile | Tyr | Pro | Tyr | |
| | | 95 | | | | 100 | | | | 105 | | | | | | |
| TGC | CCT | GAG | GGG | GAA | GAG | TGC | GTT | CCC | TTA | CCA | CCT | TCA | CCG | CCC | AGT | 1405 |
| Cys | Pro | Glu | Gly | Glu | Glu | Cys | Val | Pro | Leu | Pro | Pro | Ser | Pro | Pro | Ser | |
| 110 | | | | | 115 | | | | | 120 | | | | | | |
| GAT | TCC | CCT | GTT | GAT | GGG | CTG | AGC | AGC | TCG | TTT | AAG | TCT | GCG | TTC | AAT | 1453 |
| Asp | Ser | Pro | Val | Asp | Gly | Leu | Ser | Ser | Ser | Phe | Lys | Ser | Ala | Phe | Asn | |
| 125 | | | | 130 | | | | | 135 | | | | | | 140 | |
| CAG | GTC | TAT | AAA | AAC | CAA | TCA | GAG | ATG | GCT | TCG | ACT | CTC | AAT | CAT | GTC | 1501 |
| Gln | Val | Tyr | Lys | Asn | Gln | Ser | Glu | Met | Ala | Ser | Thr | Leu | Asn | His | Val | |
| | | | | 145 | | | | 150 | | | | | 155 | | | |
| AGT | GGT | CAG | GTG | TCC | CAC | TCT | CAA | GAT | ATG | GTT | CAG | CTC | AAT | ACG | AAG | 1549 |
| Ser | Gly | Gln | Val | Ser | His | Ser | Gln | Asp | Met | Val | Gln | Leu | Asn | Thr | Lys | |
| | | | 160 | | | | 165 | | | | | 170 | | | | |
| TTT | CAC | GCG | GAC | CGT | GTT | CTT | GAA | AAA | GTG | AAC | GCA | ATC | AAC | AAT | CGA | 1597 |
| Phe | His | Ala | Asp | Arg | Val | Leu | Glu | Lys | Val | Asn | Ala | Ile | Asn | Asn | Arg | |
| | | 175 | | | | 180 | | | | 185 | | | | | | |

| | | | | | | | | | | | | | | | | |
|---|---|---|---|---|---|---|---|---|---|---|---|---|---|---|---|---|
| TTG | AAT | GGG | CAG | ATA | AAC | TAT | CTT | GAA | GAA | GTT | CGC | ATC | GAT | GTA | TGG | 1645 |
| Leu | Asn | Gly | Gln | Ile | Asn | Tyr | Leu | Glu | Glu | Val | Arg | Ile | Asp | Val | Trp | |
| 190 | | | | | 195 | | | | | 200 | | | | | | |
| GAT | ACA | CAA | CGG | GAG | GTC | AGA | AAA | GCC | AAG | GAT | GAA | CTC | TCT | TCA | CGT | 1693 |
| Asp | Thr | Gln | Arg | Glu | Val | Arg | Lys | Ala | Lys | Asp | Glu | Leu | Ser | Ser | Arg | |
| 205 | | | | | 210 | | | | | 215 | | | | | 220 | |
| GTT | GGT | TCT | GTT | GCA | CAC | GAT | GTT | TAC | CAA | AGT | AAG | AAT | GCT | GTG | CTT | 1741 |
| Val | Gly | Ser | Val | Ala | His | Asp | Val | Tyr | Gln | Ser | Lys | Asn | Ala | Val | Leu | |
| | | | | 225 | | | | | 230 | | | | | 235 | | |
| CGG | GCG | ATT | GAT | GAG | CTT | AAA | GAT | TCA | CTC | GGT | GGG | GTT | GTC | GTT | CCG | 1789 |
| Arg | Ala | Ile | Asp | Glu | Leu | Lys | Asp | Ser | Leu | Gly | Gly | Val | Val | Val | Pro | |
| | | | 240 | | | | | 245 | | | | | 250 | | | |
| CCT | AAC | CCA | GAC | CAA | CCC | AAT | CCC | ACG | CCA | CCC | GAT | AGC | AGC | AGC | CCC | 1837 |
| Pro | Asn | Pro | Asp | Gln | Pro | Asn | Pro | Thr | Pro | Pro | Asp | Ser | Ser | Ser | Pro | |
| | | 255 | | | | | 260 | | | | | 265 | | | | |
| AAT | TAT | ACA | GGG | GCG | CTT | AAT | ACC | ATC | TCT | AAA | AAG | CTC | AAT | ACC | TTA | 1885 |
| Asn | Tyr | Thr | Gly | Ala | Leu | Asn | Thr | Ile | Ser | Lys | Lys | Leu | Asn | Thr | Leu | |
| | 270 | | | | | 275 | | | | | 280 | | | | | |
| GAG | ACG | ATT | TCA | CAG | CAA | CTC | GAC | ACC | ATG | AAC | ACG | GCG | CTA | TCA | GGG | 1933 |
| Glu | Thr | Ile | Ser | Gln | Gln | Leu | Asp | Thr | Met | Asn | Thr | Ala | Leu | Ser | Gly | |
| 285 | | | | | 290 | | | | | 295 | | | | | 300 | |
| CGC | TGT | AGT | AAC | CCT | GCT | CGC | TGT | CAG | TTT | CCG | ATA | CGC | GAG | GCC | GAG | 1981 |
| Arg | Cys | Ser | Asn | Pro | Ala | Arg | Cys | Gln | Phe | Pro | Ile | Arg | Glu | Ala | Glu | |
| | | | | 305 | | | | | 310 | | | | | 315 | | |
| ACC | GAG | TTA | GAA | ACG | GCT | CAG | CAG | AAT | TTA | AAG | CAG | ATG | ATC | AAC | GAT | 2029 |
| Thr | Glu | Leu | Glu | Thr | Ala | Gln | Gln | Asn | Leu | Lys | Gln | Met | Ile | Asn | Asp | |
| | | | 320 | | | | | 325 | | | | | 330 | | | |
| AAA | ATC | ACC | CAG | TCG | GCT | TTG | CAT | CAG | TTC | AAA | GGC | TCG | GCG | GCG | GTG | 2077 |
| Lys | Ile | Thr | Gln | Ser | Ala | Leu | His | Gln | Phe | Lys | Gly | Ser | Ala | Ala | Val | |
| | | 335 | | | | | 340 | | | | | 345 | | | | |
| CCT | TCG | TTT | TGC | TCC | TAT | GTC | GAG | GAG | TTT | GGT | TAC | AAC | CTC | TGT | TTC | 2125 |
| Pro | Ser | Phe | Cys | Ser | Tyr | Val | Glu | Glu | Phe | Gly | Tyr | Asn | Leu | Cys | Phe | |
| | 350 | | | | | 355 | | | | | 360 | | | | | |
| GAC | TTC | TCC | CTC | TTT | TCT | GAA | AAC | CTG | CAC | ATC | ATC | CGC | ATG | ATA | GTG | 2173 |
| Asp | Phe | Ser | Leu | Phe | Ser | Glu | Asn | Leu | His | Ile | Ile | Arg | Met | Ile | Val | |
| 365 | | | | | 370 | | | | | 375 | | | | | 380 | |
| CTC | GCG | ATG | GCG | TAC | ATT | CTG | GCC | GCC | ATG | CTC | ATT | TTG | TTT | AGG | | 2218 |
| Leu | Ala | Met | Ala | Tyr | Ile | Leu | Ala | Ala | Met | Leu | Ile | Leu | Phe | Arg | | |
| | | | | 385 | | | | | 390 | | | | | 395 | | |
| TG | ATG | CTT | ATG | ATG | GAC | CCC | CTT | TAT | GAC | TGG | CTA | ATT | GAT | GGC | TTT | 2265 |
| | Met | Leu | Met | Met | Asp | Pro | Leu | Tyr | Asp | Trp | Leu | Ile | Asp | Gly | Phe | |
| | 1 | | | | 5 | | | | | 10 | | | | | 15 | |
| ACG | TGG | CTT | GTG | ATC | AAG | CTC | GGT | ATT | ATG | TGG | ATT | GAG | AGC | AAG | ATT | 2313 |
| Thr | Trp | Leu | Val | Ile | Lys | Leu | Gly | Ile | Met | Trp | Ile | Glu | Ser | Lys | Ile | |
| | | | | 20 | | | | | 25 | | | | | 30 | | |
| TTT | GTC | ATC | CAA | TTC | TTC | TGG | GAG | ATG | TCC | CAG | AAA | GTG | ATT | GAT | ATG | 2361 |
| Phe | Val | Ile | Gln | Phe | Phe | Trp | Glu | Met | Ser | Gln | Lys | Val | Ile | Asp | Met | |
| | | | 35 | | | | | 40 | | | | | 45 | | | |
| TTT | ACC | ATC | TAT | CCG | CTT | ATC | CAA | CAG | GCT | ATC | GAT | ATG | CTG | TCT | CCT | 2409 |
| Phe | Thr | Ile | Tyr | Pro | Leu | Ile | Gln | Gln | Ala | Ile | Asp | Met | Leu | Ser | Pro | |
| | | 50 | | | | | 55 | | | | | 60 | | | | |
| CAA | TAC | AGC | GGC | TTT | CTG | TTC | TTT | TTA | GGG | TTA | GAC | CAA | GCG | CTG | GCT | 2457 |
| Gln | Tyr | Ser | Gly | Phe | Leu | Phe | Phe | Leu | Gly | Leu | Asp | Gln | Ala | Leu | Ala | |
| | 65 | | | | | 70 | | | | | 75 | | | | | |
| ATC | GTG | CTT | CAG | GCT | TTG | ATG | ACC | CGT | TTC | GCC | CTG | CGA | GCG | TTA | AAC | 2505 |
| Ile | Val | Leu | Gln | Ala | Leu | Met | Thr | Arg | Phe | Ala | Leu | Arg | Ala | Leu | Asn | |
| 80 | | | | | 85 | | | | | 90 | | | | | 95 | |
| CTA | TGAGTATCTT | TATTCATCAC | GGCGCGCCAG | GCTCTTATAA | AACGTCCGGG | | | | | | | | | | | 2558 |
| Leu | | | | | | | | | | | | | | | | |

-continued

```
GCATTATGGC TTCGTCTGCT GCCGGCGATT AAGTCAGGCC GTCACATCAT CACGAATGTG    2618

CGAGGCTTAA ACCTTGAACG CATAGCTAAG TACTTAAAAA TGGACGTCTC AGACATCAGT    2678

ATCGAGTTTA TTGATACAGA CCATCCAGAC GGTCGCTTAA CGATGGCGCG TTTTTGGCAC    2738

TGGGCGAGAA AGGACGCGTT TCTCTTTATT GATGAATGTG GTCGCATCTG GCCGCCGAGA    2798

CTGACGGCCA CCAATTTAAA GGCGCTCGAC ACGCCGCCGG ATTTGGTCGC AGAGGATAGG    2858

CCTGAGAGCT TTGAGGTGGC TTTTGACATG CATCGTCACC ACGGCTGGGA TATC          2912
```

( 2 ) INFORMATION FOR SEQ ID NO:2:

( i ) SEQUENCE CHARACTERISTICS:
        ( A ) LENGTH: 395 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Tyr Phe Leu Leu Phe Leu Thr Leu Leu Phe Leu Ser Pro Ser
 1               5                  10                  15

Val Thr Ala Ser Ser Ile Asn Cys Asp Pro Asn Thr Thr Thr Ser His
            20                  25                  30

Gln Leu Leu Phe Gly Phe Gly Ser Pro Ile Val Gln Ser Val Leu Phe
        35                  40                  45

Asp Gly Cys Met Leu Asp Ile Glu Lys Asp Asp Tyr Gly Phe Val Trp
    50                  55                  60

Ser Cys Leu Ser Asn Glu Asn Gly Asp Tyr Cys Lys Gly Leu Tyr Lys
65                  70                  75                  80

Pro Arg Phe Thr Gln Gly Val Ser Pro Asn Trp Pro Met Cys Asp Leu
                85                  90                  95

Ser Gly Ala Ser Ala Glu Arg Cys Ile Tyr Pro Tyr Cys Pro Glu Gly
            100                 105                 110

Glu Glu Cys Val Pro Leu Pro Pro Ser Pro Pro Ser Asp Ser Pro Val
        115                 120                 125

Asp Gly Leu Ser Ser Ser Phe Lys Ser Ala Phe Asn Gln Val Tyr Lys
    130                 135                 140

Asn Gln Ser Glu Met Ala Ser Thr Leu Asn His Val Ser Gly Gln Val
145                 150                 155                 160

Ser His Ser Gln Asp Met Val Gln Leu Asn Thr Lys Phe His Ala Asp
                165                 170                 175

Arg Val Leu Glu Lys Val Asn Ala Ile Asn Asn Arg Leu Asn Gly Gln
            180                 185                 190

Ile Asn Tyr Leu Glu Glu Val Arg Ile Asp Val Trp Asp Thr Gln Arg
        195                 200                 205

Glu Val Arg Lys Ala Lys Asp Glu Leu Ser Ser Arg Val Gly Ser Val
    210                 215                 220

Ala His Asp Val Tyr Gln Ser Lys Asn Ala Val Leu Arg Ala Ile Asp
225                 230                 235                 240

Glu Leu Lys Asp Ser Leu Gly Gly Val Val Val Pro Pro Asn Pro Asp
                245                 250                 255

Gln Pro Asn Pro Thr Pro Pro Asp Ser Ser Ser Pro Asn Tyr Thr Gly
            260                 265                 270

Ala Leu Asn Thr Ile Ser Lys Lys Leu Asn Thr Leu Glu Thr Ile Ser
        275                 280                 285
```

Gln Gln Leu Asp Thr Met Asn Thr Ala Leu Ser Gly Arg Cys Ser Asn
    290             295             300

Pro Ala Arg Cys Gln Phe Pro Ile Arg Glu Ala Glu Thr Glu Leu Glu
305             310             315                 320

Thr Ala Gln Gln Asn Leu Lys Gln Met Ile Asn Asp Lys Ile Thr Gln
            325             330             335

Ser Ala Leu His Gln Phe Lys Gly Ser Ala Ala Val Pro Ser Phe Cys
            340             345             350

Ser Tyr Val Glu Glu Phe Gly Tyr Asn Leu Cys Phe Asp Phe Ser Leu
        355             360             365

Phe Ser Glu Asn Leu His Ile Ile Arg Met Ile Val Leu Ala Met Ala
    370             375             380

Tyr Ile Leu Ala Ala Met Leu Ile Leu Phe Arg
385             390             395

( 2 ) INFORMATION FOR SEQ ID NO:3:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Met Leu Met Met Asp Pro Leu Tyr Asp Trp Leu Ile Asp Gly Phe Thr
1               5               10              15

Trp Leu Val Ile Lys Leu Gly Ile Met Trp Ile Glu Ser Lys Ile Phe
            20              25              30

Val Ile Gln Phe Phe Trp Glu Met Ser Gln Lys Val Ile Asp Met Phe
        35              40              45

Thr Ile Tyr Pro Leu Ile Gln Gln Ala Ile Asp Met Leu Ser Pro Gln
    50              55              60

Tyr Ser Gly Phe Leu Phe Phe Leu Gly Leu Asp Gln Ala Leu Ala Ile
65              70              75              80

Val Leu Gln Ala Leu Met Thr Arg Phe Ala Leu Arg Ala Leu Asn Leu
            85              90              95

( 2 ) INFORMATION FOR SEQ ID NO:4:

( i ) SEQUENCE CHARACTERISTICS:
        ( A ) LENGTH: 2915 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Vibrio cholerae
        ( B ) STRAIN: EL TOR
        ( C ) INDIVIDUAL ISOLATE: E7946

( i x ) FEATURE:
        ( A ) NAME/KEY: CDS
        ( B ) LOCATION: 1037..2221

( i x ) FEATURE:
        ( A ) NAME/KEY: CDS
        ( B ) LOCATION: 2224..2511

( x i ) SEQUENCE DESCRIPTION: SEQ ID NO:4:

GATAACCACT CACGCATTAA GTGGGCTCGT CGTCAGGTCG GTAAGACGTT GTTTGATATT   60

-continued

```
TCAAAGCATT TTGGTGGTGA TTTGGAAAGG GTGTTTGGGG CGTTGATTTC TAAGGAAATT      120
CACGACGATT CACTCAACCT TCCAGATTCT TATATGAAGT TAATTGATGA AATTATGGGT      180
GATTAATATG AAATCTCGTT TTGTTGTTTT TGGTGCCTCT CATTCTGAAG GGGTGAGTAG      240
TAAGACTGGT GCACCTTATC TTATCCCAGT GCTTTTTGTT GGTAAGCCGA TTCGCCAGTG      300
GAAAACGAT  AAAGGCCAAT  GTTTGACGTT  TGGCTTGCAG  CATCAGGAAG  TGAAATTTGT      360
ATCCAGTGAC GCGATGACCA GAAAACTCGA ACAGACCGCC TTTCCGGTTC TTGTCACGTT      420
TGACAATGAG CCAGACCCAG AAGACCCATC ACGCAACCTC GTGATTGATT ATCAAGTGGT      480
GTGTTCCTTG TTTGACAACG TGCCGGGCGC AAGCCATTGG ATAAACCTCA ACCCATTAAA      540
TCTTGATGGA CTTAACCCAT TATGTCTGGA ACGAGGCGCT CTATTTCGCG GTGGTCAAGG      600
CCGTTCTCGT TCTGTTCTTT ACATCCTTTG GGATTGGCGC GGTTGCTAGT CTCATTTTAT      660
CCACGGTAAA GGAGAAGCTA CATGTTTAGC TCACTGAAAA ACAAACTTAA TACCTTTAAA      720
AGCACGCTTT CACTCGGGGT TTTCTTGCTG TTTTCCGCAT TTGCTAACCA AGCACTCGCG      780
GCTGCTGATG CGGGTTTGGT CACGGAAGTC ACCAAAACAC TGGGCACCAG TAAAGATACG      840
GTGATTGCGC TTGGGCCGCT CATCATGGGC GTGGTGGGGG CAATTGTTCT GATTGTTACC      900
GTGATTGGCT TAATTCGTAA GGCTAAATAG TGCTTGAGTT GTGGCTGGGT CTCTTTGGCT      960
CAGCGGTCAT CATTATCGGC TTTGTGTCGG GCTTATATTT GGTTTAAGGG AGGAGGGCGA     1020
GCGTTCGCCC TTTTTT ATG CGC TAT TTT CTA CTG TTT TTG ACA TTG CTC         1069
              Met Arg Tyr Phe Leu Leu Phe Leu Thr Leu Leu
                1                 5                   10

TTT CTT TCT CCA TCG GTA ACG GCT TCC GCC ATC AAT TGT GAT CCT AAT       1117
Phe Leu Ser Pro Ser Val Thr Ala Ser Ala Ile Asn Cys Asp Pro Asn
              15                  20                  25

ACT ACT ACG TCA CAC CAG TTA CTT TTC GGT TTT GGC TCT CCC ATT GTG       1165
Thr Thr Thr Ser His Gln Leu Leu Phe Gly Phe Gly Ser Pro Ile Val
          30                  35                  40

CAA TCG GTG TTA TTT GAT GGC TGC ATG CTT GAT ATT GAA AAA GAT GAC       1213
Gln Ser Val Leu Phe Asp Gly Cys Met Leu Asp Ile Glu Lys Asp Asp
      45                  50                  55

TAT GGT TTT GTT TGG TCT TGT CTC TCA AAT GAA AAT GGG GAC TAT TGC       1261
Tyr Gly Phe Val Trp Ser Cys Leu Ser Asn Glu Asn Gly Asp Tyr Cys
60                  65                  70                  75

AAG GGG CTC TAC AAA CCC CGT TTT TCA CAA GGG GTA TCC CCG AAC TGG       1309
Lys Gly Leu Tyr Lys Pro Arg Phe Ser Gln Gly Val Ser Pro Asn Trp
              80                  85                  90

CCG ATG TGC GAC TTG TCC GGA GCA TCT GCA GAG CGC TGC ATT TAT CCT       1357
Pro Met Cys Asp Leu Ser Gly Ala Ser Ala Glu Arg Cys Ile Tyr Pro
          95                  100                 105

TAT TGC CCT GAG GGG GAA GAG TGC GTT CCC TTA CCA CCT TCA CCG CCC       1405
Tyr Cys Pro Glu Gly Glu Glu Cys Val Pro Leu Pro Pro Ser Pro Pro
      110                 115                 120

AGT GAT TCC CCT GTT GAT GGG CTG AGC AGC TCG TTT AAG TCT GCG TTC       1453
Ser Asp Ser Pro Val Asp Gly Leu Ser Ser Ser Phe Lys Ser Ala Phe
125                 130                 135

AAT CAG GTC TAT AAA AAC CAA TCA GAG ATG GCT TCG ACT CTC AAT CAT       1501
Asn Gln Val Tyr Lys Asn Gln Ser Glu Met Ala Ser Thr Leu Asn His
140                 145                 150                 155

GTC AGT GGT CAG GTG TCC CAC TCT CAA GAT ATG GTT CAG CTC AAT ACG       1549
Val Ser Gly Gln Val Ser His Ser Gln Asp Met Val Gln Leu Asn Thr
              160                 165                 170

AAG TTT CAC GCG GAT CGT GTT CTT GAG AGT GTC ACC GCA GTC AAC AAT       1597
Lys Phe His Ala Asp Arg Val Leu Glu Ser Val Thr Ala Val Asn Asn
          175                 180                 185
```

```
CGT TTG GGT GGG CAA ATG GAG TAT CTT GAG GAA ATC CGC ATT GAT GTT                    1645
Arg Leu Gly Gly Gln Met Glu Tyr Leu Glu Glu Ile Arg Ile Asp Val
        190                 195                 200

TGG GAT ACG CAA CGG GAG GTA AGA AAA GCC AAG GAT GAG CTT TAC TCT                    1693
Trp Asp Thr Gln Arg Glu Val Arg Lys Ala Lys Asp Glu Leu Tyr Ser
    205                 210                 215

CGT GTT GCG GCT GTT TCA TAC GAT GTG CTT TAT AGC GAG CTT AAT GTC                    1741
Arg Val Ala Ala Val Ser Tyr Asp Val Leu Tyr Ser Glu Leu Asn Val
220                 225                 230                 235

CTT CGG GCG ATT GAT GAA CTT AAA GAC TCA CTC GGT GGG ACT GTC GTT                    1789
Leu Arg Ala Ile Asp Glu Leu Lys Asp Ser Leu Gly Gly Thr Val Val
                240                 245                 250

CCG CCT AAC CCA GAC CAA CCC AAT CCC ACG CCA CCC GAT AGC AGC AGC                    1837
Pro Pro Asn Pro Asp Gln Pro Asn Pro Thr Pro Pro Asp Ser Ser Ser
            255                 260                 265

CCC AAT TAT ACA GGG GCG CTT AAT ACC ATC TCT AAA AAG CTC AAT ACC                    1885
Pro Asn Tyr Thr Gly Ala Leu Asn Thr Ile Ser Lys Lys Leu Asn Thr
        270                 275                 280

TTA GAG ACG ATT TCA CAG CAA CTC GAC ACC ATG AAC ACG GCG CTA TCA                    1933
Leu Glu Thr Ile Ser Gln Gln Leu Asp Thr Met Asn Thr Ala Leu Ser
    285                 290                 295

GGG CGC TGT AGT AAC CCT GAA CGC TGT CAG TTT CCG ATA CGA GAG GCC                    1981
Gly Arg Cys Ser Asn Pro Glu Arg Cys Gln Phe Pro Ile Arg Glu Ala
300                 305                 310                 315

GAG ACC GAG TTA GAA ACG GCT CAG CAG AAT TTA AAG CAG ATG ATC AAC                    2029
Glu Thr Glu Leu Glu Thr Ala Gln Gln Asn Leu Lys Gln Met Ile Asn
                320                 325                 330

GAG AAA ATC ACC CAG TCG GCT TTG CAT CAG TTC AAA GGC TCG GCG GCG                    2077
Glu Lys Ile Thr Gln Ser Ala Leu His Gln Phe Lys Gly Ser Ala Ala
            335                 340                 345

GTG CCT TCG TTT TGC TCC TAT GTC GAG GCG TTT GGT TAC AAC CTC TGT                    2125
Val Pro Ser Phe Cys Ser Tyr Val Glu Ala Phe Gly Tyr Asn Leu Cys
        350                 355                 360

TTT GAC TTC TCC CTC TTT TCT GAA AAC CTG CAC ATC ATC CGC ATG ATA                    2173
Phe Asp Phe Ser Leu Phe Ser Glu Asn Leu His Ile Ile Arg Met Ile
    365                 370                 375

GTG CTC GCG ATG GCG TAC ATT CTG GCC GCC ATG CTC ATT TTG TTT AGG                    2221
Val Leu Ala Met Ala Tyr Ile Leu Ala Ala Met Leu Ile Leu Phe Arg
380                 385                 390                 395

TG ATG CTT ATG ATG GAC ACC CTT TAT GAC TGG CTA ATT GAT GGC TTT                     2268
   Met Leu Met Met Asp Thr Leu Tyr Asp Trp Leu Ile Asp Gly Phe
     1               5                  10                 15

ACG TGG CTT GTG ATC AAG CTC GGT ATT ATG TGG ATT GAG AGC AAG ATT                    2316
Thr Trp Leu Val Ile Lys Leu Gly Ile Met Trp Ile Glu Ser Lys Ile
                20                 25                 30

TTT GTT ATC CAA TTC TTC TGG GAG ATG TCC CAG AAA GTG ATT GAT ATG                    2364
Phe Val Ile Gln Phe Phe Trp Glu Met Ser Gln Lys Val Ile Asp Met
            35                 40                 45

TTT ACC ATC TAT CCG CTT ATC CAA CAG GCT ATC GAT ATG CTG CCT CCT                    2412
Phe Thr Ile Tyr Pro Leu Ile Gln Gln Ala Ile Asp Met Leu Pro Pro
        50                 55                 60

CAA TAC AGC GGC TTT CTG TTC TTT TTA GGG TTA GAC CAA GCG CTG GCT                    2460
Gln Tyr Ser Gly Phe Leu Phe Phe Leu Gly Leu Asp Gln Ala Leu Ala
    65                 70                 75

ATC GTG CTT CAG GCT TTG ATG ACC CGT TTT GCC CTG CGA GCG TTA AAC                    2508
Ile Val Leu Gln Ala Leu Met Thr Arg Phe Ala Leu Arg Ala Leu Asn
80                 85                 90                 95

CTA TGAGTATCTT TATTCATCAC GGCGCGCCAG GCTCTTATAA AACGTCAGGG                         2561
Leu
```

```
GCATTATGGC  TTCGTCTGCT  GCCGGCGATT  AAGTCAGGCC  GTCACATCAT  CACGAATGTG   2621

CGAGGCTTAA  ACCTTGAACG  CATGGCTAAG  TACTTAAAAA  TGGATGTCTC  GGACATCAGT   2681

ATCGAGTTTA  TTGATACAGA  CCATCCTGAC  GGTCGCTTAA  CGATGGCGCG  TTTTTGGCAC   2741

TGGGCGAGAA  AGGACGCGTT  TCTCTTTATC  GATGAATGTG  GTCGCATCTG  GCCGCCGAGA   2801

CTGACGGTCA  CCAATTTAAA  GGCGCTCGAC  ACGCCGCCGG  ATTTGGTCGC  AGAGGATAGG   2861

CCTGAGAGCT  TGAGGTGGC   TTTTGACATG  CATCGTCACC  ACGGCTGGGA  TATC         2915
```

( 2 ) INFORMATION FOR SEQ ID NO:5:

( i ) SEQUENCE CHARACTERISTICS:
        ( A ) LENGTH: 395 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Arg  Tyr  Phe  Leu  Leu  Phe  Leu  Thr  Leu  Leu  Phe  Leu  Ser  Pro  Ser
 1              5                   10                  15

Val  Thr  Ala  Ser  Ala  Ile  Asn  Cys  Asp  Pro  Asn  Thr  Thr  Thr  Ser  His
             20                   25                  30

Gln  Leu  Leu  Phe  Gly  Phe  Gly  Ser  Pro  Ile  Val  Gln  Ser  Val  Leu  Phe
                  35                  40                  45

Asp  Gly  Cys  Met  Leu  Asp  Ile  Glu  Lys  Asp  Tyr  Gly  Phe  Val  Trp
        50                  55                  60

Ser  Cys  Leu  Ser  Asn  Glu  Asn  Gly  Asp  Tyr  Cys  Lys  Gly  Leu  Tyr  Lys
 65                  70                  75                      80

Pro  Arg  Phe  Ser  Gln  Gly  Val  Ser  Pro  Asn  Trp  Pro  Met  Cys  Asp  Leu
                   85                  90                  95

Ser  Gly  Ala  Ser  Ala  Glu  Arg  Cys  Ile  Tyr  Pro  Tyr  Cys  Pro  Glu  Gly
                  100                 105                 110

Glu  Glu  Cys  Val  Pro  Leu  Pro  Pro  Ser  Pro  Pro  Ser  Asp  Ser  Pro  Val
            115                 120                 125

Asp  Gly  Leu  Ser  Ser  Ser  Phe  Lys  Ser  Ala  Phe  Asn  Gln  Val  Tyr  Lys
      130                 135                 140

Asn  Gln  Ser  Glu  Met  Ala  Ser  Thr  Leu  Asn  His  Val  Ser  Gly  Gln  Val
145                 150                 155                     160

Ser  His  Ser  Gln  Asp  Met  Val  Gln  Leu  Asn  Thr  Lys  Phe  His  Ala  Asp
                  165                 170                 175

Arg  Val  Leu  Glu  Ser  Val  Thr  Ala  Val  Asn  Asn  Arg  Leu  Gly  Gly  Gln
            180                 185                     190

Met  Glu  Tyr  Leu  Glu  Glu  Ile  Arg  Ile  Asp  Val  Trp  Asp  Thr  Gln  Arg
           195                 200                 205

Glu  Val  Arg  Lys  Ala  Lys  Asp  Glu  Leu  Tyr  Ser  Arg  Val  Ala  Ala  Val
     210                 215                 220

Ser  Tyr  Asp  Val  Leu  Tyr  Ser  Glu  Leu  Asn  Val  Leu  Arg  Ala  Ile  Asp
225                 230                 235                     240

Glu  Leu  Lys  Asp  Ser  Leu  Gly  Gly  Thr  Val  Val  Pro  Pro  Asn  Pro  Asp
                  245                 250                 255

Gln  Pro  Asn  Pro  Thr  Pro  Pro  Asp  Ser  Ser  Ser  Pro  Asn  Tyr  Thr  Gly
           260                 265                 270

Ala  Leu  Asn  Thr  Ile  Ser  Lys  Lys  Leu  Asn  Thr  Leu  Glu  Thr  Ile  Ser
     275                 280                 285
```

-continued

```
Gln Gln Leu Asp Thr Met Asn Thr Ala Leu Ser Gly Arg Cys Ser Asn
    290                 295                 300

Pro Glu Arg Cys Gln Phe Pro Ile Arg Glu Ala Glu Thr Glu Leu Glu
305                 310                 315                 320

Thr Ala Gln Gln Asn Leu Lys Gln Met Ile Asn Glu Lys Ile Thr Gln
                325                 330                 335

Ser Ala Leu His Gln Phe Lys Gly Ser Ala Ala Val Pro Ser Phe Cys
            340                 345                 350

Ser Tyr Val Glu Ala Phe Gly Tyr Asn Leu Cys Phe Asp Phe Ser Leu
        355                 360                 365

Phe Ser Glu Asn Leu His Ile Ile Arg Met Ile Val Leu Ala Met Ala
    370                 375                 380

Tyr Ile Leu Ala Ala Met Leu Ile Leu Phe Arg
385                 390                 395
```

(2) INFORMATION FOR SEQ ID NO:6:

(i) SEQUENCE CHARACTERISTICS:
      (A) LENGTH: 96 amino acids
      (B) TYPE: amino acid
      (D) TOPOLOGY: linear (ii) MOLECULE TYPE: protein (xi) SEQUENCE DESCRIPTION: SEQ ID NO:6:

```
Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
            85                  90                  95
```

What is claimed is:

1. A culture of *Vibrio cholerae* comprising a strain of the Ogawa or Inaba serotype having the chromosomal DNA coding for the A subunit and B subunit of *Vibrio cholerae* toxin deleted from the toxin locus to confer avirulence and retaining the capacity to colonize the intestine of a host animal, and having a second DNA fragment coding for zonula occludens toxin deleted.

2. The culture of *Vibrio cholerae* according to claim 1, wherein said culture comprises *Vibrio cholerae* CVD109 (ATCC 55057).

3. The culture of *Vibrio cholerae* according to claim 1, wherein said strain additionally has a mercury resistance gene inserted in the chromosome and a DNA fragment coding for B subunit of *Vibrio cholerae* toxin re-inserted into the chromosome.

4. The culture of *Vibrio cholerae* according to claim 3, wherein said mercury resistance gene and DNA coding for the B subunit of the cholera toxin are inserted in the hemolysin gene.

5. The culture of *Vibrio cholerae* according to claim 4, wherein said culture is *Vibrio cholerae* CVD110 (ATCC 55188).

6. A method of isolating deletion mutants of *Vibrio cholerae* having the cholera toxin A subunit and zonula occludens toxin genes deleted, but expressing a DNA encoder the B subunit of *Vibrio cholerae* toxin comprising:

(a) obtaining a plasmid having a *Vibrio cholerae* DNA fragment which encodes cholera toxin, a DNA fragment which encodes zonula occludens toxin, and a gene for a selectable marker of foreign origin, wherein said plasmid is incapable of extrachromosomal replication in *Vibrio cholerae*;

(b) mating a microorganism carrying the plasmid of step (a) with a virulent strain of *Vibrio cholerae* containing said DNA which encodes cholera toxin and DNA which encodes zona occludens toxin;

(c) selecting for *Vibrio cholerae* expressing said selectable marker from the *V. cholerae* chromosome;

(d) screening for *Vibrio cholerae* produced by step (c) which are sensitive to a selective agent and no longer express the selectable marker;

(e) obtaining a second plasmid comprising *V. cholerae* chromosomal sequences flanking a DNA for a gene which encodes a resistance to mercury and a DNA which encoding the B subunit of *Vibrio cholerae* toxin, and a gene for a second selectable marker, wherein said second plasmid is incapable of extrachromosomal replication in *Vibrio cholerae*;

(f) mating a microorganism carrying said second plasmid with said *Vibrio cholerae* produced in step (d);

(g) selecting for *Vibrio cholerae* expressing said second selectable marker from the *V. cholerae* chromosome;

(h) growing the selected product of step (g) in the absence of a second selective agent;

(i) screening said *Vibrio cholerae* recited in step (h) for *V. cholerae* that have a mercury resistance gene and a DNA encoding the B subunit of *V. cholerae* toxin.

7. The method of isolating deletion mutants of *Vibrio cholerae* according to claim 6, wherein said plasmid recited in step (e) is pCVD622.2B.

8. The method of isolating deletion mutants of *Vibrio cholerae* according to claim 6, wherein said *V. cholerae* chromosomal sequences in step (e) comprise hemolysin gene sequences.

9. The method of isolating deletion mutants of *Vibrio cholerae* according to claim 6, wherein the *Vibrio cholerae* recited in step (d) is *Vibrio cholerae* CVD109 (ATCC 55057).

10. The method of isolating deletion mutants of *Vibrio cholerae* according to claim 6, wherein said *Vibrio cholerae* selected in step (i) is *Vibrio cholerae* CVD110 (ATCC 55188).

11. The method of isolating deletion mutants of *Vibrio cholerae* according to claim 6, wherein said selectable marker and said second selectable marker are ampicillin resistance.

12. The method of isolating deletion mutants of *Vibrio cholerae* according to claim 6, wherein said selectable marker is ampicillin resistance and said second selectable marker is chloramphenicol resistance.

13. *Vibrio cholerae* CVD109 (ATCC 55057).

14. A culture of *Vibrio cholerae* comprising *V. cholerae* CVD109 (ATCC 55057).

15. *Vibrio cholerae* CVD110 (ATCC 55188).

16. A culture of *Vibrio cholerae* comprising *V. cholerae* CVD110 (ATCC 55188).

* * * * *